(12) United States Patent
Akamatsu et al.

(10) Patent No.: US 10,875,921 B2
(45) Date of Patent: Dec. 29, 2020

(54) ANTI-4-1BB ANTIBODIES AND THEIR USES

(71) Applicant: AbbVie Biotherapeutics Inc., Redwood City, CA (US)

(72) Inventors: Yoshiko Akamatsu, Palo Alto, CA (US); Jieyi Wang, Belmont, CA (US)

(73) Assignee: AbbVie Biotherapeutics Inc., Redwood City, CA (US)

( * ) Notice: Subject to any disclaimer, the term of this patent is extended or adjusted under 35 U.S.C. 154(b) by 140 days.

(21) Appl. No.: 16/304,646

(22) PCT Filed: May 26, 2017

(86) PCT No.: PCT/US2017/034687
§ 371 (c)(1),
(2) Date: Nov. 26, 2018

(87) PCT Pub. No.: WO2017/205745
PCT Pub. Date: Nov. 30, 2017

(65) Prior Publication Data
US 2019/0194329 A1    Jun. 27, 2019

Related U.S. Application Data

(60) Provisional application No. 62/342,497, filed on May 27, 2016.

(51) Int. Cl.
*A61K 39/00*    (2006.01)
*C07K 16/28*    (2006.01)

(52) U.S. Cl.
CPC ...... *C07K 16/2818* (2013.01); *C07K 16/2878* (2013.01); *A61K 2039/505* (2013.01); *A61K 2039/507* (2013.01); *C07K 2317/24* (2013.01); *C07K 2317/53* (2013.01); *C07K 2317/75* (2013.01)

(58) Field of Classification Search
CPC .................................................. C07K 16/2818
See application file for complete search history.

(56) References Cited

U.S. PATENT DOCUMENTS

| | | |
|---|---|---|
| 4,399,216 A | 8/1983 | Axel |
| 4,444,887 A | 4/1984 | Hoffman |
| 4,510,245 A | 4/1985 | Cousens |
| 4,634,665 A | 1/1987 | Axel |
| 4,716,111 A | 12/1987 | Osband |
| 4,816,397 A | 3/1989 | Boss |
| 4,816,567 A | 3/1989 | Cabilly |
| 4,968,615 A | 11/1990 | Koszinowski |
| 5,168,062 A | 12/1992 | Stinski |
| 5,179,017 A | 1/1993 | Axel |
| 5,225,539 A | 7/1993 | Winger |
| 5,413,923 A | 5/1995 | Kucherlapati |
| 5,530,101 A | 6/1996 | Queen |
| 5,545,806 A | 8/1996 | Lonberg |
| 5,565,332 A | 10/1996 | Hoogenboom |
| 5,569,825 A | 10/1996 | Lonberg |
| 5,585,089 A | 12/1996 | Queen |
| 5,625,126 A | 4/1997 | Lonberg |
| 5,633,425 A | 5/1997 | Lonberg |
| 5,658,570 A | 8/1997 | Newman |
| 5,661,016 A | 8/1997 | Lonberg |
| 5,681,722 A | 10/1997 | Newman |
| 5,693,761 A | 12/1997 | Queen |
| 5,693,762 A | 12/1997 | Queen |
| 5,693,780 A | 12/1997 | Newman |
| 5,807,715 A | 9/1998 | Morrison |
| 5,814,318 A | 9/1998 | Lonberg |
| 5,834,597 A | 11/1998 | Tso |
| 5,885,793 A | 3/1999 | Griffiths |
| 5,916,771 A | 6/1999 | Hori |
| 5,939,598 A | 8/1999 | Kucherlapati |
| 6,180,370 B1 | 1/2001 | Queen |
| 7,217,797 B2 | 5/2007 | Hinton |
| 7,332,581 B2 | 2/2008 | Presta |
| 8,137,667 B2 | 3/2012 | Jure-Kunkel |
| 2006/0134709 A1 | 6/2006 | Stavenhagen |
| 2007/0280931 A1 | 12/2007 | Chen |
| 2014/0178368 A1 | 6/2014 | Sharp |
| 2014/0377253 A1 | 12/2014 | Harding |

FOREIGN PATENT DOCUMENTS

| | | |
|---|---|---|
| EP | 0239400 A2 | 3/1987 |
| EP | 0519596 A1 | 12/1992 |
| EP | 0592106 A1 | 4/1994 |
| WO | 199110741 A1 | 7/1991 |
| WO | 1991009967 A1 | 7/1991 |
| WO | 199201047 A1 | 1/1992 |
| WO | 199633735 A1 | 10/1996 |
| WO | 1996034096 A1 | 10/1996 |
| WO | 1998016654 A1 | 4/1998 |
| WO | 1998024893 A2 | 6/1998 |
| WO | 1998046645 A2 | 10/1998 |
| WO | 1998050433 A2 | 11/1998 |
| WO | 2005123780 A2 | 12/2005 |
| WO | 2012032433 A1 | 3/2012 |
| WO | 2012145183 A2 | 10/2012 |

OTHER PUBLICATIONS

Strome et al., The Oncologist, 2007; 12:1084-95 (Year: 2007).*
Brand et al., Anticancer Res. 2006; 26:463-70 (Year: 2006).*
Bartkowia and Curran, 2015 "4-1BB agonists: multi-potent potentiators of tumor immunity," Front Oncol vol. 5, Art 117 (16 pages).
Bird et al., 1988 "Single-Chain Antigen-Binding Proteins," Science 242(4877):423-426.
Canfield and Morrison, 1991 "The binding affinity of human IgG for its high affinity Fc receptor is determined by multiple amino acids in the CH2 domain and is modulated by the hinge region," J Exp Med 173(6):1483-1491.
Cox et al., 1994 "A directory of human germ-line Vχ segments reveals a strong bias in their usage," Eur J Immunol 24(4):827-836.
Fisher et al., 2012 "Targeting of 4-1BB by monoclonal antibody PF-05082566 enhances T-cell function and promotes anti-tumor activity," Cancer Immunol Immunother 61(10):1721-1733.

(Continued)

*Primary Examiner* — Sheela J. Huff
(74) *Attorney, Agent, or Firm* — Dechert LLP

(57) ABSTRACT

The present disclosure provides novel anti-4-1BB antibodies, compositions including the new antibodies, nucleic acids encoding the antibodies, and methods of making and using the same.

18 Claims, 18 Drawing Sheets

Specification includes a Sequence Listing.

(56) References Cited

OTHER PUBLICATIONS

Gillies et al., 1989 "High-level expression of chimeric antibodies using adapted cDNA variable region cassettes," J Immunol Methods 125:191-202.
Hezareh et al., 2001 "Effector Function Activities of a Panel of Mutants of a Broadly Neutralizing Antibody against Human Immunodeficiency Virus Type 1," J Virol 75(24):12161-12168.
Huston et al., 1988 "Protein engineering of antibody binding sites: recovery of specific activity in an anti-digoxin single-chain Fv analogue produced in *Escherichia coli*," Proc Natl Acad Sci USA 85(16):5879-5883.
James et al., 2010 "Differential Suppression of Tumor-Specific CD8+ T Cells by Regulatory T Cells," J Immunol 185(9):5048-5055.
Jefferis and Lefranc, 2009 "Human immunoglobulin allotypes: possible implications for immunogenicity," mAbs 1(4):332-338.
Jespers et al., 1994 "Guiding the Selection of Human Antibodies from Phage Display Repertoires to a Single Epitope of an Antigen," BioTechnology 12:899-903.
Jung and Plückthun, 1997 "Improving in vivo folding and stability of a single-chain Fv antibody fragment by loop grafting," Protein Eng 10(8):959-966.
Kaplan and Meier, 1958 "Nonparametric Estimation from Incomplete Observations," J Am Stat Assoc, 53 (282):457-481.
Kaufman and Sharp, 1982 "Amplification and expression of sequences cotransfected with a modular dihydrofolate reductase complementary DNA gene," J Mol Biol 159(4):601-621.
Kohler and Milstein, 1975 "Continuous cultures of fused cells secreting antibody of predefined specificity," Nature 256(5517):495-497.
Loo et al., 1997 "Analysis of 4-1BBL and Laminin Binding to Murine 4-1BB, a Member of the Tumor Necrosis Factor Receptor Superfamily, and Comparison with Human 4-1BB," J Bio Chem 272(10):6448-6456.
Lund, et al., 1991 "Human Fc gamma RI and Fc gamma RII interact with distinct but overlapping sites on human IgG," J Immunol 147(8):2657-2662.
McCafferty et al., 1990 "Phage antibodies: filamentous phage displaying antibody variable domains," Nature 348:552-554.
Miller and Sadelain, 2015 "The journey from discoveries in fundamental immunology to cancer immunotherapy," Cancer Cell 27(4):439-449.
Morrison, 1985 "Transfectomas provide novel chimeric antibodies," Science 229(4719):1202-1207.
Murray and Baliga, 2013 "Cell-free translation of peptides and proteins:from high throughput screening to clinical production," Curr Opin Chem Biol 17(3):420-426.
Nishino et al., 2013 "Developing a Common Language for Tumor Response to Immunotherapy: Immune-Related Response Criteria Using Unidimensional Measurements," Clin Cancer Res 19(14):3936-3943.
Oi and Morrison, 1986 "Chimeric Antibodies," BioTechiques 4:214-221.
Padlan, 1991 "A possible procedure for reducing the immunogenicity of antibody variable domains while preserving their ligand-binding properties," Mol Immunol 28(4-5):489-498.
Queen et al., 1989 "A humanized antibody that binds to the interleukin 2 receptor," Proc Natl Aced Sci USA 86(24):10029-10033.
Riechmann et al., 1988 "Reshaping human antibodies for therapy," Nature 332(6162):323-327.
Riechmann and Muyldermans, 1999 "Single domain antibodies: comparison of camel VH and camelised human VH domains," J Immunol Methods 231(1-2):25-38.
Roguska et al., 1994 "Humanization of murine monoclonal antibodies through variable domain resurfacing," Proc Natl Acad Sci USA 91(3):969-973.
Shen et al., 2013 "Removal of a C-terminal serine residue proximal to the inter-chain disulfide bond of a human IgG1 lambda light chain mediates enhanced antibody stability and antibody dependent cell-mediated cytotoxicity," mAbs 5(3):418-431.
Shields et al., 2002 "Lack of Fucose on Human IgG1 N-Linked Oligosaccharide Improves Binding to Human FcγRIII and Antibody-dependent Cellular Toxicity," J Biol Chem 277(30):26733-26740.
Shinkawa et al., 2003 The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity, J Biol Chem 278(5):3466-3473.
Shire et al., 2004 "Challenges in the development of high protein concentration formulations," J Pharm Sci 93(6):1390-1402.
Studnicka et al., 1994 "Human-engineered monoclonal antibodies retain full specific binding activity by preserving non-CDR complementarity-modulating residues," Protein Eng 7(6):805-814.
Tomlinson et al., 1992 "The repertoire of human germline VH sequences reveals about fifty groups of VH segments with different hypervariable loops," J Mol Biol 227(3):776-798.
Urlaub and Chasin, 1980 "Isolation of Chinese hamster cell mutants deficient in dihydrofolate reductase activity," Proc Natl Acad Sci USA 77(7):4216-4220.
Vonderheide and Glennie, 2013 "Agonistic CD40 Antibodies and Cancer Therapy," Clin Cancer Res 19(5):1035-1043.
Wahl et al., 1983 "Improved radioimaging and tumor localization with monoclonal F(ab')2," J Nucl Med 24(4):316-325.
Wolchok et al., 2009 "Guidelines for the Evaluation of Immune Therapy Activity in Solid Tumors: Immune-Related Response Criteria," Clin Cancer Res 15(23):7412-7420.
Wolfson, 2006 "Amber Codon Flashing Ambrx Augments Proteins with Unnatural Amino Acids," Chem Biol 13(10)1011-1012.
Yazaki et al., 2004 "Humanization of the anti-CEA T84.66 antibody based on crystal structure data," Protein Eng 17(5):481-489.
Yonezawa et al., 2015 "Boosting Cancer Immunotherapy with Anti-CD137 Antibody Therapy," Clin Cancer Res 21(14):113-3120.
Zhang et al., 2006 "Antitumor efficacy of CD137 ligation is maximized by the use of a CD137 single-chain Fv-expressing whole-cell tumor vaccine compared with CD137-specific monoclonal antibody infusion," Mol Cancer Ther 5(1)149-155.

\* cited by examiner

| | | |
|---|---|---|
| Human 4-1BB | MGNSCYNIVATLLLVLNFERTRSLQDPCSNCPAGTFCDNNRNQICSPCPPNSFSSAGGQR | 60 |
| Cyno 4-1BB | MGNSCYNIVATLLLVLNFERTRSLQDLCSNCPAGTFCDNNRSQICSPCPPNSFSSAGGQR | 60 |
| Mouse 4-1BB | MGNNCYNVVVIVLLLVGCEKVGAVQNSCDNCQPGTFCRKY-NPVCKSCPPSTFSSIGGQP | 59 |
| Rat 4-1BB | MGSSCYNMVVTVLLVVGTEEVRATRNPCDSCEAGTFCSKY-PPVCTSCPPSTYSSTGGQP | 59 |
| Human 4-1BB | TCDICRQCKGVFRTRKECSSTSNAECDCTPGFHCLGAGCSMCEQDCKQGQELTKKGCKDC | 120 |
| Cyno 4-1BB | TCDICRQCKGVFKTRKECSSTSNAECDCISGYHCLGAECSMCEQDCKQGQELTKKGCKDC | 120 |
| Mouse 4-1BB | NCNICRVCAGYFRFKFCSSTHNAECECIEGFHCLGPOCTRCEKDCRPGQELTKQGCKTC | 119 |
| Rat 4-1BB | NCDICRVCQGYFRFKKPCSSTHNAECECVEGFHCLGPKCTRCEKDCRPGQELTEQGCKNC | 119 |
| Human 4-1BB | CFGTFNDQK--RGICRPWTNCSLDGKSVLVNGTKERDVVCGPSPADLSPGASSVTPPAPAR | 179 |
| Cyno 4-1BB | CFGTFNDQK--RGICRPWTNCSLDGKSVLVNGTKERDVVCGPSPADLSPGASSATPPAPAR | 179 |
| Mouse 4-1BB | SLGTFNDQNGTGVCRPWTNCSLDGRSVLKTGTTEKDVVCGPPVVSFSPSTTIS--VTPEG | 177 |
| Rat 4-1BB | GLGTFNDQDGAGVCRPWTNCSLDGRSVLKNGTKEKDVVCGPPVVSLSPTTPSAVTTPER | 179 |
| Human 4-1BB | EPGH--SPQIIFSFLALTSTALLFLLFFLTLRFSVVKRGRKKLLYIFKQPFMRPVQTTQEE | 238 |
| Cyno 4-1BB | EPGH--SPQIIF-FLALTSTVVLFLLFFLVLRFSVVKRSRKKLLYIFKQPFMRPVQTTQEE | 237 |
| Mouse 4-1BB | GPGGHSLQVLTLFLALSLALL--AFLIFIILLFSVLKWIRKKFPHIFKQPFKKTTGAAQEE | 236 |
| Rat 4-1BB | ESGERPLQVLTLFLALTLALL--LFLIFIILWFSVPKWLRKKFPHIFKQPFKKAVRTAQEE | 238 |
| Human 4-1BB | DGCSCRFPEEEEGGCEL---- | 255 (SEQ ID NO:1) |
| Cyno 4-1BB | DGCSCRFPEEEEGGCEL---- | 254 (SEQ ID NO:4) |
| Mouse 4-1BB | DACSCRCPQEEEGGGGGYEL | 256 (SEQ ID NO:3) |
| Rat 4-1BB | DACSCRFPEEEEGGGGSYEL | 258 (SEQ ID NO:5) |

*FIG. 1A*

Human 4-1BB Ligand (SEQ ID NO:2)

```
        10          20         30          40         50
MEYASDASLD  PEAPWPPAPR  ARACRVLPWA  LVAGLLLLLL  LAAACAVFLA
        60          70         80          90        100
CPWAVSGARA  SPGSAASPRL  REGPELSPDD  PAGLLDLRQG  MFAQLVAQNV
       110         120        130         140        150
LLIDGPLSWY  SDPGLAGVSL  TGGLSYKEDT  KELVVAKAGV  YYVFFQLELR
       160         170        180         190        200
RVVAGEGSGS  VSLALHLQPL  RSAAGAAALA  LTVDLPPASS  EARNSAFGFQ
       210         220        230         240        250
GRLLHLSAGQ  RLGVHLHTEA  RARHAWQLTQ  GATVLGLFRV  TPEIPAGLPS

PRSE
```

FIG. 1B

Rat Anti-4-1BB Antibody Domains
Variable domains (CDRs in bold)

TABBY101 V$_H$ (SEQ ID NO:101)
QIQLVQSGPELKKPGESVKISCKASGYTFTDFAIHWVKQAPGKGLKWMGWINTYTGKPTY
ADDFKGRFVFSLEASASTANLQISNLKNEDTATYFCSRGAPRPTNWGQGTLVTVSS

TABBY101 V$_L$ (SEQ ID NO:151)
DIQMTQSPASLSASLGETVSIECLASEDIYNNLAWYQQKPGKSPQLLIYYESRLQDGVPTRFS
GSGSGTQYSLKINSLESEDAATYFCLQDSEYPYTFGAGTKLELK

TABBY102 V$_H$ (SEQ ID NO:102)
QVQLQQSGAELAKPGSSVKISCKASGYTLTSYYLNWIKQTTGQGLEYIGY**IDTGSGGSHYN
EKFKGKATLTVDKSSSTAFMQLSSLTPVDSAVYYCARGGYYDGFFDY**WGQGVMVTVSS

TABBY102 V$_L$ (SEQ ID NO:152)
DIQMTQSPASLSASLGETVSIECLASEGISNDLAWYQQKSGKSPQFLIYAASRLQDGVPSRFS
GSGSGTRYSLKISGMQPEDEADYFCQQSYKYPPTFGSGTKLEIK

TABBY103 V$_H$ (SEQ ID NO:103)
QVQLQQSGAELVKPGSSVKISCKASDYTFTSNFLHWIKQQPGNGLEWIGW**INPGDGDTYYN
QKFNGKATLTADKSSTTAYMQLSLTSEDSAVYFCAGGNYYAAHYPPGPWYFDF**WGPGTMVTVSS

TABBY103 V$_L$ (SEQ ID NO:153)
DTVLTQSPALAVSLGQRVTISCRASKSVSIYMHWYQQKSGQQPKFLIYTASNLESGVPSRFS
GSGSGTDFTLTIDPVEADDIANYYCQQSNELPFTFGSGTKLEIK

TABBY104 V$_H$ (SEQ ID NO:104)
QVTLKESGPGILQPSQTLSLTCFSGFSLSTDGLGVTWIRQPSGKGLEWLANI**WWDDDKDY
NPSLKNRLTISKDTSNPQAFLKITNVDTADTATYYCARIVPNSGHEDY**WGQGVMIVSS

TABBY104 V$_L$ (SEQ ID NO:154)
DIQMTQSPSFLSASVGDRVTINCKASQNINRYLNWYQQKLGEAPKLLMYNTNSMQTGIPSR
FSGSGSGTDFTLTISSLQPEDVATYFCLQHNSWPRTFGGGTKLELK

*FIG. 2A*

Rat Anti-4-1BB Antibody Domains
Variable domains (CDRs in bold)

TABBY105 V$_H$ (SEQ ID NO:105)
EVQLVESGGGLVQPGRSMKLSCAASGFTFNNYDMAWVCQAPKRGLEWVATISYDGSTTY YRDSVKGRFTFSRDNAKSTLYLQMDSLRSEDTATYYCARVGAGDFDYWGQGVMTVSS

TABBY105 V$_L$ (SEQ ID NO:155)
DIRMTQSPVSLSTSLGETVNIECLASEDIYSDLAWYQQKPGKSPQLLIYSTNTLQNGVPSRFS GSGSGTQYSLKINSLQSEDVATYFCQQNNNYPYTFGAGTKLELK

TABBY106 V$_H$ (SEQ ID NO:106)
QVQLQQSGAELAKPGTSVKLSCKASGYTFTSYYIYWKQRPGQGLEWIGNIWPGN GGTFYGEKFMGKATFTADTSSSTAYMLLGSLTPEDSAYFCARRPDYSGDDYFDYWGQGVLVTVSS

TABBY106 V$_L$ (SEQ ID NO:156)
QVVLTQPKSVSTSLKSTVKLSCKLNSGNIGSYYVHWYQQHAGRSPTTMIYRDDKRP DGVPDRFSGSIDSSSNSAFLTINNVQTEDDAIYFCHSYDSTITP**VFGGGTKLTVL

TABBY107 V$_H$ (SEQ ID NO:107)
QVKLVQSGAALVKPGASVKMSCKASDYTFNDYWSWVKQRHGESLEWIGEIYPNS GATNFNFGKFRGKATLTVDNPTSTAYMELSRLTSEDSAIYYCTREYTRDWFAYWGQGTLVTVSS

TABBY107 V$_L$ (SEQ ID NO:157)
DVVLTQTPSILSATIGQSVSISCRSSQSLLDSDGNTYLYWFLQRPGQSPQRLIYLVSNL GSGVPNRFSGSGSGTDFTLKISGVEAEDLGIYYCMQPTHAPYTFGAGTKLELK

TABBY108 V$_H$ (SEQ ID NO:108)
EIQLQESGPGLVRPSQSLSLACSVTGYTITSAYDWSWIRKFPGNKMEWMGYIAYIGF TNSNPSLKSRISITRDTSKNQFFLQKSVTTEDTATYYCARWSSYIPRYFDFWGPGTMVTVSS

TABBY108 V$_L$ (SEQ ID NO:158)
QAVLTQPNSVSTSLGSTVKLSCTITSGNIEDNFVHWYQHYEGRSPTTMIHNDDKRP DGVPDRFSGSIDSSSNSAFLTINNVEIEDEAIYFCHSYVSSIN**FGGGTKLTVL

FIG. 2B

Murine Anti-4-1BB Antibody Domains
Variable domains (CDRs in bold)

TABBY1.1 V_H (SEQ ID NO:121)
EVQLVESGGDLVKPGGSQKLSCAASGFTFSSYGMSWVRQTPDRRLEWVAAIISGGSYTYYPDSVKGRFTISRDNAKNTLYLQMNSLKSEDTAMYYCARHGGYDGNYDYYAMDYWGQGTSVTVSS

TABBY1.1 V_L (SEQ ID NO:171)
DVLMTQTPLSLPVSLGDQASISCRSSQSIVDSDGITYLEWYLQKPGQSPKLLIYKVSNRFSGVPDRFSGSGSGTDFTLRISRVEAEDLGLYYCFQVSHVPWTFGGGTKLEIK

TABBY3 V_H (SEQ ID NO:123)
GVQLVESGGGLVQPGGSRKLSCAASGFTFSSFGMHWFRQAPEKGLEWVAYISSGSSTIYYADTLKGRFTISRDNPKNTLFLQMTSLRSEDTAMYYCARDWVDYWGQGTTLTVSS

TABBY3 V_L (SEQ ID NO:173)
DIVITQDELSNPVTSGESASISCRSSKSLLYKDGKTYLNWFLQRPGQSPQLLIYLMSTRASGVSDRFTGSGSGTDFTLEISRVKAEDVGVYYCQQPVEYPYTFGGGTKLEIK

TABBY5 V_H (SEQ ID NO:125)
EVQLQQSGAELVRPGASVKLSCTASGFNIKDYYMHWVKQRPEQGLEWIGRIDPEDGDTEYVPKFQGKATMTADTSSNTAYLQLSLTSEDTAVYYCTPYSNYVYWYFDVWGTGTTVTSS

TABBY5 V_L (SEQ ID NO:175)
DVVMTQTPLTLSVTIGQPASISCKSSQSLLDSDGKTYLNWLLQRPGQSPKRLIYLVSKLDSGVPDRFTGSGSGTDFTLKISRVEAEDLGVYYCWQGTHFPHTFGGGTKLEIK

TABBY6 V_H (SEQ ID NO:126)
EVQLQQSGAELVRPGASVKLSCTASGFNIKDYYMHWVKQRPEQGLEWIGRIDPEDGDTEYAPKFQGKATMTADTSSNTAYLQLSTLTSEDTAVYYCTPYSNYVYWYFDVWGTGTTVTSS

TABBY6 V_L (SEQ ID NO:176)
DVVMTQTPLTLSVTIGQAASISCKSSQSLLDSDGKTYLNWLLQRPGQSPKRLIYLVSKLDSGVPDRFTGSGSGTDFTLKISRVEAEDLGVYYCWQGTHFPHTFGGGTKLEIK

*FIG. 2C*

Murine Anti-4-1BB Antibody Domains
Variable domains (CDRs in bold)

TABBY9 V$_H$ (SEQ ID NO:129)
QVQLKQSGPGLVQPSQSLSITCTVSGFSLTSYGVHWVRQSPGKGLEWLGMIWSGGSTDYNAAFISRL
SISKDNSKSQVFFKMNSLQADDTALYFCASYGGFYETMDYWGQGTSVTVSS

TABBY9 V$_L$ (SEQ ID NO:179)
DIQMTQTTSSLSASLGDRITISCRASQDISNYLNWYQRKPDGTVKLLIYYTSRLHSGVPSRFSGSGSGRD
YSLTISNLEQEDIATYFCQQGNTLPYTFGGGTKLEIK

TABBY10 V$_H$ (SEQ ID NO:130)
QIQLVQSGPELKKPGETVKISCKASGYTFTTYGMSWVKQAPGKGLKWMGWINTYSGVPTYADDFK
GRFAFSLETSASTAYLQINNLKNEDTATYFCARGNDGNYYGWFAHWGQGTLVTVSA

TABBY10 V$_L$ (SEQ ID NO:180)
DIQMTQSPSSLSASLGGKVTITCKASQDIHNYISWYQHKPGKGPRLVIHYTSTLQPGIPSRFSGSGSGRD
YSFSISNLEPEDIATYYCLQYDNLYTFGGGTKLEIK

FIG. 2D

Humanized Anti-4-1BB Antibody Domains
Variable domains (CDRs in bold)

hu106.1x V_H (SEQ ID NO:109)
EVQLVQSGAEVKKPGSSVKVSCKASGYTFTSYYIYWVRQAPGQGLEWIGNIWPGNGGTFY
GEKFMGRATFTADTSTSTAYMELSSLRSEDTAVYYCARRPDYSGDDYFDYWGQGTLVTVSS hu106.1x V_L (SEQ ID NO:159)
NVMLTQPHSVSESPGKTVTISCKLNSGNIGSYYVHWYQQRPGSSPTTMIYRDDKRPDGVPD
RFSGSIDSSSNSASLTISGLKTEDEADYYCHSYDSTITPVFGGGTKLTVL hu106.1y V_H (SEQ ID NO:110)
EVQLVESGGGLVQPGGSLRLSCAASGYTFTSYYIYWVRQAPGKGLEWIGNIWPGNGGTFY
GEKFMGRATFSADTSKNTAYLQMNSLRAEDTAVYYCARRPDYSGDDYFDYWGQGTLVTVSS hu106.2x V_L (SEQ ID NO:160)
QVVLTQPPSASGTPGQRVTISCKLNSGNIGSYYVHWYQQLPGTAPKTMIYRDDKRPDGVPD
RFSGSSSNSASLAISGLQSEDEADYYCHSYDSTITPVFGGGTKLTVL hu106.3x V_L (SEQ ID NO:161)
SVELTQPPSVSVSPGQTARITCKLNSGNIGSYYVHWYQQKPGQAPVTMIYRDDKRPDGIPER
FSGSSDSSSNSAFLTISGVQAEDEADYYCHSYDSTITPVFGGGTKLTVL hu106.4x V_L (SEQ ID NO:162)
EVVLTQPPSLSASPGASARLTCKLNSGNIGSYYVHWYQQKPGSSPPRTMIYRDDKRPDGVPSR
FSGSKDSSSNSAFLLISGLQSEDEADYYCHSYDSTITPVFGGGTKLTVL hu106.5x V_L (SEQ ID NO:163)
DVQLTQSPSSLSASVGDRVTITCKLNSGNIGSYYVHWYQQKPGKAPKTMIYRDDKRPDGVP
SRFSGSGDSSSNSAFLTISSLQPEDFATYYCHSYDSTITPVFGQGTKVEIK

*FIG. 2E*

Humanized Anti-4-1BB Antibody Domains
Variable domains (CDRs in bold)

hu107.1x V$_H$ (SEQ ID NO:111)
EVQLVQSGAEVKKPGSSVKVSCKASDYTFNDYWVSWVRQAPGQGLEWIGEIYPNSGATNF NGKFRGRATLTVDNSASTAYMELSSLRSEDTAVYYCTREYTRDWFAYWGQGTLVTVSS hu107.1x V$_L$ (SEQ ID NO:164)
DVVLTQSPLSLPVTLGQPASISCRSSQSLLDSDGNTYLYWFQQRPGQSPRRLIYLVSNLGSGV PDRFSGSGSGTDFTLKISRVEAEDVGVYYCMQPTHAPYTFGQGTKLEIK hu107.1y V$_H$ (SEQ ID NO:112)
EVQLVESGGGLVQPGGSLRLSCAASGYTFNDYWVSWVRQAPGKGLEWIGEIYPNSGATNF NGKFRGRATLSVDNSKNTAYLQMNSLRAEDTAVYYCTREYTRDWFAYWGQGTLVTVSS hu107.1y V$_L$ (SEQ ID NO:165)
DVQLTQSPSSLSASVGDRVTITCRSSQSLLDSDGNTYLYWFQQKPGKAPKRLIYLVSNLGSG VPSRFSGSGSGTDFTLTISSLQPEDFATYYCMQPTHAPYTFGQGTKVEIK

*FIG. 2F*

```
                           SEQUENCE LISTING

<160> NUMBER OF SEQ ID NOS: 315

<210> SEQ ID NO 1
<211> LENGTH: 184
<212> TYPE: PRT
<213> ORGANISM: Homo sapiens

<400> SEQUENCE: 1

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser
            180

<210> SEQ ID NO 2
<211> LENGTH: 254
<212> TYPE: PRT
<213> ORGANISM: Homo sapiens

<400> SEQUENCE: 2

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60
```

Ala Ala Ser Pro Arg Leu Arg Glu Gly Pro Glu Leu Ser Pro Asp Asp
 65                  70                  75                  80

Pro Ala Gly Leu Leu Asp Leu Arg Gln Gly Met Phe Ala Gln Leu Val
                 85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 3
<211> LENGTH: 256
<212> TYPE: PRT
<213> ORGANISM: Mus sp.

<400> SEQUENCE: 3

Met Gly Asn Asn Cys Tyr Asn Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
        35                  40                  45

Pro Ser Thr Phe Ser Ser Ile Gly Gly Gln Pro Asn Cys Asn Ile Cys
    50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
    130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala

```
                180                 185                 190
Leu Ser Leu Ala Leu Leu Ala Phe Leu Ile Phe Ile Ile Leu Leu Phe
            195                 200                 205

Ser Val Leu Lys Trp Ile Arg Lys Lys Phe Pro His Ile Phe Lys Gln
        210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Tyr Glu Leu
                245                 250                 255

<210> SEQ ID NO 4
<211> LENGTH: 254
<212> TYPE: PRT
<213> ORGANISM: Macaca fascicularis

<400> SEQUENCE: 4

Met Gly Asn Ser Cys Tyr Asn Ile Val Ala Thr Leu Leu Leu Val Leu
1               5                   10                  15

Asn Phe Glu Arg Thr Arg Ser Leu Gln Asp Leu Cys Ser Asn Cys Pro
            20                  25                  30

Ala Gly Thr Phe Cys Asp Asn Asn Arg Ser Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Lys Thr Arg Lys Glu Cys Ser Ser
65                  70                  75                  80

Thr Ser Asn Ala Glu Cys Asp Cys Ile Ser Gly Tyr His Cys Leu Gly
                85                  90                  95

Ala Glu Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ala Thr Pro Pro Ala
                165                 170                 175

Pro Ala Arg Glu Pro Gly His Ser Pro Gln Ile Ile Phe Phe Leu Ala
            180                 185                 190

Leu Thr Ser Thr Val Val Leu Phe Leu Phe Phe Leu Val Leu Arg
        195                 200                 205

Phe Ser Val Val Lys Arg Ser Arg Lys Lys Leu Leu Tyr Ile Phe Lys
    210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Glu Gly Gly Cys Glu Leu
                245                 250

<210> SEQ ID NO 5
<211> LENGTH: 258
<212> TYPE: PRT
<213> ORGANISM: Rattus sp.

<400> SEQUENCE: 5

Met Gly Ser Ser Cys Tyr Asn Met Val Val Thr Val Leu Leu Val Val
```

```
  1               5                  10                 15
Gly Thr Glu Glu Val Arg Ala Thr Arg Asn Pro Cys Asp Ser Cys Glu
                 20                 25                 30
Ala Gly Thr Phe Cys Ser Lys Tyr Pro Pro Val Cys Thr Ser Cys Pro
                 35                 40                 45
Pro Ser Thr Tyr Ser Ser Thr Gly Gly Gln Pro Asn Cys Asp Ile Cys
 50                  55                 60
Arg Val Cys Gln Gly Tyr Phe Arg Phe Lys Lys Pro Cys Ser Ser Thr
 65                  70                 75                 80
His Asn Ala Glu Cys Glu Cys Val Gly Phe His Cys Leu Gly Pro
                 85                 90                 95
Lys Cys Thr Arg Cys Glu Lys Asp Cys Arg Pro Gly Gln Glu Leu Thr
                 100                105                110
Glu Gln Gly Cys Lys Asn Cys Gly Leu Gly Thr Phe Asn Asp Gln Asp
                 115                120                125
Gly Ala Gly Val Cys Arg Pro Trp Thr Asn Cys Ser Leu Asp Gly Arg
 130                 135                140
Ser Val Leu Lys Asn Gly Thr Lys Glu Lys Asp Val Val Cys Gly Pro
145                  150                155                160
Pro Val Val Ser Leu Ser Pro Ser Thr Thr Pro Ser Ala Val Thr Thr
                 165                170                175
Pro Glu Arg Glu Ser Gly Glu Arg Pro Leu Gln Val Leu Thr Leu Phe
                 180                185                190
Leu Ala Leu Thr Leu Ala Leu Leu Leu Phe Leu Ile Phe Ile Ile Leu
                 195                200                205
Trp Phe Ser Val Pro Lys Trp Leu Arg Lys Lys Phe Pro His Ile Phe
                 210                215                220
Lys Gln Pro Phe Lys Lys Ala Val Arg Thr Ala Gln Glu Glu Asp Ala
225                  230                235                240
Cys Ser Cys Arg Phe Pro Glu Glu Glu Glu Gly Gly Gly Gly Ser Tyr
                 245                250                255
Glu Leu
```

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Tyr Thr Phe Thr Asp Phe Ala Ile His
1               5                   10

<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Tyr Thr Leu Thr Ser Tyr Tyr Leu Asn
1               5                   10

<210> SEQ ID NO 13
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Asp Tyr Thr Phe Thr Ser Asn Phe Leu His
1               5                   10

<210> SEQ ID NO 14
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Phe Ser Leu Ser Thr Asp Gly Leu Gly Val Thr
1               5                   10

<210> SEQ ID NO 15
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Phe Thr Phe Asn Asn Tyr Asp Met Ala
1               5                   10

<210> SEQ ID NO 16
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Tyr Thr Phe Thr Ser Tyr Tyr Ile Tyr
1               5                   10

<210> SEQ ID NO 17
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Asp Tyr Thr Phe Asn Asp Tyr Trp Val Ser
1               5                   10

<210> SEQ ID NO 18
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Tyr Thr Ile Thr Ser Ala Tyr Asp Trp Ser
1               5                   10

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly Tyr Thr Phe Asn Asp Tyr Trp Val Ser
1               5                   10

<210> SEQ ID NO 20

<400> SEQUENCE: 20

000

<210> SEQ ID NO 21
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

-continued

Trp Ile Asn Thr Tyr Thr Gly Lys Pro Thr Tyr Ala Asp Asp Phe Lys
1               5                   10                  15

Gly

<210> SEQ ID NO 22
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Tyr Ile Asp Thr Gly Ser Gly Gly Ser His Tyr Asn Glu Lys Phe Lys
1               5                   10                  15

Gly

<210> SEQ ID NO 23
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Trp Ile Asn Pro Gly Asp Gly Asp Thr Tyr Tyr Asn Gln Lys Phe Asn
1               5                   10                  15

Gly

<210> SEQ ID NO 24
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Asn Ile Trp Trp Asp Asp Asp Lys Asp Tyr Asn Pro Ser Leu Lys Asn
1               5                   10                  15

<210> SEQ ID NO 25
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Thr Ile Ser Tyr Asp Gly Ser Thr Thr Tyr Tyr Arg Asp Ser Val Lys
1               5                   10                  15

Gly

<210> SEQ ID NO 26
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Asn Ile Trp Pro Gly Asn Gly Gly Thr Phe Tyr Gly Glu Lys Phe Met
1               5                   10                  15

Gly

<210> SEQ ID NO 27
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Glu Ile Tyr Pro Asn Ser Gly Ala Thr Asn Phe Asn Gly Lys Phe Arg
1               5                   10                  15

Gly

<210> SEQ ID NO 28
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Tyr Ile Ala Tyr Ile Gly Phe Thr Asn Ser Asn Pro Ser Leu Lys Ser
1               5                   10                  15

<210> SEQ ID NO 29

<400> SEQUENCE: 29

000

<210> SEQ ID NO 30

<400> SEQUENCE: 30

000

<210> SEQ ID NO 31
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gly Ala Pro Arg Pro Thr Asn
1               5

<210> SEQ ID NO 32
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 32

Gly Gly Tyr Tyr Asp Gly Phe Phe Asp Tyr
1               5                   10

<210> SEQ ID NO 33
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gly Asn Tyr Tyr Ala Ala His Tyr Pro Pro Gly Pro Trp Tyr Phe Asp
1               5                   10                  15

Phe

<210> SEQ ID NO 34
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ile Val Pro Asn Ser Gly His Glu Asp Tyr
1               5                   10

<210> SEQ ID NO 35
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Val Gly Ala Gly Asp Phe Asp Tyr
1               5

<210> SEQ ID NO 36
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Arg Pro Asp Tyr Ser Gly Asp Asp Tyr Phe Asp Tyr
1               5                   10

<210> SEQ ID NO 37
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 37

Glu Tyr Thr Arg Asp Trp Phe Ala Tyr
1               5

<210> SEQ ID NO 38
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Trp Ser Ser Tyr Ile Pro Arg Tyr Phe Asp Phe
1               5                   10

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47
```

```
<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Leu Ala Ser Glu Asp Ile Tyr Asn Asn Leu Ala
1               5                   10

<210> SEQ ID NO 52
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Leu Ala Ser Glu Gly Ile Ser Asn Asp Leu Ala
1               5                   10

<210> SEQ ID NO 53
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Arg Ala Ser Lys Ser Val Ser Ile Tyr Met His
1               5                   10

<210> SEQ ID NO 54
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 54

Lys Ala Ser Gln Asn Ile Asn Arg Tyr Leu Asn
1               5                   10

<210> SEQ ID NO 55
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Leu Ala Ser Glu Asp Ile Tyr Ser Asp Leu Ala
1               5                   10

<210> SEQ ID NO 56
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Lys Leu Asn Ser Gly Asn Ile Gly Ser Tyr Tyr Val His
1               5                   10

<210> SEQ ID NO 57
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Arg Ser Ser Gln Ser Leu Leu Asp Ser Asp Gly Asn Thr Tyr Leu Tyr
1               5                   10                  15

<210> SEQ ID NO 58
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Thr Ile Thr Ser Gly Asn Ile Glu Asp Asn Phe Val His
1               5                   10

<210> SEQ ID NO 59

<400> SEQUENCE: 59

000

<210> SEQ ID NO 60

<400> SEQUENCE: 60

000

```
<210> SEQ ID NO 61
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Tyr Glu Ser Arg Leu Gln Asp
1               5

<210> SEQ ID NO 62
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ala Ala Ser Arg Leu Gln Asp
1               5

<210> SEQ ID NO 63
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Thr Ala Ser Asn Leu Glu Ser
1               5

<210> SEQ ID NO 64
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Asn Thr Asn Ser Met Gln Thr
1               5

<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ser Thr Asn Thr Leu Gln Asn
1               5

<210> SEQ ID NO 66
<211> LENGTH: 7
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Arg Asp Asp Lys Arg Pro Asp
1               5

<210> SEQ ID NO 67
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Leu Val Ser Asn Leu Gly Ser
1               5

<210> SEQ ID NO 68
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Asn Asp Asp Lys Arg Pro Asp
1               5

<210> SEQ ID NO 69

<400> SEQUENCE: 69

000

<210> SEQ ID NO 70

<400> SEQUENCE: 70

000

<210> SEQ ID NO 71
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Leu Gln Asp Ser Glu Tyr Pro Tyr Thr
1               5

<210> SEQ ID NO 72
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
```

```
<400> SEQUENCE: 72

Gln Gln Ser Tyr Lys Tyr Pro Pro Thr
1               5

<210> SEQ ID NO 73
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gln Gln Ser Asn Glu Leu Pro Phe Thr
1               5

<210> SEQ ID NO 74
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Leu Gln His Asn Ser Trp Pro Arg Thr
1               5

<210> SEQ ID NO 75
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Gln Gln Asn Asn Asn Tyr Pro Tyr Thr
1               5

<210> SEQ ID NO 76
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

His Ser Tyr Asp Ser Thr Ile Thr Pro Val
1               5                   10

<210> SEQ ID NO 77
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77
```

```
Met Gln Pro Thr His Ala Pro Tyr Thr
1               5
```

<210> SEQ ID NO 78
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

```
His Ser Tyr Val Ser Ser Ile Asn Ile
1               5
```

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

```
<210> SEQ ID NO 88

<400> SEQUENCE: 88

000

<210> SEQ ID NO 89

<400> SEQUENCE: 89

000

<210> SEQ ID NO 90
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Gly Gly Gly Gly Ser Gly Gly Gly Gly Ser Gly Gly Gly Gly Ser
1               5                   10                  15

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000
```

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 101

Gln Ile Gln Leu Val Gln Ser Gly Pro Glu Leu Lys Pro Gly Glu
1               5                   10                  15

Ser Val Lys Ile Ser Cys Lys Ala Ser Gly Tyr Thr Phe Thr Asp Phe
                20                  25                  30

Ala Ile His Trp Val Lys Gln Ala Pro Gly Lys Gly Leu Lys Trp Met
            35                  40                  45

Gly Trp Ile Asn Thr Tyr Thr Gly Lys Pro Thr Tyr Ala Asp Asp Phe
        50                  55                  60

Lys Gly Arg Phe Val Phe Ser Leu Glu Ala Ser Ala Ser Thr Ala Asn
65                  70                  75                  80

Leu Gln Ile Ser Asn Leu Lys Asn Glu Asp Thr Ala Thr Tyr Phe Cys
                85                  90                  95

Ser Arg Gly Ala Pro Arg Pro Thr Asn Trp Gly Gln Gly Thr Leu Val
            100                 105                 110

Thr Val Ser Ser
        115

<210> SEQ ID NO 102
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 102

Gln Val Gln Leu Gln Gln Ser Gly Ala Glu Leu Ala Lys Pro Gly Ser
1               5                   10                  15

Ser Val Lys Ile Ser Cys Lys Ala Ser Gly Tyr Thr Leu Thr Ser Tyr
                20                  25                  30

Tyr Leu Asn Trp Ile Lys Gln Thr Thr Gly Gln Gly Leu Glu Tyr Ile
            35                  40                  45

```
Gly Tyr Ile Asp Thr Gly Ser Gly Ser His Tyr Asn Glu Lys Phe
        50                  55                  60

Lys Gly Lys Ala Thr Leu Thr Val Asp Lys Ser Ser Thr Ala Phe
65                  70                  75                  80

Met Gln Leu Ser Ser Leu Thr Pro Val Asp Ser Ala Val Tyr Tyr Cys
                85                  90                  95

Ala Arg Gly Gly Tyr Tyr Asp Gly Phe Phe Asp Tyr Trp Gly Gln Gly
            100                 105                 110

Val Met Val Thr Val Ser Ser
        115
```

<210> SEQ ID NO 103
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 103

```
Gln Val Gln Leu Gln Gln Ser Gly Ala Glu Leu Val Lys Pro Gly Ser
1               5                   10                  15

Ser Val Lys Ile Ser Cys Lys Ala Ser Asp Tyr Thr Phe Thr Ser Asn
            20                  25                  30

Phe Leu His Trp Ile Lys Gln Gln Pro Gly Asn Gly Leu Glu Trp Ile
        35                  40                  45

Gly Trp Ile Asn Pro Gly Asp Gly Asp Thr Tyr Tyr Asn Gln Lys Phe
    50                  55                  60

Asn Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Gly Gly Asn Tyr Tyr Ala Ala His Tyr Pro Pro Gly Pro Trp Tyr
            100                 105                 110

Phe Asp Phe Trp Gly Pro Gly Thr Met Val Thr Val Ser Ser
        115                 120                 125
```

<210> SEQ ID NO 104
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 104

```
Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Ser Thr Asp
            20                  25                  30

Gly Leu Gly Val Thr Trp Ile Arg Gln Pro Ser Gly Lys Gly Leu Glu
        35                  40                  45

Trp Leu Ala Asn Ile Trp Trp Asp Asp Lys Asp Tyr Asn Pro Ser
    50                  55                  60

Leu Lys Asn Arg Leu Thr Ile Ser Lys Asp Thr Ser Asn Pro Gln Ala
65                  70                  75                  80

Phe Leu Lys Ile Thr Asn Val Asp Thr Ala Asp Thr Ala Thr Tyr Tyr
```

```
                85                  90                  95
Cys Ala Arg Ile Val Pro Asn Ser Gly His Glu Asp Tyr Trp Gly Gln
            100                 105                 110
Gly Val Met Val Ile Val Ser Ser
            115                 120

<210> SEQ ID NO 105
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Glu Val Gln Leu Val Glu Ser Gly Gly Gly Leu Val Gln Pro Gly Arg
1               5                   10                  15

Ser Met Lys Leu Ser Cys Ala Ala Ser Gly Phe Thr Phe Asn Asn Tyr
            20                  25                  30

Asp Met Ala Trp Val Cys Gln Ala Pro Lys Arg Gly Leu Glu Trp Val
        35                  40                  45

Ala Thr Ile Ser Tyr Asp Gly Ser Thr Thr Tyr Arg Asp Ser Val
    50                  55                  60

Lys Gly Arg Phe Thr Phe Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg Val Gly Ala Gly Asp Phe Asp Tyr Trp Gly Gln Gly Val Met
            100                 105                 110

Val Thr Val Ser Ser
            115

<210> SEQ ID NO 106
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Gln Val Gln Leu Gln Gln Ser Gly Ala Glu Leu Ala Lys Pro Gly Thr
1               5                   10                  15

Ser Val Lys Leu Ser Cys Lys Ala Ser Gly Tyr Thr Phe Thr Ser Tyr
            20                  25                  30

Tyr Ile Tyr Trp Val Lys Gln Arg Pro Gly Gln Gly Leu Glu Trp Ile
        35                  40                  45

Gly Asn Ile Trp Pro Gly Asn Gly Gly Thr Phe Tyr Gly Glu Lys Phe
    50                  55                  60

Met Gly Lys Ala Thr Phe Thr Ala Asp Thr Ser Ser Thr Ala Tyr
65                  70                  75                  80

Met Leu Leu Gly Ser Leu Thr Pro Glu Asp Ser Ala Tyr Phe Cys
                85                  90                  95

Ala Arg Arg Pro Asp Tyr Ser Gly Asp Asp Tyr Phe Asp Tyr Trp Gly
            100                 105                 110

Gln Gly Val Leu Val Thr Val Ser Ser
            115                 120
```

<210> SEQ ID NO 107
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 107

Gln Val Lys Leu Val Gln Ser Gly Ala Ala Leu Val Lys Pro Gly Ala
1               5                   10                  15

Ser Val Lys Met Ser Cys Lys Ala Ser Asp Tyr Thr Phe Asn Asp Tyr
            20                  25                  30

Trp Val Ser Trp Val Lys Gln Arg His Gly Glu Ser Leu Glu Trp Ile
        35                  40                  45

Gly Glu Ile Tyr Pro Asn Ser Gly Ala Thr Asn Phe Asn Gly Lys Phe
    50                  55                  60

Arg Gly Lys Ala Thr Leu Thr Val Asp Asn Pro Thr Ser Thr Ala Tyr
65                  70                  75                  80

Met Glu Leu Ser Arg Leu Thr Ser Glu Asp Ser Ala Ile Tyr Tyr Cys
                85                  90                  95

Thr Arg Glu Tyr Thr Arg Asp Trp Phe Ala Tyr Trp Gly Gln Gly Thr
            100                 105                 110

Leu Val Thr Val Ser Ser
        115

<210> SEQ ID NO 108
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 108

Glu Ile Gln Leu Gln Glu Ser Gly Pro Gly Leu Val Arg Pro Ser Gln
1               5                   10                  15

Ser Leu Ser Leu Ala Cys Ser Val Thr Gly Tyr Thr Ile Thr Ser Ala
            20                  25                  30

Tyr Asp Trp Ser Trp Ile Arg Lys Phe Pro Gly Asn Lys Met Glu Trp
        35                  40                  45

Met Gly Tyr Ile Ala Tyr Ile Gly Phe Thr Asn Ser Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Lys Ser Val Thr Thr Glu Asp Thr Ala Thr Tyr Tyr Cys
                85                  90                  95

Ala Arg Trp Ser Ser Tyr Ile Pro Arg Tyr Phe Asp Phe Trp Gly Pro
            100                 105                 110

Gly Thr Met Val Thr Val Ser Ser
        115                 120

<210> SEQ ID NO 109
<211> LENGTH: 121
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 109

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Tyr Ile Tyr Trp Val Arg Gln Ala Pro Gly Gln Gly Leu Glu Trp Ile
        35                  40                  45

Gly Asn Ile Trp Pro Gly Asn Gly Gly Thr Phe Tyr Gly Glu Lys Phe
50                  55                  60

Met Gly Arg Ala Thr Phe Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Pro Asp Tyr Ser Gly Asp Asp Tyr Phe Asp Tyr Trp Gly
            100                 105                 110

Gln Gly Thr Leu Val Thr Val Ser Ser
        115                 120

<210> SEQ ID NO 110
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Tyr Ile Tyr Trp Val Arg Gln Ala Pro Gly Lys Gly Leu Glu Trp Ile
        35                  40                  45

Gly Asn Ile Trp Pro Gly Asn Gly Gly Thr Phe Tyr Gly Glu Lys Phe
50                  55                  60

Met Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Pro Asp Tyr Ser Gly Asp Asp Tyr Phe Asp Tyr Trp Gly
            100                 105                 110

Gln Gly Thr Leu Val Thr Val Ser Ser
        115                 120

<210> SEQ ID NO 111
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Glu Val Gln Leu Val Gln Ser Gly Ala Glu Val Lys Lys Pro Gly Ser
```

```
            1               5                  10                 15
         Ser Val Lys Val Ser Cys Lys Ala Ser Asp Tyr Thr Phe Asn Asp Tyr
                     20                  25                 30

Trp Val Ser Trp Val Arg Gln Ala Pro Gly Gln Gly Leu Glu Trp Ile
                     35                  40                 45

Gly Glu Ile Tyr Pro Asn Ser Gly Ala Thr Asn Phe Asn Gly Lys Phe
                     50                  55                 60

Arg Gly Arg Ala Thr Leu Thr Val Asp Asn Ser Ala Ser Thr Ala Tyr
         65                  70                  75                 80

Met Glu Leu Ser Ser Leu Arg Ser Glu Asp Thr Ala Val Tyr Tyr Cys
                         85                  90                 95

Thr Arg Glu Tyr Thr Arg Asp Trp Phe Ala Tyr Trp Gly Gln Gly Thr
                        100                 105                110

Leu Val Thr Val Ser Ser
                        115

<210> SEQ ID NO 112
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Glu Val Gln Leu Val Glu Ser Gly Gly Gly Leu Val Gln Pro Gly Gly
         1               5                  10                 15

Ser Leu Arg Leu Ser Cys Ala Ala Ser Gly Tyr Thr Phe Asn Asp Tyr
                     20                  25                 30

Trp Val Ser Trp Val Arg Gln Ala Pro Gly Lys Gly Leu Glu Trp Ile
                     35                  40                 45

Gly Glu Ile Tyr Pro Asn Ser Gly Ala Thr Asn Phe Asn Gly Lys Phe
                     50                  55                 60

Arg Gly Arg Ala Thr Leu Ser Val Asp Asn Ser Lys Asn Thr Ala Tyr
         65                  70                  75                 80

Leu Gln Met Asn Ser Leu Arg Ala Glu Asp Thr Ala Val Tyr Tyr Cys
                         85                  90                 95

Thr Arg Glu Tyr Thr Arg Asp Trp Phe Ala Tyr Trp Gly Gln Gly Thr
                        100                 105                110

Leu Val Thr Val Ser Ser
                        115

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000
```

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 121

```
Glu Val Gln Leu Val Glu Ser Gly Gly Asp Leu Val Lys Pro Gly Gly
 1               5                  10                  15

Ser Gln Lys Leu Ser Cys Ala Ala Ser Gly Phe Thr Phe Ser Ser Tyr
             20                  25                  30

Gly Met Ser Trp Val Arg Gln Thr Pro Asp Arg Arg Leu Glu Trp Val
         35                  40                  45

Ala Ala Ile Ile Ser Gly Gly Ser Tyr Thr Tyr Pro Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Met Tyr Tyr Cys
                 85                  90                  95

Ala Arg His Gly Gly Tyr Asp Gly Asn Tyr Tyr Ala Met Asp
                100                 105                 110

Tyr Trp Gly Gln Gly Thr Ser Val Thr Val Ser Ser
        115                 120
```

<210> SEQ ID NO 122

<400> SEQUENCE: 122

000

<210> SEQ ID NO 123
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 123

Gly Val Gln Leu Val Glu Ser Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Phe Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Leu
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Asp Trp Val Asp Tyr Trp Gly Gln Gly Thr Thr Leu Thr Val
            100                 105                 110

Ser Ser

<210> SEQ ID NO 124

<400> SEQUENCE: 124

000

<210> SEQ ID NO 125
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 125

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Arg Ile Asp Pro Glu Asp Gly Asp Thr Glu Tyr Val Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Pro Tyr Ser Asn Tyr Val Tyr Tyr Phe Asp Val Trp Gly Thr
            100                 105                 110

Gly Thr Thr Val Thr Val Ser Ser
            115                 120

-continued

```
<210> SEQ ID NO 126
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Tyr
                20                  25                  30

Tyr Met His Trp Val Lys Gln Arg Pro Glu Gln Gly Leu Glu Trp Ile
            35                  40                  45

Gly Arg Ile Asp Pro Glu Asp Gly Asp Thr Glu Tyr Ala Pro Lys Phe
        50                  55                  60

Gln Gly Lys Ala Thr Met Thr Ala Asp Thr Ser Ser Asn Thr Ala Tyr
65                  70                  75                  80

Leu Gln Leu Ser Thr Leu Thr Ser Glu Asp Thr Ala Val Tyr Tyr Cys
                85                  90                  95

Thr Pro Tyr Ser Asn Tyr Val Tyr Trp Tyr Phe Asp Val Trp Gly Thr
                100                 105                 110

Gly Thr Thr Val Thr Val Ser Ser
            115                 120

<210> SEQ ID NO 127

<400> SEQUENCE: 127

000

<210> SEQ ID NO 128

<400> SEQUENCE: 128

000

<210> SEQ ID NO 129
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
                20                  25                  30

Gly Val His Trp Val Arg Gln Ser Pro Gly Lys Gly Leu Glu Trp Leu
            35                  40                  45

Gly Met Ile Trp Ser Gly Gly Ser Thr Asp Tyr Asn Ala Ala Phe Ile
        50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Leu Tyr Phe Cys Ala
                85                  90                  95
```

Ser Tyr Gly Gly Phe Tyr Glu Thr Met Asp Tyr Trp Gly Gln Gly Thr
                100                 105                 110

Ser Val Thr Val Ser Ser
        115

<210> SEQ ID NO 130
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Asn Asp Gly Asn Tyr Tyr Gly Trp Phe Ala His Trp Gly
            100                 105                 110

Gln Gly Thr Leu Val Thr Val Ser Ala
        115                 120

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

```
<400> SEQUENCE: 136
000

<210> SEQ ID NO 137
<400> SEQUENCE: 137
000

<210> SEQ ID NO 138
<400> SEQUENCE: 138
000

<210> SEQ ID NO 139
<400> SEQUENCE: 139
000

<210> SEQ ID NO 140
<400> SEQUENCE: 140
000

<210> SEQ ID NO 141
<400> SEQUENCE: 141
000

<210> SEQ ID NO 142
<400> SEQUENCE: 142
000

<210> SEQ ID NO 143
<400> SEQUENCE: 143
000

<210> SEQ ID NO 144
<400> SEQUENCE: 144
000

<210> SEQ ID NO 145
<400> SEQUENCE: 145
000

<210> SEQ ID NO 146
<400> SEQUENCE: 146
000

<210> SEQ ID NO 147
<400> SEQUENCE: 147
```

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 151

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Asp Ile Tyr Asn Asn
            20                  25                  30

Leu Ala Trp Tyr Gln Gln Lys Pro Gly Lys Ser Pro Gln Leu Leu Ile
        35                  40                  45

Tyr Tyr Glu Ser Arg Leu Gln Asp Gly Val Pro Thr Arg Phe Ser Gly
    50                  55                  60

Ser Gly Ser Gly Thr Gln Tyr Ser Leu Lys Ile Asn Ser Leu Glu Ser
65                  70                  75                  80

Glu Asp Ala Ala Thr Tyr Phe Cys Leu Gln Asp Ser Glu Tyr Pro Tyr
                85                  90                  95

Thr Phe Gly Ala Gly Thr Lys Leu Glu Leu Lys
            100                 105

<210> SEQ ID NO 152
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 152

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Gly Ile Ser Asn Asp
            20                  25                  30

Leu Ala Trp Tyr Gln Gln Lys Ser Gly Lys Ser Pro Gln Phe Leu Ile
        35                  40                  45

Tyr Ala Ala Ser Arg Leu Gln Asp Gly Val Pro Ser Arg Phe Ser Gly

```
                    50                  55                  60
Ser Gly Ser Gly Thr Arg Tyr Ser Leu Lys Ile Ser Gly Met Gln Pro
 65                  70                  75                  80

Glu Asp Glu Ala Asp Tyr Phe Cys Gln Gln Ser Tyr Lys Tyr Pro Pro
                     85                  90                  95

Thr Phe Gly Ser Gly Thr Lys Leu Glu Ile Lys
                100                 105

<210> SEQ ID NO 153
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 153

Asp Thr Val Leu Thr Gln Ser Pro Ala Leu Ala Val Ser Leu Gly Gln
 1               5                  10                  15

Arg Val Thr Ile Ser Cys Arg Ala Ser Lys Ser Val Ser Ile Tyr Met
                20                  25                  30

His Trp Tyr Gln Gln Lys Ser Gly Gln Gln Pro Lys Phe Leu Ile Tyr
             35                  40                  45

Thr Ala Ser Asn Leu Glu Ser Gly Val Pro Ser Arg Phe Ser Gly Ser
         50                  55                  60

Gly Ser Gly Thr Asp Phe Thr Leu Thr Ile Asp Pro Val Glu Ala Asp
 65                  70                  75                  80

Asp Ile Ala Asn Tyr Tyr Cys Gln Gln Ser Asn Glu Leu Pro Phe Thr
                 85                  90                  95

Phe Gly Ser Gly Thr Lys Leu Glu Ile Lys
                100                 105

<210> SEQ ID NO 154
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 154

Asp Ile Gln Met Thr Gln Ser Pro Ser Phe Leu Ser Ala Ser Val Gly
 1               5                  10                  15

Asp Arg Val Thr Ile Asn Cys Lys Ala Ser Gln Asn Ile Asn Arg Tyr
                20                  25                  30

Leu Asn Trp Tyr Gln Gln Lys Leu Gly Glu Ala Pro Lys Leu Leu Met
             35                  40                  45

Tyr Asn Thr Asn Ser Met Gln Thr Gly Ile Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Val Ala Thr Tyr Phe Cys Leu Gln His Asn Ser Trp Pro Arg
                 85                  90                  95

Thr Phe Gly Gly Gly Thr Lys Leu Glu Leu Lys
                100                 105

<210> SEQ ID NO 155
```

-continued

```
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 155

Asp Ile Arg Met Thr Gln Ser Pro Val Ser Leu Ser Thr Ser Leu Gly
1               5                   10                  15

Glu Thr Val Asn Ile Glu Cys Leu Ala Ser Glu Asp Ile Tyr Ser Asp
            20                  25                  30

Leu Ala Trp Tyr Gln Gln Lys Pro Gly Lys Ser Pro Gln Leu Leu Ile
        35                  40                  45

Tyr Ser Thr Asn Thr Leu Gln Asn Gly Val Pro Ser Arg Phe Ser Gly
50                  55                  60

Ser Gly Ser Gly Thr Gln Tyr Ser Leu Lys Ile Asn Ser Leu Gln Ser
65                  70                  75                  80

Glu Asp Val Ala Thr Tyr Phe Cys Gln Gln Asn Asn Asn Tyr Pro Tyr
                85                  90                  95

Thr Phe Gly Ala Gly Thr Lys Leu Glu Leu Lys
            100                 105

<210> SEQ ID NO 156
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 156

Gln Val Val Leu Thr Gln Pro Lys Ser Val Ser Thr Ser Leu Lys Ser
1               5                   10                  15

Thr Val Lys Leu Ser Cys Lys Leu Asn Ser Gly Asn Ile Gly Ser Tyr
            20                  25                  30

Tyr Val His Trp Tyr Gln Gln His Ala Gly Arg Ser Pro Thr Thr Met
        35                  40                  45

Ile Tyr Arg Asp Asp Lys Arg Pro Asp Gly Val Pro Asp Arg Phe Ser
50                  55                  60

Gly Ser Ile Asp Ser Ser Asn Ser Ala Phe Leu Thr Ile Asn Asn Asn
65                  70                  75                  80

Val Gln Thr Glu Asp Asp Ala Ile Tyr Phe Cys His Ser Tyr Asp Ser
                85                  90                  95

Thr Ile Thr Pro Val Phe Gly Gly Gly Thr Lys Leu Thr Val Leu
            100                 105                 110

<210> SEQ ID NO 157
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 157

Asp Val Val Leu Thr Gln Thr Pro Ser Ile Leu Ser Ala Thr Ile Gly
1               5                   10                  15
```

Gln Ser Val Ser Ile Ser Cys Arg Ser Ser Gln Ser Leu Leu Asp Ser
                    20                  25                  30

Asp Gly Asn Thr Tyr Leu Tyr Trp Phe Leu Gln Arg Pro Gly Gln Ser
            35                  40                  45

Pro Gln Arg Leu Ile Tyr Leu Val Ser Asn Leu Gly Ser Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Ile Tyr Tyr Cys Met Gln Pro
                85                  90                  95

Thr His Ala Pro Tyr Thr Phe Gly Ala Gly Thr Lys Leu Glu Leu Lys
            100                 105                 110

<210> SEQ ID NO 158
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 158

Gln Ala Val Leu Thr Gln Pro Asn Ser Val Ser Thr Ser Leu Gly Ser
1               5                   10                  15

Thr Val Lys Leu Ser Cys Thr Ile Thr Ser Gly Asn Ile Glu Asp Asn
                20                  25                  30

Phe Val His Trp Tyr Gln His Tyr Glu Gly Arg Ser Pro Thr Thr Met
            35                  40                  45

Ile His Asn Asp Asp Lys Arg Pro Asp Gly Val Pro Asp Arg Phe Ser
    50                  55                  60

Gly Ser Ile Asp Ser Ser Ser Asn Ser Ala Phe Leu Thr Ile Asn Asn
65                  70                  75                  80

Val Glu Ile Glu Asp Glu Ala Ile Tyr Phe Cys His Ser Tyr Val Ser
                85                  90                  95

Ser Ile Asn Ile Phe Gly Gly Gly Thr Lys Leu Thr Val Leu
            100                 105                 110

<210> SEQ ID NO 159
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 159

Asn Val Met Leu Thr Gln Pro His Ser Val Ser Glu Ser Pro Gly Lys
1               5                   10                  15

Thr Val Thr Ile Ser Cys Lys Leu Asn Ser Gly Asn Ile Gly Ser Tyr
                20                  25                  30

Tyr Val His Trp Tyr Gln Gln Arg Pro Gly Ser Ser Pro Thr Thr Met
            35                  40                  45

Ile Tyr Arg Asp Asp Lys Arg Pro Asp Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys His Ser Tyr Asp Ser

```
                    85                  90                  95

Thr Ile Thr Pro Val Phe Gly Gly Gly Thr Lys Leu Thr Val Leu
                100                 105                 110

<210> SEQ ID NO 160
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 160

Gln Val Val Leu Thr Gln Pro Pro Ser Ala Ser Gly Thr Pro Gly Gln
1               5                   10                  15

Arg Val Thr Ile Ser Cys Lys Leu Asn Ser Gly Asn Ile Gly Ser Tyr
            20                  25                  30

Tyr Val His Trp Tyr Gln Gln Leu Pro Gly Thr Ala Pro Lys Thr Met
        35                  40                  45

Ile Tyr Arg Asp Asp Lys Arg Pro Asp Gly Val Pro Asp Arg Phe Ser
    50                  55                  60

Gly Ser Ser Ser Ser Asn Ser Ala Ser Leu Ala Ile Ser Gly Leu Gln
65                  70                  75                  80

Ser Glu Asp Glu Ala Asp Tyr Tyr Cys His Ser Tyr Asp Ser Thr Ile
                85                  90                  95

Thr Pro Val Phe Gly Gly Gly Thr Lys Leu Thr Val Leu
                100                 105

<210> SEQ ID NO 161
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 161

Ser Val Glu Leu Thr Gln Pro Pro Ser Val Ser Val Ser Pro Gly Gln
1               5                   10                  15

Thr Ala Arg Ile Thr Cys Lys Leu Asn Ser Gly Asn Ile Gly Ser Tyr
            20                  25                  30

Tyr Val His Trp Tyr Gln Gln Lys Pro Gly Gln Ala Pro Val Thr Met
        35                  40                  45

Ile Tyr Arg Asp Asp Lys Arg Pro Asp Gly Ile Pro Glu Arg Phe Ser
    50                  55                  60

Gly Ser Ser Asp Ser Ser Ser Asn Ser Ala Phe Leu Thr Ile Ser Gly
65                  70                  75                  80

Val Gln Ala Glu Asp Glu Ala Asp Tyr Tyr Cys His Ser Tyr Asp Ser
                85                  90                  95

Thr Ile Thr Pro Val Phe Gly Gly Gly Thr Lys Leu Thr Val Leu
                100                 105                 110

<210> SEQ ID NO 162
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
```

<400> SEQUENCE: 162

Glu Val Val Leu Thr Gln Pro Pro Ser Leu Ser Ala Ser Pro Gly Ala
1               5                   10                  15

Ser Ala Arg Leu Thr Cys Lys Leu Asn Ser Gly Asn Ile Gly Ser Tyr
            20                  25                  30

Tyr Val His Trp Tyr Gln Gln Lys Pro Gly Ser Pro Pro Arg Thr Met
        35                  40                  45

Ile Tyr Arg Asp Asp Lys Arg Pro Asp Gly Val Pro Ser Arg Phe Ser
    50                  55                  60

Gly Ser Lys Asp Ser Ser Asn Ser Ala Phe Leu Leu Ile Ser Gly
65                  70                  75                  80

Leu Gln Ser Glu Asp Glu Ala Asp Tyr Tyr Cys His Ser Tyr Asp Ser
                85                  90                  95

Thr Ile Thr Pro Val Phe Gly Gly Gly Thr Lys Leu Thr Val Leu
            100                 105                 110

<210> SEQ ID NO 163
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 163

Asp Val Gln Leu Thr Gln Ser Pro Ser Ser Leu Ser Ala Ser Val Gly
1               5                   10                  15

Asp Arg Val Thr Ile Thr Cys Lys Leu Asn Ser Gly Asn Ile Gly Ser
            20                  25                  30

Tyr Tyr Val His Trp Tyr Gln Gln Lys Pro Gly Lys Ala Pro Lys Thr
        35                  40                  45

Met Ile Tyr Arg Asp Asp Lys Arg Pro Asp Gly Val Pro Ser Arg Phe
    50                  55                  60

Ser Gly Ser Gly Asp Ser Ser Asn Ser Ala Phe Leu Thr Ile Ser
65                  70                  75                  80

Ser Leu Gln Pro Glu Asp Phe Ala Thr Tyr Tyr Cys His Ser Tyr Asp
                85                  90                  95

Ser Thr Ile Thr Pro Val Phe Gly Gln Gly Thr Lys Val Glu Ile Lys
            100                 105                 110

<210> SEQ ID NO 164
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 164

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Asn Thr Tyr Leu Tyr Trp Phe Gln Gln Arg Pro Gly Gln Ser
        35                  40                  45

-continued

Pro Arg Leu Ile Tyr Leu Val Ser Asn Leu Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Pro
                85                  90                  95

Thr His Ala Pro Tyr Thr Phe Gly Gln Gly Thr Lys Leu Glu Ile Lys
            100                 105                 110

<210> SEQ ID NO 165
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

Asp Val Gln Leu Thr Gln Ser Pro Ser Ser Leu Ser Ala Ser Val Gly
1               5                   10                  15

Asp Arg Val Thr Ile Thr Cys Arg Ser Ser Gln Ser Leu Leu Asp Ser
                20                  25                  30

Asp Gly Asn Thr Tyr Leu Tyr Trp Phe Gln Gln Lys Pro Gly Lys Ala
            35                  40                  45

Pro Lys Arg Leu Ile Tyr Leu Val Ser Asn Leu Gly Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Pro
                85                  90                  95

Thr His Ala Pro Tyr Thr Phe Gly Gln Gly Thr Lys Val Glu Ile Lys
            100                 105                 110

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 171

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Asp Ser
            20                  25                  30

Asp Gly Ile Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Leu Tyr Tyr Cys Phe Gln Val
                85                  90                  95

Ser His Val Pro Trp Thr Phe Gly Gly Gly Thr Lys Leu Glu Ile Lys
            100                 105                 110
```

<210> SEQ ID NO 172

<400> SEQUENCE: 172

000

<210> SEQ ID NO 173
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 173

```
Asp Ile Val Ile Thr Gln Asp Glu Leu Ser Asn Pro Val Thr Ser Gly
1               5                   10                  15

Glu Ser Ala Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60

Asp Arg Phe Thr Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Pro
                85                  90                  95

Val Glu Tyr Pro Tyr Thr Phe Gly Gly Gly Thr Lys Leu Glu Ile Lys
            100                 105                 110
```

<210> SEQ ID NO 174

<400> SEQUENCE: 174

000

<210> SEQ ID NO 175
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 175

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro His Thr Phe Gly Gly Gly Thr Lys Leu Glu Ile Lys
            100                 105                 110

<210> SEQ ID NO 176
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 176

Asp Val Val Met Thr Gln Thr Pro Leu Thr Leu Ser Val Thr Ile Gly
1               5                   10                  15

Gln Ala Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro His Thr Phe Gly Gly Gly Thr Lys Leu Glu Ile Lys
            100                 105                 110

<210> SEQ ID NO 177

<400> SEQUENCE: 177

000

<210> SEQ ID NO 178

<400> SEQUENCE: 178

000

<210> SEQ ID NO 179
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 179

Asp Ile Gln Met Thr Gln Thr Thr Ser Ser Leu Ser Ala Ser Leu Gly
1               5                   10                  15

Asp Arg Ile Thr Ile Ser Cys Arg Ala Ser Gln Asp Ile Ser Asn Tyr
            20                  25                  30

Leu Asn Trp Tyr Gln Arg Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Arg Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 180
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 180

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile His Asn Tyr
            20                  25                  30

Ile Ser Trp Tyr Gln His Lys Pro Gly Lys Gly Pro Arg Leu Val Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Tyr Thr
                85                  90                  95

Phe Gly Gly Gly Thr Lys Leu Glu Ile Lys
            100                 105

<210> SEQ ID NO 181

<400> SEQUENCE: 181

000

<210> SEQ ID NO 182

```
<400> SEQUENCE: 182
000

<210> SEQ ID NO 183
<400> SEQUENCE: 183
000

<210> SEQ ID NO 184
<400> SEQUENCE: 184
000

<210> SEQ ID NO 185
<400> SEQUENCE: 185
000

<210> SEQ ID NO 186
<400> SEQUENCE: 186
000

<210> SEQ ID NO 187
<400> SEQUENCE: 187
000

<210> SEQ ID NO 188
<400> SEQUENCE: 188
000

<210> SEQ ID NO 189
<400> SEQUENCE: 189
000

<210> SEQ ID NO 190
<400> SEQUENCE: 190
000

<210> SEQ ID NO 191
<400> SEQUENCE: 191
000

<210> SEQ ID NO 192
<400> SEQUENCE: 192
000

<210> SEQ ID NO 193
<400> SEQUENCE: 193
```

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Gly Phe Thr Phe Ser Ser Tyr Gly Met Ser
1               5                   10

<210> SEQ ID NO 202

<400> SEQUENCE: 202

000

<210> SEQ ID NO 203
<211> LENGTH: 10
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic peptide"

<400> SEQUENCE: 203

Gly Phe Thr Phe Ser Ser Phe Gly Met His
1               5                   10

<210> SEQ ID NO 204

<400> SEQUENCE: 204

000

<210> SEQ ID NO 205
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Gly Phe Asn Ile Lys Asp Tyr Tyr Met His
1               5                   10

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Gly Phe Ser Leu Thr Ser Tyr Gly Val His
1               5                   10

<210> SEQ ID NO 210
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Gly Tyr Thr Phe Thr Thr Tyr Gly Met Ser
1               5                   10

<210> SEQ ID NO 211
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Ala Ile Ile Ser Gly Gly Ser Tyr Thr Tyr Tyr Pro Asp Ser Val Lys
1               5                   10                  15

Gly

<210> SEQ ID NO 212

<400> SEQUENCE: 212

000

<210> SEQ ID NO 213
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Tyr Ile Ser Ser Gly Ser Ser Thr Ile Tyr Tyr Ala Asp Thr Leu Lys
1               5                   10                  15

Gly

<210> SEQ ID NO 214

<400> SEQUENCE: 214

000

<210> SEQ ID NO 215
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Arg Ile Asp Pro Glu Asp Gly Asp Thr Glu Tyr Val Pro Lys Phe Gln
1               5                   10                  15

Gly

<210> SEQ ID NO 216
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

```
Arg Ile Asp Pro Glu Asp Gly Asp Thr Glu Tyr Ala Pro Lys Phe Gln
1               5                   10                  15
Gly

<210> SEQ ID NO 217

<400> SEQUENCE: 217

000

<210> SEQ ID NO 218

<400> SEQUENCE: 218

000

<210> SEQ ID NO 219
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Met Ile Trp Ser Gly Gly Ser Thr Asp Tyr Asn Ala Ala Phe Ile Ser
1               5                   10                  15

<210> SEQ ID NO 220
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Trp Ile Asn Thr Tyr Ser Gly Val Pro Thr Tyr Ala Asp Asp Phe Lys
1               5                   10                  15
Gly

<210> SEQ ID NO 221
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

His Gly Gly Tyr Asp Gly Asn Tyr Asp Tyr Tyr Ala Met Asp Tyr
1               5                   10                  15

<210> SEQ ID NO 222

<400> SEQUENCE: 222

000

<210> SEQ ID NO 223
<211> LENGTH: 5
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 223

Asp Trp Val Asp Tyr
1               5

<210> SEQ ID NO 224

<400> SEQUENCE: 224

000

<210> SEQ ID NO 225
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Tyr Ser Asn Tyr Val Tyr Trp Tyr Phe Asp Val
1               5                   10

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Tyr Gly Gly Phe Tyr Glu Thr Met Asp Tyr
1               5                   10

<210> SEQ ID NO 230
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230
```

```
Gly Asn Asp Gly Asn Tyr Tyr Gly Trp Phe Ala His
1               5                   10
```

<210> SEQ ID NO 231
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

```
Arg Ser Ser Gln Ser Ile Val Asp Ser Asp Gly Ile Thr Tyr Leu Glu
1               5                   10                  15
```

<210> SEQ ID NO 232

<400> SEQUENCE: 232

000

<210> SEQ ID NO 233
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

```
Arg Ser Ser Lys Ser Leu Leu Tyr Lys Asp Gly Lys Thr Tyr Leu Asn
1               5                   10                  15
```

<210> SEQ ID NO 234

<400> SEQUENCE: 234

000

<210> SEQ ID NO 235
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

```
Lys Ser Ser Gln Ser Leu Leu Asp Ser Asp Gly Lys Thr Tyr Leu Asn
1               5                   10                  15
```

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Arg Ala Ser Gln Asp Ile Ser Asn Tyr Leu Asn
1               5                   10

<210> SEQ ID NO 240
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Lys Ala Ser Gln Asp Ile His Asn Tyr Ile Ser
1               5                   10

<210> SEQ ID NO 241
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Lys Val Ser Asn Arg Phe Ser
1               5

<210> SEQ ID NO 242

<400> SEQUENCE: 242

000

<210> SEQ ID NO 243
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 243

Leu Met Ser Thr Arg Ala Ser
1               5

<210> SEQ ID NO 244

<400> SEQUENCE: 244

000

```
<210> SEQ ID NO 245
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 245

Leu Val Ser Lys Leu Asp Ser
1               5

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

Tyr Thr Ser Arg Leu His Ser
1               5

<210> SEQ ID NO 250
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

Tyr Thr Ser Thr Leu Gln Pro
1               5

<210> SEQ ID NO 251
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Phe Gln Val Ser His Val Pro Trp Thr
```

1               5

<210> SEQ ID NO 252

<400> SEQUENCE: 252

000

<210> SEQ ID NO 253
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Gln Gln Pro Val Glu Tyr Pro Tyr Thr
1               5

<210> SEQ ID NO 254

<400> SEQUENCE: 254

000

<210> SEQ ID NO 255
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

Trp Gln Gly Thr His Phe Pro His Thr
1               5

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 259

```
Gln Gln Gly Asn Thr Leu Pro Tyr Thr
1               5
```

<210> SEQ ID NO 260
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 260

```
Leu Gln Tyr Asp Asn Leu Tyr Thr
1               5
```

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270
<400> SEQUENCE: 270
000

<210> SEQ ID NO 271
<400> SEQUENCE: 271
000

<210> SEQ ID NO 272
<400> SEQUENCE: 272
000

<210> SEQ ID NO 273
<400> SEQUENCE: 273
000

<210> SEQ ID NO 274
<400> SEQUENCE: 274
000

<210> SEQ ID NO 275
<400> SEQUENCE: 275
000

<210> SEQ ID NO 276
<400> SEQUENCE: 276
000

<210> SEQ ID NO 277
<400> SEQUENCE: 277
000

<210> SEQ ID NO 278
<400> SEQUENCE: 278
000

<210> SEQ ID NO 279
<400> SEQUENCE: 279
000

<210> SEQ ID NO 280
<400> SEQUENCE: 280
000

-continued

<210> SEQ ID NO 281
<400> SEQUENCE: 281
000

<210> SEQ ID NO 282
<400> SEQUENCE: 282
000

<210> SEQ ID NO 283
<400> SEQUENCE: 283
000

<210> SEQ ID NO 284
<400> SEQUENCE: 284
000

<210> SEQ ID NO 285
<400> SEQUENCE: 285
000

<210> SEQ ID NO 286
<400> SEQUENCE: 286
000

<210> SEQ ID NO 287
<400> SEQUENCE: 287
000

<210> SEQ ID NO 288
<400> SEQUENCE: 288
000

<210> SEQ ID NO 289
<400> SEQUENCE: 289
000

<210> SEQ ID NO 290
<400> SEQUENCE: 290
000

<210> SEQ ID NO 291
<400> SEQUENCE: 291
000

<210> SEQ ID NO 292

<400> SEQUENCE: 292

000

<210> SEQ ID NO 293
<400> SEQUENCE: 293

000

<210> SEQ ID NO 294
<400> SEQUENCE: 294

000

<210> SEQ ID NO 295
<400> SEQUENCE: 295

000

<210> SEQ ID NO 296
<400> SEQUENCE: 296

000

<210> SEQ ID NO 297
<400> SEQUENCE: 297

000

<210> SEQ ID NO 298
<400> SEQUENCE: 298

000

<210> SEQ ID NO 299
<400> SEQUENCE: 299

000

<210> SEQ ID NO 300
<400> SEQUENCE: 300

000

<210> SEQ ID NO 301
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 301

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

-continued

```
Tyr Trp Ser Trp Ile Arg Gln Ser Pro Glu Lys Gly Leu Glu Trp Ile
             35                  40                  45
Gly Glu Ile Asn His Gly Gly Tyr Val Thr Tyr Asn Pro Ser Leu Glu
 50                  55                  60
Ser Arg Val Thr Ile Ser Val Asp Thr Ser Lys Asn Gln Phe Ser Leu
 65                  70                  75                  80
Lys Leu Ser Ser Val Thr Ala Ala Asp Thr Ala Val Tyr Tyr Cys Ala
                 85                  90                  95
Arg Asp Tyr Gly Pro Gly Asn Tyr Asp Trp Tyr Phe Asp Leu Trp Gly
                100                 105                 110
Arg Gly Thr Leu Val Thr Val Ser Ser Ala Ser Thr Lys Gly Pro Ser
            115                 120                 125
Val Phe Pro Leu Ala Pro Cys Ser Arg Ser Thr Ser Glu Ser Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
        195                 200                 205
Lys Pro Ser Asn Thr Lys Val Asp Lys Arg Val Glu Ser Lys Tyr Gly
    210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Asp Val Ser Gln Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
            420                 425                 430
Leu His Asn His Tyr Thr Gln Lys Ser Leu Ser Leu Ser Leu Gly Lys
        435                 440                 445
```

```
<210> SEQ ID NO 302
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 302

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 303
<211> LENGTH: 442
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 303

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80
```

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 304
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 304

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 310

Glu Val Gln Leu Val Gln Ser Gly Ala Glu Val Lys Pro Gly Ser
1               5                   10                  15

Ser Val Lys Val Ser Cys Lys Ala Ser Gly Tyr Thr Phe Thr Ser Tyr
            20                  25                  30

Tyr Ile Tyr Trp Val Arg Gln Ala Pro Gly Gln Gly Leu Glu Trp Ile
        35                  40                  45

Gly Asn Ile Trp Pro Gly Asn Gly Gly Thr Phe Tyr Gly Glu Lys Phe
    50                  55                  60

Met Gly Arg Ala Thr Phe Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Pro Asp Tyr Ser Gly Asp Asp Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

```
Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 311
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 311

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Tyr Ile Tyr Trp Val Arg Gln Ala Pro Gly Gln Gly Leu Glu Trp Ile
        35                  40                  45

Gly Asn Ile Trp Pro Gly Asn Gly Gly Thr Phe Tyr Gly Glu Lys Phe
    50                  55                  60

Met Gly Arg Ala Thr Phe Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Pro Asp Tyr Ser Gly Asp Asp Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
```

```
                    245                 250                 255
Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 312
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 312

Glu Val Gln Leu Val Gln Ser Gly Ala Glu Val Lys Lys Pro Gly Ser
1               5                   10                  15

Ser Val Lys Val Ser Cys Lys Ala Ser Asp Tyr Thr Phe Asn Asp Tyr
            20                  25                  30

Trp Val Ser Trp Val Arg Gln Ala Pro Gly Gln Gly Leu Glu Trp Ile
        35                  40                  45

Gly Glu Ile Tyr Pro Asn Ser Gly Ala Thr Asn Phe Asn Gly Lys Phe
    50                  55                  60

Arg Gly Arg Ala Thr Leu Thr Val Asp Asn Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Tyr Thr Arg Asp Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 313
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 313

Glu Val Gln Leu Val Gln Ser Gly Ala Glu Val Lys Lys Pro Gly Ser
1               5                   10                  15

Ser Val Lys Val Ser Cys Lys Ala Ser Asp Tyr Thr Phe Asn Asp Tyr
            20                  25                  30

Trp Val Ser Trp Val Arg Gln Ala Pro Gly Gln Gly Leu Glu Trp Ile
            35                  40                  45

-continued

```
Gly Glu Ile Tyr Pro Asn Ser Gly Ala Thr Asn Phe Asn Gly Lys Phe
 50                  55                  60

Arg Gly Arg Ala Thr Leu Thr Val Asp Asn Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Glu Tyr Thr Arg Asp Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 314
<211> LENGTH: 217
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 314

Asn Val Met Leu Thr Gln Pro His Ser Val Ser Glu Ser Pro Gly Lys
1               5                   10                  15

Thr Val Thr Ile Ser Cys Lys Leu Asn Ser Gly Asn Ile Gly Ser Tyr
            20                  25                  30

Tyr Val His Trp Tyr Gln Gln Arg Pro Gly Ser Ser Pro Thr Thr Met
        35                  40                  45

Ile Tyr Arg Asp Asp Lys Arg Pro Asp Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys His Ser Tyr Asp Ser
                85                  90                  95

Thr Ile Thr Pro Val Phe Gly Gly Thr Lys Leu Thr Val Leu Gly
            100                 105                 110

Gln Pro Lys Ala Ala Pro Ser Val Thr Leu Phe Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 315
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 315

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Asn Thr Tyr Leu Tyr Trp Phe Gln Gln Arg Pro Gly Gln Ser
        35                  40                  45

Pro Arg Arg Leu Ile Tyr Leu Val Ser Asn Leu Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Pro
                85                  90                  95
```

```
Thr His Ala Pro Tyr Thr Phe Gly Gln Gly Thr Lys Leu Glu Ile Lys
        100             105             110

Arg Thr Val Ala Ala Pro Ser Val Phe Ile Phe Pro Pro Ser Asp Glu
        115             120             125

Gln Leu Lys Ser Gly Thr Ala Ser Val Val Cys Leu Leu Asn Asn Phe
        130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
                165             170             175

Thr Tyr Ser Leu Ser Ser Thr Leu Thr Leu Ser Lys Ala Asp Tyr Glu
            180             185             190

Lys His Lys Val Tyr Ala Cys Glu Val Thr His Gln Gly Leu Ser Ser
        195             200             205

Pro Val Thr Lys Ser Phe Asn Arg Gly Glu Cys
    210             215
```

ANTI-4-1BB ANTIBODIES AND THEIR USES

1. CROSS REFERENCE TO RELATED APPLICATIONS

This application is a National Stage of International Application No. PCT/US2017/034687, filed May 26, 2017, which claims the benefit under 35 U.S.C. § 119 (e) of U.S. Provisional Application No. 62/342,497, filed May 27, 2016, the contents of all of which are incorporated herein in their entireties by reference thereto.

2. SEQUENCE LISTING

The instant application contains a Sequence Listing which has been submitted electronically in ASCII format and is hereby incorporated by reference in its entirety. Said ASCII copy, created on May 19, 2017, is named 381493-287WO_SL.txt and is 115,221 bytes in size.

3. TECHNICAL FIELD

The present application pertains to, among other things, novel anti-4-1BB antibodies, compositions including the new antibodies, nucleic acids encoding the antibodies, and methods of making and using the same.

4. BACKGROUND

Cancer therapies comprise a wide range of therapeutic approaches, including surgery, radiation, and chemotherapy. While the various approaches allow a broad selection of treatments to be available to the medical practitioner to treat the cancer, existing therapeutics suffer from a number of disadvantages, such as a lack of selectivity of targeting cancer cells over normal, healthy cells, and the development of resistance by the cancer to the treatment.

Recent approaches based on targeted therapeutics, which interfere with cellular processes of cancer cells preferentially over normal cells, have led to chemotherapeutic regimens with fewer side effects as compared to non-targeted therapies such as radiation treatment.

Cancer immunotherapy, in particular the development of agents that activate T cells of the host's immune system to prevent the proliferation of or kill cancer cells, has emerged as a promising therapeutic approach to complement existing standards of care. See, e.g., Miller, et al. Cancer Cell, 27, 439-449 (2015). Such immunotherapy approaches include the development of antibodies used to modulate the immune system to kill cancer cells. For example, anti-PD-1 blocking antibodies pembrolizumab (Keytruda®) and nivolumab (Opdivo®) have been approved in the US and the European Union to treat diseases such as unresectable or metastatic melanoma and metastatic non-small cell lung cancer. Efforts to inhibit immunosuppressive proteins such as CTLA-4 have led to the development and clinical evaluation of anti-CTLA-4 antibodies, such as tremelimumab and ipilimumab (Yervoy®).

There remains a need for alternative approaches and additional cancer treatments to complement existing therapeutic standards of care.

5. SUMMARY

Human 4-1BB (SEQ ID NO:1) is a tumor necrosis factor (TNF) receptor superfamily member (TNF superfamily member 9) expressed on number of immune cells including activated T cells, B cells, dendritic cells (DC), activated natural killer (NK) cells, as well as nonimmune cells, such as activated endothelial cells. When activated by human 4-1BB ligand (SEQ ID NO:2), human 4-1BB costimulates T cells, thereby providing an effective T cell immune response and generating immune memory by inducing multiple signaling cascades. Agonistic 4-1BB agents, such as anti-4-1BB antibodies, can induce an activated immune system to kill tumor cells, and thus lead to effective therapeutic treatment of solid tumors (See Bartkowiak and Curran 2015, Frontiers in Oncology, 5: 117).

The present disclosure provides anti-4-1BB antibodies and binding fragments thereof that specifically bind to human 4-1BB. The amino acid sequences of exemplary CDRs, as well as the amino acid sequence of the $V_H$ and $V_L$ regions of the heavy and light chains of exemplary anti-4-1BB antibodies and/or binding fragments are provided in the Detailed Description below.

In some embodiments, an anti-4-1BB antibody described herein does not compete with human 4-1BB ligand (4-1BBL), binds both mouse and cynomolgus 4-1BB, and activates human 4-1BB only in the presence of a receptor crosslinker, such as a Fc receptor crosslinker expressed on cells.

The anti-4-1BB antibodies may include modifications and/or mutations that alter the properties of the antibodies, such as increase half-life, increase or decrease ADCC, etc., as is known in the art.

Nucleic acids comprising nucleotide sequences encoding the anti-4-1BB antibodies of the disclosure are provided herein, as are vectors comprising nucleic acids. Additionally, prokaryotic and eukaryotic host cells transformed with a vector comprising a nucleotide sequence encoding a disclosed anti-4-1BB antibody are provided herein, as well as eukaryotic (such as mammalian) host cells engineered to express the nucleotide sequences. Methods of producing antibodies, by culturing host cells and recovering the antibodies are also provided, and discussed further in the Detailed Description below.

In another aspect, the present disclosure provides compositions including the anti-4-1BB antibodies described herein. The compositions generally comprise one or more anti-4-1BB antibodies as described herein, and/or salts thereof, and one or more excipients, carriers or diluents.

The present disclosure provides methods of treating subjects, such as human subjects, diagnosed with a solid tumor with an anti-4-1BB antibody. The method generally involves administering to the subject an amount of an anti-4-1BB antibody described herein effective to provide therapeutic benefit. The subject may be diagnosed with any one of a number of solid tumors that may be newly diagnosed, relapsed, or relapsed and refractory. An anti-4-1BB antibody is typically administered as an intravenous infusion twice a week, once a week, once every two weeks, once every three weeks, once every four weeks, once every five weeks, once every six weeks, once every seven weeks, or once every eight weeks.

The anti-4-1BB antibodies may be administered as single therapeutic agents (monotherapy) or adjunctive to or with other therapeutic agents typically, but not necessarily, those used for the treatment of a solid tumor. Therapeutic agents typically will be used at their approved dose, route of administration, and frequency of administration, but may be used at lower dosages.

The anti-4-1BB antibodies may be administered via a variety of routes or modes of administration, including but not limited to, intravenous infusion and/or injection, intratumoral injection, and subcutaneous injection. The amount administered will depend upon the route of administration, the dosing schedule, the type of cancer being treated, the stage of the cancer being treated, and other parameters such as the age and weight of the patient, as is well known in the art. Specific exemplary dosing schedules expected to provide therapeutic benefit are provided in the Detailed Description.

6. BRIEF DESCRIPTION OF THE FIGURES

FIG. 1A shows the amino acid sequences of 4-1BB receptor in human (SEQ ID NO:1), mouse (SEQ ID NO:3), cynomolgus monkey (SEQ ID NO:4), and rat (SEQ ID NO:5); FIG. 1B shows the sequence for human 4-1BB ligand (SEQ ID NO:2).

FIGS. 2A-2F provide amino acid sequences for $V_H$ and $V_L$ of exemplary anti-4-1BB antibodies. FIG. 2A shows amino acid sequences for $V_H$ and $V_L$ of rat anti-4-1BB antibodies TABBY101 through TABBY104; FIG. 2B shows amino acid sequences for $V_H$ and $V_L$ of rat anti-4-1BB antibodies TABBY105 through TABBY108; FIG. 2C shows amino acid sequences for $V_H$ and $V_L$ of exemplary murine anti-4-1BB antibodies; FIG. 2D shows amino acid sequences for $V_H$ and $V_L$ of murine anti-4-1BB antibodies TABBY9 and TABBY10; FIG. 2E shows the amino acid sequences for $V_H$ and $V_L$ of humanized anti-4-1BB antibodies derived from TABBY106; FIG. 2F shows the amino acid sequences for $V_H$ and $V_L$ of humanized anti-4-1BB antibodies derived from TABBY107.

FIG. 3 shows effects of exemplary chimeric anti-4-1BB antibodies TABBY106-hIgG$_4$ or TABBY107-hIgG$_4$ on human CD8+ T cell proliferation co-cultured with CHOK1 with or without Fcγ receptor expression as measured by $^3$H-thymidine incorporation (CPM).

FIGS. 4A-4C show the effects of different human constant regions IgG$_1$, IgG$_1$ with V273E substitution, IgG$_2$, or IgG$_4$, in exemplary chimeric anti-4-1BB antibodies TABBY106 or TABBY107 on T-cell stimulation as measured by IFN-γ secretion in pg/mL; FIG. 4A shows data for chimeric TABBY106 antibodies; FIG. 4B shows data for chimeric TABBY107 antibodies; FIG. 4C shows data for humanized antibodies hu106-1-hIgG1 V273E and hu107-1-hIgG1 V273E, and reference antibodies.

7. DETAILED DESCRIPTION

Figure 3:
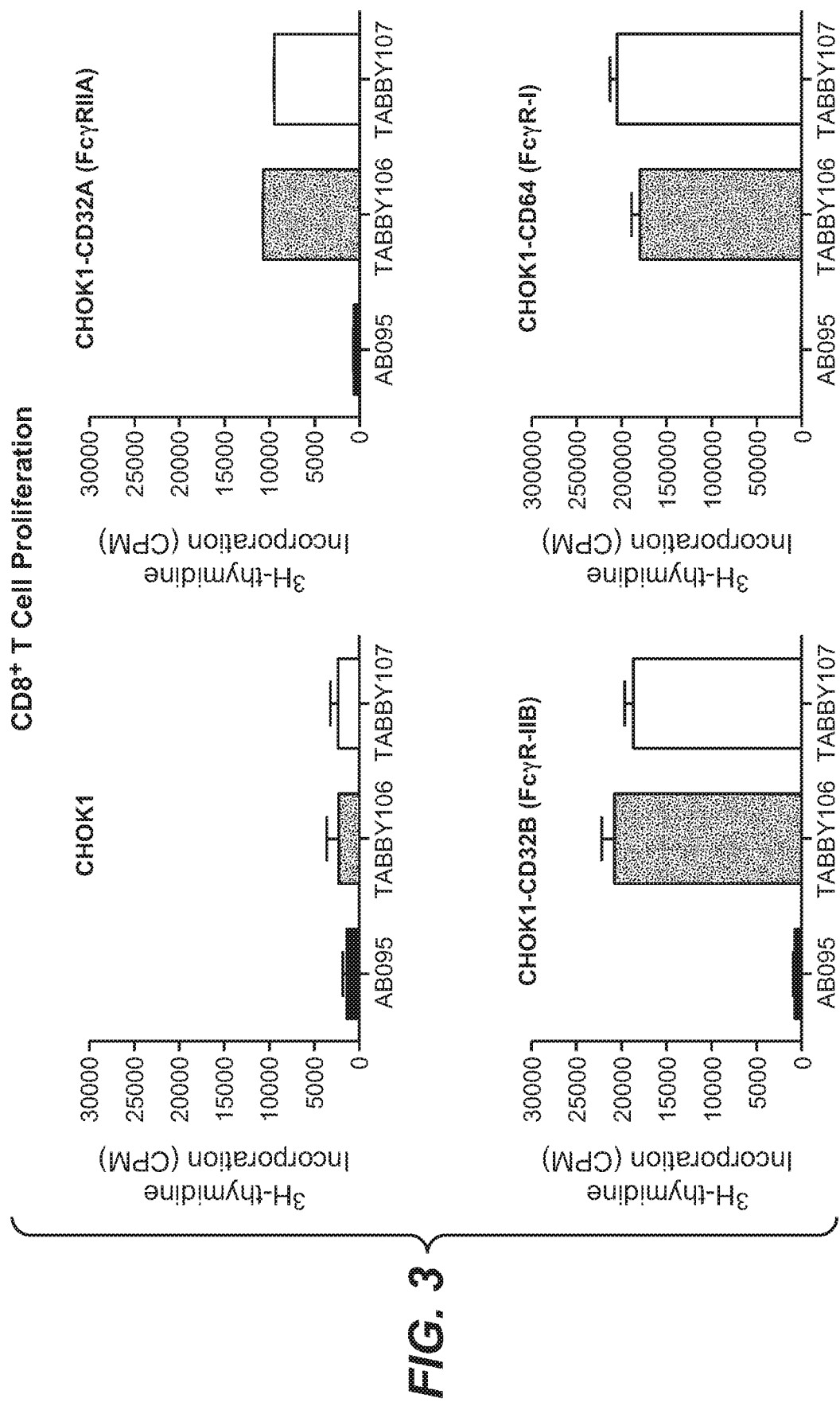

The present disclosure concerns antibodies and fragments that specifically bind human 4-1BB, compositions comprising the antibodies, polynucleotides encoding anti-4-1BB antibodies, host cells capable of producing the antibodies, methods and compositions useful for making the antibodies, and various methods of using the same.

As will be appreciated by skilled artisans, antibodies are "modular" in nature. Throughout the disclosure, various specific embodiments of the various "modules" composing the antibodies are described. As specific non-limiting examples, various specific embodiments of $V_H$ CDRs, $V_H$ chains, $V_L$ CDRs and $V_L$ chains are described. It is intended that all of the specific embodiments may be combined with each other as though each specific combination were explicitly described individually.

7.1. Abbreviations

The antibodies, binding fragments, ADCs and polynucleotides described herein are, in many embodiments, described by way of their respective polypeptide or polynucleotide sequences. Unless indicated otherwise, polypeptide sequences are provided in N→C orientation; polynucleotide sequences in 5'→3' orientation. For polypeptide sequences, the conventional three or one-letter abbreviations for the genetically encoded amino acids may be used, as noted in TABLE 1, below.

TABLE 1

Encoded Amino Acid Abbreviations

| Amino Acid | Three Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Certain sequences are defined by structural formulae specifying amino acid residues belonging to certain classes (e.g., aliphatic, hydrophobic, etc.). The various classes to which the genetically encoded amino acids belong as used herein are noted in TABLE 2, below. Some amino acids may belong to more than one class. Cysteine, which contains a sulfhydryl group, and proline, which is conformationally constrained, are not assigned classes.

TABLE 2

Encoded Amino Acid Classes

| Class | Amino Acids |
| --- | --- |
| Aliphatic | A, I, L, V |
| Aromatic | F, Y, W |
| Non-Polar | M, A, I, L, V |
| Polar | N, Q, S, T |
| Basic | H, K, R |
| Acidic | D, E |
| Small | A, G |

The abbreviations used for the various exemplary antibodies disclosed herein are provided in TABLE 3, below:

TABLE 3

Antibody Abbreviations

| Name/Description | Abbreviation | $V_H$ Sequence (FIGS. 2A-2D) | $V_L$ Sequence (FIGS. 2A-2D) |
| --- | --- | --- | --- |
| Rat TABBY101 with rat IgG1 constant | TABBY101-rIgG$_1$ | TABBY101V$_H$ SEQ ID NO: 101 | TABBY101V$_L$ SEQ ID NO: 151 |
| Rat TABBY102 with rat IgG1 constant | TABBY102-rIgGp$_1$ | TABBY102V$_H$ SEQ ID NO: 102 | TABBY102V$_L$ SEQ ID NO: 152 |
| Rat TABBY103 with rat IgG1 constant | TABBY103-rIgG$_1$ | TABBY103V$_H$ SEQ ID NO: 103 | TABBY103V$_L$ SEQ ID NO: 153 |
| Rat TABBY104 with rat IgG1 constant | TABBY104-rIgG$_1$ | TABBY104V$_H$ SEQ ID NO: 104 | TABBY104V$_L$ SEQ ID NO: 154 |
| Rat TABBY105 with rat IgG2a constant | TABBY105-rIgG$_{2a}$ | TABBY105V$_H$ SEQ ID NO: 105 | TABBY105V$_L$ SEQ ID NO: 155 |
| Rat TABBY106 with rat IgG1 constant | TABBY106-rIgG$_1$ | TABBY106V$_H$ SEQ ID NO: 106 | TABBY106V$_L$ SEQ ID NO: 156 |
| Rat TABBY107 with rat IgG1 constant | TABBY107-rIgG$_1$ | TABBY107V$_H$ SEQ ID NO: 107 | TABBY107V$_L$ SEQ ID NO: 157 |
| Rat TABBY108 with rat IgG1 constant | TABBY108-rIgG$_1$ | TABBY108V$_H$ SEQ ID NO: 108 | TABBY108V$_L$ SEQ ID NO: 158 |
| hu106.1x.1x | hu106-1 | hu106.1x V$_H$ SEQ ID NO: 109 | hu106.1x V$_L$ SEQ ID NO: 159 |
| hu106.1y.1x | hu106-2 | hu106.1y V$_H$ SEQ ID NO: 110 | hu106.1x V$_L$ SEQ ID NO: 159 |
| hu106.1x.2x | hu106-3 | hu106.1x V$_H$ SEQ ID NO: 109 | hu106.2x V$_L$ SEQ ID NO: 160 |
| hu106.1x.3x | hu106-4 | hu106.1x V$_H$ SEQ ID NO: 109 | hu106.3x V$_L$ SEQ ID NO: 161 |
| hu106.1x.4x | hu106-5 | hu106.1x V$_H$ SEQ ID NO: 109 | hu106.4x V$_L$ SEQ ID NO: 162 |
| hu106.1x.5x | hu106-6 | hu106.1x V$_H$ SEQ ID NO: 109 | hu106.5x V$_L$ SEQ ID NO: 163 |
| hu106.1y.3x | hu106-7 | hu106.1y V$_H$ SEQ ID NO: 110 | hu106.3x V$_L$ SEQ ID NO: 161 |
| hu107.1x.1x | hu107-1 | hu107.1x V$_H$ SEQ ID NO: 111 | hu107.1x V$_L$ SEQ ID NO: 164 |
| hu107.1y.1y | hu107-2 | hu107.1y V$_H$ SEQ ID NO: 112 | hu107.1y V$_L$ SEQ ID NO: 165 |
| hu107.1x.1y | hu107-3 | hu107.1x V$_H$ SEQ ID NO: 111 | hu107.1y V$_L$ SEQ ID NO: 165 |
| Mouse TABBY1.1 with mouse IgG1 constant | TABBY1.1-mIgG$_1$ | TABBY1.1V$_H$ SEQ ID NO: 121 | TABBY1.1V$_L$ SEQ ID NO: 171 |
| Mouse TABBY3 with mouse IgG1 constant | TABBY3-mIgG$_{2b}$ | TABBY3 V$_H$ SEQ ID NO: 123 | TABBY3 V$_L$ SEQ ID NO: 173 |
| Mouse TABBY5 with mouse IgG1 constant | TABBY5-mIgG$_{2b}$ | TABBY5 V$_H$ SEQ ID NO: 125 | TABBY5 V$_L$ SEQ ID NO: 175 |

TABLE 3-continued

Antibody Abbreviations

| Name/Description | Abbreviation | $V_H$ Sequence (FIGS. 2A-2D) | $V_L$ Sequence (FIGS. 2A-2D) |
|---|---|---|---|
| Mouse TABBY6 with mouse IgG1 constant | TABBY6-mIgG$_1$ | TABBY6 $V_H$ SEQ ID NO: 126 | TABBY6 $V_L$ SEQ ID NO: 176 |
| Mouse TABBY9 with mouse IgG1 constant | TABBY9-mIgG$_1$ | TABBY9 $V_H$ SEQ ID NO: 129 | TABBY9 $V_L$ SEQ ID NO: 179 |
| Mouse TABBY10 with mouse IgG1 constant | TABBY10-mIgG$_1$ | TABBY10 $V_H$ SEQ ID NO: 130 | TABBY10 $V_L$ SEQ ID NO: 180 |

7.2. Definitions

Unless otherwise defined herein, scientific and technical terms used in connection with the present disclosure shall have the meanings that are commonly understood by those of ordinary skill in the art.

7.3. Anti-4-1BB Antibodies and Binding Fragments

In one aspect, the disclosure concerns antibodies and/or binding fragments thereof that specifically bind human 4-1BB receptor (SEQ ID NO:1) (also known as tumor necrosis factor receptor superfamily member 9, TNFRSF59 and CD137).

As used herein, the term "antibody" (Ab) refers to an immunoglobulin molecule that specifically binds to a particular antigen—here, 4-1BB. In some embodiments, the anti-4-1BB antibodies of the disclosure bind to human 4-1BB and thereby modulate, e.g., activate, the immune system. The resulting immune system response is cytotoxic to the tumor cells. Anti-4-1BB antibodies of the disclosure comprise complementarity determining regions (CDRs), also known as hypervariable regions, in both the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The disclosure provides antibodies comprising modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies. See Kabat et al., Sequences of Proteins of Immunological Interest (National Institute of Health, Bethesda, Md. 1987). As used herein, numbering of immunoglobulin amino acid residues is done according to the immunoglobulin amino acid residue numbering system of Kabat et al. unless otherwise indicated.

The anti-4-1BB antibodies of the disclosure may be polyclonal, monoclonal, genetically engineered, and/or otherwise modified in nature, including but not limited to chimeric antibodies, humanized antibodies, human antibodies, primatized antibodies, single chain antibodies, etc. In various embodiments, the anti-4-1BB antibodies comprise all or a portion of a constant region of an antibody. In some embodiments, the constant region is an isotype selected from: IgA (e.g., IgA$_1$ or IgA$_2$), IgD, IgE, IgG (e.g., IgG$_1$, IgG$_2$, IgG$_3$ or IgG$_4$), and IgM. In specific embodiments, the anti-4-1BB antibody described herein is an IgG$_1$. In other embodiments, the anti-4-1BB antibody is an IgG$_2$ M3. In yet other embodiments, the anti-4-1BB antibody is an IgG$_4$. As used herein, the "constant region" of an antibody includes the natural constant region and allotypes or natural variants, such as D356E and L358M, or A431G in human IgG$_1$. See, e.g., Jefferis and Lefranc, MAbs, 1(4): 332-338 (July-August 2009).

The light constant region of an anti-4-1BB antibody may be a kappa (κ) light region or a lambda (λ) region. A λ light region can be any one of the known subtypes, e.g., λ$_1$, λ$_2$, λ$_3$, or λ$_4$. In some embodiments, the λ light region has a C-terminal residue truncation as compared to the corresponding wild type sequence. See, e.g., Shen et al., MAbs, 5(3): 418-431 (May-June 2013). In some embodiments, the anti-4-1BB antibody comprises a kappa (κ) light region. In some embodiments, the anti-4-1BB antibody comprises a lambda (λ) light region.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof. In many uses of the present disclosure, including in vivo use of the anti-4-1BB antibodies in humans, chimeric, primatized, humanized, or human antibodies can suitably be used.

The term "chimeric" antibody as used herein refers to an antibody having variable sequences derived from a non-human immunoglobulin, such as a rat or a mouse antibody, and human immunoglobulin constant regions, typically chosen from a human or a mouse immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807, 715; 4,816,567; and 4,816,397.

"Humanized" forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332.

"Human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See, U.S. Pat. Nos. 4,444,887 and 4,716,111; and PCT publications WO 98/46645; WO 98/50433; WO 98/24893; WO 98/16654; WO 96/34096; WO 96/33735; and WO 91/10741. Human antibodies can also be produced using transgenic mice which are incapable of expressing functional endogenous immunoglobulins but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as LakePharma, Inc. (Belmont, Calif.) or Creative BioLabs (Shirley, N.Y.) can be engaged to provide human antibodies directed against a selected antigen using technology similar to that described above. Fully human antibodies that recognize a selected epitope can be generated using a technique referred to as "guided selection." In this approach, a selected non-human monoclonal antibody, e.g., a mouse antibody, is used to guide the selection of a completely human antibody recognizing the same epitope (see, Jespers et al., 1988, Biotechnology 12:899-903).

"Primatized antibodies" comprise monkey variable regions and human constant regions. Methods for producing primatized antibodies are known in the art. See, e.g., U.S. Pat. Nos. 5,658,570; 5,681,722; and 5,693,780.

Anti-4-1BB antibodies of the disclosure include full-length (intact) antibody molecules that are capable of specifically binding human 4-1BB.

Also disclosed herein are anti-4-1BB binding fragments that are capable of specifically binding human 4-1BB. Examples of antibody binding fragments include by way of example and not limitation, Fab, Fab', F(ab')$_2$, Fv fragments, single chain Fv fragments and single domain fragments.

A Fab fragment contains the constant and variable domains of the light chain and the first constant domain (CH1) and the variable domain of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art. Fab and F(ab')$_2$ fragments lack the Fc fragment of an intact antibody, clear more rapidly from the circulation of animals, and may have less non-specific tissue binding than an intact antibody (see, e.g., Wahl et al., 1983, J. Nucl. Med. 24:316).

An "Fv" fragment is the minimum fragment of an antibody that contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Often, the six CDRs confer target binding specificity to the antibody. However, in some instances even a single variable domain (or half of an Fv comprising only three CDRs specific for a target) can have the ability to recognize and bind target, although at a lower affinity than the entire binding site.

"Single-chain Fv" or "scFv" antibody binding fragments comprise the $V_H$ and $V_L$ domains of an antibody, where these domains are present in a single polypeptide chain. Generally, the Fv polypeptide further comprises a polypeptide linker between the $V_H$ and $V_L$ domains which enables the scFv to form the desired structure for target binding.

"Single domain fragments" are composed of a single $V_H$ or $V_L$ domains which exhibit sufficient affinity to human 4-1BB. In a specific embodiment, the single domain fragment is a camelized fragment (See, e.g., Riechmann, 1999, Journal of Immunological Methods 231:25-38).

The anti-4-1BB antibodies of the disclosure include derivatized antibodies. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using Ambryx technology (See, e.g., Wolfson, 2006, Chem. Biol. 13(10):1011-2).

The anti-4-1BB antibodies or binding fragments may be antibodies or fragments whose sequences have been modified to alter at least one constant region-mediated biological effector function. For example, in some embodiments, an anti-4-1BB antibody may be modified to reduce at least one constant region-mediated biological effector function relative to the unmodified antibody, e.g., reduced binding to one or more of the Fc receptors (FcγR) such as FcγR1, FcγRIIA, FcγRIIB, FcγRIIIA and/or FcγRIIIB. FcγR binding can be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147:2657-2662). Reduction in FcγR binding ability of the antibody can also reduce other effector functions which rely on FcγR interactions, such as opsonization, phagocytosis and antigen-dependent cellular cytotoxicity ("ADCC").

The anti-4-1BB antibody or binding fragment described herein include antibodies that have been modified to acquire or improve at least one constant region-mediated biological effector function relative to an unmodified antibody, e.g., to enhance FcγR interactions (See, e.g., US Publication No. 2006/0134709). For example, an anti-4-1BB antibody of the disclosure can have a constant region that binds FcγRI, FcγRIIA, FcγRIIB, FcγRIIIA and/or FcγRIIIB with greater affinity than the corresponding wild type constant region.

Thus, antibodies of the disclosure may have alterations in biological activity that result in increased or decreased opsonization, phagocytosis, or ADCC. Such alterations are known in the art. For example, modifications in antibodies that reduce ADCC activity are described in U.S. Pat. No. 5,834,597. An exemplary ADCC lowering variant corresponds to "mutant 3" (also known as "M3," shown in FIG. 4 of U.S. Pat. No. 5,834,597) in which residues 234 and 237 (using EU numbering) are substituted with alanines. A mutant 3 (also known as "M3") variation may be used in a number of antibody isotypes, e.g., IgG2.

Additional substitutions that can modify FcγR binding and/or ADCC effector function include the K322A substitution or the L234A and L235A double substitution in the Fc region. See, e.g., Hezareh, et al. J. Virol., 75 (24): 12161-12168 (2001).

In some embodiments, the anti-4-1BB antibodies of the disclosure have low levels of, or lack, fucose. Antibodies lacking fucose have been correlated with enhanced ADCC activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

The anti-4-1BB antibodies of the disclosure can comprise modified (or variant) CH2 domains or entire Fc domains that include amino acid substitutions that increase binding to FcγRIIB and/or reduced binding to FcγRIIIA as compared to the binding of a corresponding wild-type CH2 or Fc region. Variant CH2 or variant Fc domains have been described in U.S. Patent Appl. No. 2014/0377253, which is incorporated herein in its entirety. A variant CH2 or variant Fc domain typically includes one or more substitutions at position 263, position 266, position 273, and position 305, wherein the numbering of the residues in the Fc domain is that of the EU index as in Kabat. In some embodiments, the anti-4-1BB antibodies comprise one or more substitutions selected from V263L, V266L, V273C, V273E, V273F, V273L, V273M, V273S, V273Y, V305K, and V305W, relative to the wild-type CH2 domain. In specific embodiments, the one or more substitutions of the CH2 domain are selected from V263L, V273E, V273F, V273M, V273S, and V273Y, relative to the CH2 domain of a human IgG$_1$. For example, the one or more substitutions of a CH2 domain can be V273E. In another specific embodiment, the anti-4-1BB antibody of the disclosure comprises a variant CH2 domain comprising the amino acid substitution V263L.

Other examples of variant CH2 or variant Fc domains that can afford increased binding to FcγRIIB and/or reduced binding to FcγRIIIA as compared to the binding of a corresponding wild-type CH2 or Fc region include those found in Vonderheide, et al. Clin. Cancer Res., 19(5), 1035-1043 (2013), such as S267E or S267E/L328F in human IgG$_1$.

In some embodiments, the anti-4-1BB antibodies include modifications that increase or decrease their binding affinities to the fetal Fc receptor, FcRn, for example, by mutating the immunoglobulin constant region segment at particular regions involved in FcRn interactions (see, e.g., WO 2005/123780). In particular embodiments, an anti-4-1BB antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. An exemplary substitution known to modify Fc effector function is the Fc substitution M428L, which can occur in combination with the Fc substitution T250Q. Specific combinations of suitable amino acid substitutions are identified in Table 1 of U.S. Pat. No. 7,217,797, which is incorporated herein by reference. Such mutations increase binding to FcRn, which protects the antibody from degradation and increases its half-life.

An anti-4-1BB antibody may have one or more amino acids inserted into one or more of its CDRs, for example as described in Jung and Plückthun, 1997, Protein Engineering 10:9, 959-966; Yazaki et al., 2004, Protein Eng. Des. Sel. 17(5):481-9. Epub 2004 Aug. 17; and U.S. Pat. Appl. No. 2007/0280931.

Anti-4-1BB antibodies with affinity for human 4-1BB may be desirable for therapeutic and diagnostic uses. Accordingly, the present disclosure contemplates antibodies having binding affinity to human 4-1BB. In specific embodiments, the anti-4-1BB antibodies that bind human 4-1BB with an affinity of at least about 1000 nM, but may exhibit higher affinity, for example, at least about 900 nM, 800 nM, 700 nM, 600 nM, 500 nM, 400 nM, 300 nM, 250 nM, 200 nM, 150 nM, 100 nM, 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or even higher. In some embodiments, the antibodies bind human 4-1BB with an affinity in the range of about 1 pM to about 1000 nM, or an affinity ranging between any of the foregoing values.

Affinity of anti-4-1BB antibodies for human 4-1BB can be determined using techniques well known in the art or described herein, such as for example, but not by way of limitation, ELISA, FACS, isothermal titration calorimetry (ITC), surface plasmon resonance, or fluorescent polarization assay.

Anti-4-1BB antibodies generally comprise a heavy chain comprising a variable region ($V_H$) having three complementarity determining regions ("CDRs") referred to herein (in N→C order) as $V_H$ CDR #1, $V_H$ CDR #2, and $V_H$ CDR #3, and a light chain comprising a variable region ($V_L$) having three complementarity determining regions referred to herein (in N→C order) as $V_L$ CDR #1, $V_L$ CDR #2, and $V_L$ CDR #3. The amino acid sequences of exemplary CDRs, as well as the amino acid sequence of the $V_H$ and $V_L$ regions of the heavy and light chains of exemplary anti-4-1BB are provided herein. Specific embodiments of anti-4-1BB antibodies include these exemplary CDRs and/or $V_H$ and/or $V_L$ sequences, as well as antibodies that compete for binding human 4-1BB with such antibodies.

In some embodiments, the amino acid sequences of the CDRs of an anti-4-1BB antibody are selected from the following sequences:

| CDR | Sequence (N→C) | Identifier |
|---|---|---|
| $V_H$ CDR#1: | GYTFTDFAIH | (SEQ ID NO: 11) |
|  | GYTLTSYYLN | (SEQ ID NO: 12) |
|  | DYTFTSNFLH | (SEQ ID NO: 13) |
|  | GFSLSTDGLGVT | (SEQ ID NO: 14) |
|  | GFTFNNYDMA | (SEQ ID NO: 15) |
|  | GYTFTSYYIY | (SEQ ID NO: 16) |
|  | DYTFNDYWVS | (SEQ ID NO: 17) |
|  | GYTITSAYDWS | (SEQ ID NO: 18) |
|  | GYTFNDYWVS | (SEQ ID NO: 19) |
| $V_H$ CDR#2: | WINTYTGKPTYADDFKG | (SEQ ID NO: 21) |
|  | YIDTGSGGSHYNEKFKG | (SEQ ID NO: 22) |
|  | WINPGDGDTYYNQKFNG | (SEQ ID NO: 23) |
|  | NIWWDDDKDYNPSLKN | (SEQ ID NO: 24) |
|  | TISYDGSTTYYRDSVKG | (SEQ ID NO: 25) |
|  | NIWPGNGGTFYGEKFMG | (SEQ ID NO: 26) |
|  | EIYPNSGATNFNGKFRG | (SEQ ID NO: 27) |
|  | YIAYIGFTNSNPSLKS | (SEQ ID NO: 28) |
| $V_H$ CDR#3: | GAPRPTN | (SEQ ID NO: 31) |
|  | GGYYDGFFDY | (SEQ ID NO: 32) |
|  | GNYYAAHYPPGPWYFDF | (SEQ ID NO: 33) |
|  | IVPNSGHEDY | (SEQ ID NO: 34) |
|  | VGAGDFDY | (SEQ ID NO: 35) |
|  | RPDYSGDDYFDY | (SEQ ID NO: 36) |
|  | EYTRDWFAY | (SEQ ID NO: 37) |
|  | WSSYIPRYFDF | (SEQ ID NO: 38) |
| $V_L$ CDR#1: | LASEDIYNNLA | (SEQ ID NO: 51) |
|  | LASEGISNDLA | (SEQ ID NO: 52) |
|  | RASKSVSIYMH | (SEQ ID NO: 53) |
|  | KASQNINRYLN | (SEQ ID NO: 54) |
|  | LASEDIYSDLA | (SEQ ID NO: 55) |
|  | KLNSGNIGSYYVH | (SEQ ID NO: 56) |
|  | RSSQSLLDSDGNTYLY | (SEQ ID NO: 57) |
|  | TITSGNIEDNFVH | (SEQ ID NO: 58) |
| $V_L$ CDR#2: | YESRLQD | (SEQ ID NO: 61) |
|  | AASRLQD | (SEQ ID NO: 62) |
|  | TASNLES | (SEQ ID NO: 63) |
|  | NTNSMQT | (SEQ ID NO: 64) |
|  | STNTLQN | (SEQ ID NO: 65) |
|  | RDDKRPD | (SEQ ID NO: 66) |
|  | LVSNLGS | (SEQ ID NO: 67) |
|  | NDDKRPD | (SEQ ID NO: 68) |
| $V_L$ CDR#3: | LQDSEYPYT | (SEQ ID NO: 71) |
|  | QQSYKYPPT | (SEQ ID NO: 72) |
|  | QQSNELPFT | (SEQ ID NO: 73) |
|  | LQHNSWPRT | (SEQ ID NO: 74) |
|  | QQNNNYPYT | (SEQ ID NO: 75) |
|  | HSYDSTITPV | (SEQ ID NO: 76) |
|  | MQPTHAPYT | (SEQ ID NO: 77) |
|  | HSYVSSINI | (SEQ ID NO: 78) |

In some embodiments, the amino acid sequences of the CDRs of an anti-4-1BB antibody are selected from the following sequences:

| CDR | Sequence (N→C) | Identifier |
|---|---|---|
| $V_H$ CDR#1: | GFTFSSYGMS | (SEQ ID NO: 201) |
|  | GFTFSSFGMH | (SEQ ID NO: 203) |
|  | GFNIKDYYMH | (SEQ ID NO: 205) |
|  | GFSLTSYGVH | (SEQ ID NO: 209) |
|  | GYTFTTYGMS | (SEQ ID NO: 210) |
| $V_H$ CDR#2: | AIISGGSYTYYPDSVKG | (SEQ ID NO: 211) |
|  | YISSGSSTIYYADTLKG | (SEQ ID NO: 213) |
|  | RIDPEDGDTEYVPKFQG | (SEQ ID NO: 215) |
|  | RIDPEDGDTEYAPKFQG | (SEQ ID NO: 216) |
|  | MIWSGGSTDYNAAFIS | (SEQ ID NO: 219) |
|  | WINTYSGVPTYADDFKG | (SEQ ID NO: 220) |
| $V_H$ CDR#3: | HGGYDGNYDYYAMDY | (SEQ ID NO: 221) |
|  | DWVDY | (SEQ ID NO: 223) |
|  | YSNYVYWYFDV | (SEQ ID NO: 225) |
|  | YGGFYETMDY | (SEQ ID NO: 229) |
|  | GNDGNYYGWFAH | (SEQ ID NO: 230) |
| $V_L$ CDR#1: | RSSQSIVDSDGITYLE | (SEQ ID NO: 231) |
|  | RSSKSLLYKDGKTYLN | (SEQ ID NO: 233) |
|  | KSSQSLLDSDGKTYLN | (SEQ ID NO: 235) |
|  | RASQDISNYLN | (SEQ ID NO: 239) |
|  | KASQDIHNYIS | (SEQ ID NO: 240) |
| $V_L$ CDR#2: | KVSNRFS | (SEQ ID NO: 241) |
|  | LMSTRAS | (SEQ ID NO: 243) |
|  | LVSKLDS | (SEQ ID NO: 245) |
|  | YTSRLHS | (SEQ ID NO: 249) |
|  | YTSTLQP | (SEQ ID NO: 250) |
| $V_L$ CDR#3: | FQVSHVPWT | (SEQ ID NO: 251) |
|  | QQPVEYPYT | (SEQ ID NO: 253) |
|  | WQGTHFPHT | (SEQ ID NO: 255) |
|  | QQGNTLPYT | (SEQ ID NO: 259) |
|  | LQYDNLYT | (SEQ ID NO: 260) |

In some embodiments, each CDR of an anti-4-1BB antibody, independently of the others, is selected to correspond in sequence to the respective CDR of an antibody provided in TABLE 3. In some embodiments, an anti-4-1BB antibody is an IgG, and has a $V_H$ and $V_L$ corresponding in sequence to the $V_H$ and $V_L$ of an antibody provided in TABLE 3. In some embodiments, an anti-4-1BB antibody is a humanized version of an antibody provided in TABLE 3. In some embodiments, an anti-4-1BB antibody is a humanized version of TABBY106 or TABBY107.

Specific exemplary embodiments of anti-4-1BB antibodies with the above CDRs are described herein. In some embodiments, an anti-4-1BB antibody has the CDRs of SEQ ID NOS: 11, 21, 31, 51, 61, and 71. In some embodiments, an anti-4-1BB antibody has the CDRs of SEQ ID NOS: 12, 22, 32, 52, 62, and 72. In some embodiments, an anti-4-1BB antibody has the CDRs of SEQ ID NOS: 13, 23, 33, 53, 63, and 73. In some embodiments, an anti-4-1BB antibody has the CDRs of SEQ ID NOS: 14, 24, 34, 54, 64, and 74. In some embodiments, an anti-4-1BB antibody has the CDRs of SEQ ID NOS: 15, 25, 35, 55, 65, and 75. In some embodiments, an anti-4-1BB antibody has the CDRs of SEQ ID NOS: 16, 26, 36, 56, 66, and 76. In some embodiments, an anti-4-1BB antibody has the CDRs of SEQ ID NOS: 17, 27, 37, 57, 67, and 77. In some embodiments, an anti-4-1BB antibody has the CDRs of SEQ ID NOS: 18, 28, 38, 58, 68, and 78. In some embodiments, an anti-4-1BB antibody has the CDRs of SEQ ID NOS: 19, 27, 37, 57, 67, and 77.

In some embodiments, an anti-4-1BB antibody has the CDRs of SEQ ID NOS: 201, 211, 221, 231, 241, and 251. In some embodiments, an anti-4-1BB antibody has the CDRs of SEQ ID NOS: 203, 213, 223, 233, 243, and 253. In some embodiments, an anti-4-1BB antibody has the CDRs of SEQ ID NOS: 205, 215, 225, 235, 245, and 255. In some embodiments, an anti-4-1BB antibody has the CDRs of SEQ ID NOS: 205, 216, 225, 235, 245, and 255. In some embodiments, an anti-4-1BB antibody has the CDRs of SEQ ID NOS: 209, 219, 229, 239, 249, and 259. In some embodiments, an anti-4-1BB antibody has the CDRs of SEQ ID NOS: 210, 220, 230, 240, 250, and 260.

In some embodiments, an anti-4-1BB antibody comprises a $V_H$ chain corresponding in sequence to any one of SEQ ID NOS:101-112; and a $V_L$ chain corresponding in sequence to any one of SEQ ID NOS:151-165. In some embodiments, an anti-4-1BB antibody comprises a $V_H$ chain corresponding in sequence to SEQ ID NO:101 and a $V_L$ chain corresponding in sequence to SEQ ID NO:151. In some embodiments, an anti-4-1BB antibody comprises a $V_H$ chain corresponding in sequence to SEQ ID NO:102 and a $V_L$ chain corresponding in sequence to SEQ ID NO:152. In some embodiments, an anti-4-1BB antibody comprises a $V_H$ chain corresponding in sequence to SEQ ID NO:103 and a $V_L$ chain corresponding in sequence to SEQ ID NO:153. In some embodiments, an anti-4-1BB antibody comprises a $V_H$ chain corresponding in sequence to SEQ ID NO:104 and a $V_L$ chain corresponding in sequence to SEQ ID NO:154. In some embodiments, an anti-4-1BB antibody comprises a $V_H$ chain corresponding in sequence to SEQ ID NO:105 and a $V_L$ chain corresponding in sequence to SEQ ID NO:155. In some embodiments, an anti-4-1BB antibody comprises a $V_H$ chain corresponding in sequence to SEQ ID NO:106 and a $V_L$ chain corresponding in sequence to SEQ ID NO:156. In some embodiments, an anti-4-1BB antibody comprises a $V_H$ chain corresponding in sequence to SEQ ID NO:107 and a $V_L$ chain corresponding in sequence to SEQ ID NO:157. In some embodiments, an anti-4-1BB antibody comprises a $V_H$ chain corresponding in sequence to SEQ ID NO:108 and a $V_L$ chain corresponding in sequence to SEQ ID NO:158.

In some embodiments, an anti-4-1BB antibody comprises a $V_H$ chain corresponding in sequence to any one of SEQ ID NOS:121, 123, 125, 126, 129, and 130; and a $V_L$ chain corresponding in sequence to any one of SEQ ID NOS:171, 173, 175, 176, 179, and 180. In some embodiments, an anti-4-1BB antibody comprises a $V_H$ chain corresponding in sequence to SEQ ID NO:121 and a $V_L$ chain corresponding in sequence to SEQ ID NO:171. In some embodiments, an anti-4-1BB antibody comprises a $V_H$ chain corresponding in sequence to SEQ ID NO:123 and a $V_L$ chain corresponding in sequence to SEQ ID NO:173. In some embodiments, an anti-4-1BB antibody comprises a $V_H$ chain corresponding in sequence to SEQ ID NO:125 and a $V_L$ chain corresponding in sequence to SEQ ID NO:175. In some embodiments, an anti-4-1BB antibody comprises a $V_H$ chain corresponding in sequence to SEQ ID NO:126 and a $V_L$ chain corresponding in sequence to SEQ ID NO:176. In some embodiments, an anti-4-1BB antibody comprises a $V_H$ chain corresponding in sequence to SEQ ID NO:129 and a $V_L$ chain corresponding in sequence to SEQ ID NO:179. In some embodiments, an anti-4-1BB antibody comprises a $V_H$ chain corresponding in sequence to SEQ ID NO:130 and a $V_L$ chain corresponding in sequence to SEQ ID NO:180.

In some embodiments, an anti-4-1BB antibody is suitable for administration to humans. In a specific embodiment, the anti-4-1BB antibody is humanized. In another specific embodiment, the amino acid sequences of the CDRs of the anti-4-1BB antibody are selected from: $V_H$ CDR #1 of SEQ ID NO:16, 17, or 19; $V_H$ CDR #2 of SEQ ID NO:26 or 27; $V_H$ CDR #3 of SEQ ID NO:36 or 37; $V_L$ CDR #1 of SEQ ID NO:56 or 57; $V_L$ CDR #2 of SEQ ID NO:66 or 67; and $V_L$ CDR #3 of SEQ ID NO:76 or 77. In some embodiments, an anti-4-1BB antibody has the CDRs of SEQ ID NOS: 16, 26, 36, 56, 66, and 76. In some embodiments, an anti-4-1BB antibody has the CDRs of SEQ ID NOS: 17, 27, 37, 57, 67, and 77. In some embodiments, an anti-4-1BB antibody has the CDRs of SEQ ID NOS: 19, 27, 37, 57, 67, and 77.

In some embodiments, an anti-4-1BB antibody comprises a $V_H$ chain corresponding in sequence to any one of SEQ ID NOS:109, 110, 111, and 112; and a $V_L$ chain corresponding in sequence to any one of SEQ ID NOS:159, 160, 161, 162, 163, 164, and 165. In some embodiments, an anti-4-1BB antibody comprises a $V_H$ chain corresponding in sequence to SEQ ID NO:109 and a $V_L$ chain corresponding in sequence to SEQ ID NO:159. In some embodiments, an anti-4-1BB antibody comprises a $V_H$ chain corresponding in sequence to SEQ ID NO:109 and a $V_L$ chain corresponding in sequence to SEQ ID NO:160. In some embodiments, an anti-4-1BB antibody comprises a $V_H$ chain corresponding in sequence to SEQ ID NO:110 and a $V_L$ chain corresponding in sequence to SEQ ID NO:159. In some embodiments, an anti-4-1BB antibody comprises a $V_H$ chain corresponding in sequence to SEQ ID NO:110 and a $V_L$ chain corresponding in sequence to SEQ ID NO:160. In some embodiments, an anti-4-1BB antibody comprises a $V_H$ chain corresponding in sequence to SEQ ID NO:109 and a $V_L$ chain corresponding in sequence to SEQ ID NO:161. In some embodiments, an anti-4-1BB antibody comprises a $V_H$ chain corresponding in sequence to SEQ ID NO:109 and a $V_L$ chain corresponding in sequence to SEQ ID NO:162. In some embodiments, an anti-4-1BB antibody comprises a $V_H$ chain corresponding in sequence to SEQ ID NO:109 and a $V_L$ chain corresponding in sequence to SEQ ID NO:163. In some embodiments, an anti-4-1BB antibody comprises a $V_H$ chain corresponding in sequence to SEQ ID NO:110 and a $V_L$ chain corresponding in sequence to SEQ ID NO:159. In some embodiments, an anti-4-1BB antibody comprises a $V_H$ chain corresponding in sequence to SEQ ID NO:110 and a $V_L$ chain corresponding in sequence to SEQ ID NO:160. In some embodiments, an anti-4-1BB antibody comprises a $V_H$ chain corresponding in sequence to SEQ ID NO:110 and a $V_L$ chain corresponding in sequence to SEQ ID NO:161. In some embodiments, an anti-4-1BB antibody comprises a $V_H$ chain corresponding in sequence to SEQ ID NO:110 and a $V_L$ chain corresponding in sequence to SEQ ID NO:162. In some embodiments, an anti-4-1BB antibody comprises a $V_H$ chain corresponding in sequence to SEQ ID NO:110 and a $V_L$ chain corresponding in sequence to SEQ ID NO:163. In some embodiments, an anti-4-1BB antibody comprises a $V_H$ chain corresponding in sequence to SEQ ID NO:111 and a $V_L$ chain corresponding in sequence to SEQ ID NO:163. In some embodiments, an anti-4-1BB antibody comprises a $V_H$ chain corresponding in sequence to SEQ ID NO:111 and a $V_L$ chain corresponding in sequence to SEQ ID NO:164. In some embodiments, an anti-4-1BB antibody comprises a $V_H$ chain corresponding in sequence to SEQ ID NO:111 and a $V_L$ chain corresponding in sequence to SEQ ID NO:165. In some embodiments, an anti-4-1BB antibody comprises a $V_H$ chain corresponding in sequence to SEQ ID NO:112 and a $V_L$ chain corresponding in sequence to SEQ ID NO:165. In some embodiments, an anti-4-1BB antibody comprises a $V_H$ chain corresponding in sequence to SEQ ID NO:112 and a $V_L$ chain corresponding in sequence to SEQ ID NO:164. In some embodiments, an anti-4-1BB antibody comprises a $V_H$ chain corresponding in sequence to SEQ ID NO:111 and a $V_L$ chain corresponding in sequence to SEQ ID NO:165.

Certain mutations of a $V_H$ or $V_L$ sequence in an anti-4-1BB antibody described herein would be understood by a person of skill to afford anti-4-1BB antibodies within the scope of the disclosure. Mutations may include amino acid substitutions, additions, or deletions from a $V_H$ or $V_L$ sequence as disclosed herein while retaining significant anti-4-1BB activity. Accordingly, in some embodiments, an anti-4-1BB antibody comprises a $V_H$ sequence having at least 85%, at least 90%, at least 93%, at least 95%, at least 96%, at least 97%, at least 98%, or at least 99% sequence identity to the $V_H$ sequence of any one of the antibodies shown in TABLE 3. An anti-4-1BB antibody can comprise a $V_H$ sequence having up to 8, up to 7, up to 6, up to 5, up to 4, up to 3, or up to 2 mutations compared with the $V_H$ sequence of any one of the antibodies shown in TABLE 3. In some embodiments, an anti-4-1BB antibody can comprise a $V_H$ sequence having 5 or fewer, 4 or fewer, 3 or fewer, or 2 or fewer mutations compared with the $V_H$ sequence of any one of the antibodies shown in TABLE 3. In some embodiments, an anti-4-1BB antibody comprises a $V_L$ sequence having at least 85%, at least 90%, at least 93%, at least 95%, at least 96%, at least 97%, at least 98%, or at least 99% sequence identity to the $V_L$ sequence of any one of the antibodies shown in TABLE 3. An anti-4-1BB antibody can comprise a $V_L$ sequence having up to 8, up to 7, up to 6, up to 5, up to 4, up to 3, or up to 2 mutations compared with the $V_L$ sequence of any one of the antibodies shown in TABLE 3. In some embodiments, an anti-4-1BB antibody can comprise a $V_L$ sequence having 5 or fewer, 4 or fewer, 3 or fewer, or 2 or fewer mutations compared with the $V_L$ sequence of any one of the antibodies shown in TABLE 3.

Post-translational modifications to the sequences of an anti-4-1BB antibody may occur, such as cleavage of one or more (e.g., 1, 2, 3, or more) amino acid residues on the C-terminal end of the antibody heavy chain.

In some embodiments, an anti-4-1BB antibody has a heavy chain according to SEQ ID NO:310 or 311 and a light chain according to SEQ ID NO:314. In some embodiments, an anti-4-1BB antibody has a heavy chain according to SEQ ID NO:312 or 313 and a light chain according to SEQ ID NO:315.

In some embodiments, the anti-4-1BB antibodies compete for binding human 4-1BB in in vitro assays with a reference antibody. In some embodiments, the anti-4-1BB antibodies compete for binding human 4-1BB on cells expressing human 4-1BB. The reference antibody may be any of the anti-4-1BB antibodies described herein. In some embodiments, the reference antibody is an antibody provided in TABLE 3. In specific embodiments, the reference antibody is selected from antibody TABBY1.1 ("TABBY1.1"); antibody TABBY3 ("TABBY3"); antibody TABBY5 ("TABBY5"); antibody TABBY6 ("TABBY6"); antibody TABBY9 ("TABBY9"); antibody TABBY10 ("TABBY10"); antibody TABBY101 ("TABBY101"); antibody TABBY102 ("TABBY102"); antibody TABBY103 ("TABBY103"); antibody TABBY104 ("TABBY104"); antibody TABBY105 ("TABBY105"); antibody TABBY106 ("TABBY106"); antibody TABBY107 ("TABBY107"); and antibody TABBY108 ("TABBY108"). In some embodiments, the reference antibody is a humanized version of an antibody provided in TABLE 3. In a specific embodiment, the reference antibody is TABBY106. In another specific embodiment, the reference antibody is TABBY107.

In some embodiments, an anti-4-1BB antibody activates, e.g., agonizes, human 4-1BB (SEQ ID NO:1). Activation of 4-1BB may occur with or without competitive binding to human 4-1BBL (SEQ ID NO:2). In some embodiments, an anti-4-1BB antibody does not compete with 4-1BBL in binding to human 4-1BB. In some embodiments, an anti-4-1BB antibody competes for binding human 4-1BB with a control antibody selected from an antibody of TABLE 3, but does not compete with human 4-1BBL binding to human 4-1BB in the competition assay of Section 8.1.3, and does not activate human 4-1BB in the absence of a receptor crosslinker in the CD8+ T-cell costimulation assay described in Section 8.1.5. In some embodiments, an anti-4-1BB antibody competes for binding human 4-1BB with a control antibody selected from an antibody of TABLE 3, but does not compete with human 4-1BBL binding to human 4-1BB in the competition assay of Section 8.1.4, and does not activate human 4-1BB in the absence of a receptor crosslinker in the CD8+ T-cell costimulation assay described in Section 8.1.5.

The anti-4-1BB antibodies described herein generally bind specifically to human 4-1BB. Cross reactivity of the antibodies for binding to 4-1BB from other species, for example, from mouse, rat or monkey, e.g., cynomolgus monkey, may offer advantages, such as the ability to test in mouse, rat or monkey animal models for biological activity. Such animal model testing may be used to screen anti-4-1BB antibodies to select properties related to efficacy, e.g., favorable pharmacokinetics, or those related to safety, e.g., decreased hepatic toxicity. In some embodiments, the anti-4-1BB antibodies bind to mouse 4-1BB (SEQ ID NO:3) as well as human 4-1BB. In other embodiments, the anti-4-1BB antibodies bind to cynomolgus 4-1BB (SEQ ID NO:4) as well as human 4-1BB. In certain embodiments, the anti-4-1BB antibodies bind to mouse 4-1BB and cynomolgus 4-1BB as well as human 4-1BB. In certain embodiments, the anti-4-1BB antibodies bind to rat 4-1BB (SEQ ID NO:5) and cynomolgus 4-1BB as well as human 4-1BB.

Assays for competition include, but are not limited to, a radioactive material labeled immunoassay (RIA), an enzyme-linked immunosorbent assay (ELISA), a sandwich ELISA, fluorescence activated cell sorting (FACS) assays, and surface plasmon resonance assays.

In conducting an antibody competition assay between a reference antibody and a test antibody (irrespective of species or isotype), one may first label the reference with a detectable label, such as a fluorophore, biotin or an enzymatic (or even radioactive) label to enable subsequent identification. In this case, cells expressing human 4-1BB are incubated with unlabeled test antibody, labeled reference antibody is added, and the intensity of the bound label is measured. If the test antibody competes with the labeled reference antibody by binding to an overlapping epitope, the intensity will be decreased relative to a control reaction carried out without test antibody.

In a specific embodiment of this assay, the concentration of labeled reference antibody that yields 80% of maximal binding ("$conc_{80\%}$") under the assay conditions (e.g., a specified density of cells) is first determined, and a competition assay carried out with 10× $conc_{80\%}$ of unlabeled test antibody and $conc_{80\%}$ of labeled reference antibody.

The inhibition can be expressed as an inhibition constant, or which is calculated according to the following formula:

$$K_i = IC_{50}/(1+[\text{reference } Ab \text{ concentration}]/K_d),$$

where $IC_{50}$ is the concentration of test antibody that yields a 50% reduction in binding of the reference antibody and $K_d$ is the dissociation constant of the reference antibody, a measure of its affinity for human 4-1BB. Antibodies that compete with anti-4-1BB antibodies disclosed herein can have a $K_i$ from 10 pM to 1000 nM under assay conditions described herein.

In various embodiments, a test antibody is considered to compete with a reference antibody if it decreases binding of the reference antibody by at least about 20% or more, for example, by at least about 20%, 30%, 40%, 50%, 60%, 70%, 80%, 90%, 95% or even more, or by a percentage ranging between any of the foregoing values, at a reference antibody concentration that is 80% of maximal binding under the specific assay conditions used, and a test antibody concentration that is 10-fold higher than the reference antibody concentration.

A specific assay and assay conditions useful for assessing whether an antibody competes for binding human 4-1BB with a reference antibody as described herein is provided in Example 1. Competition with a reference antibody may be determined by the binding competition assay described in Section 8.1.3 or Section 8.1.4.

In some embodiments, an anti-4-1BB antibody described herein competes for binding human 4-1BB (SEQ ID NO:1) with a control antibody selected from an antibody of TABLE 3, but does not compete with human 4-1BBL (SEQ ID NO:2) binding to human 4-1BB in a competition assay according to Section 8.1.3, binds to both mouse and cynomolgus 4-1BB in a binding assay according to Section 8.1.3, and does not activate human 4-1BB in the absence of a receptor crosslinker in a CD8+ T-cell costimulation assay according to Section 8.1.5. In some embodiments, an anti-4-1BB antibody described herein competes for binding human 4-1BB (SEQ ID NO:1) with a control antibody selected from an antibody of TABLE 3, but does not compete with human 4-1BBL (SEQ ID NO:2) binding to human 4-1BB in a competition assay according to Section 8.1.4, binds to both mouse and cynomolgus 4-1BB in a binding assay according to Section 8.1.4, and does not activate human 4-1BB in the absence of a receptor crosslinker in a CD8+ T-cell costimulation assay according to Section 8.1.5. In some embodiments, the receptor crosslinker is a Fcγ receptor expressed on cells.

The anti-4-1BB antibodies described herein generally activate, e.g., agonize, human 4-1BB in the presence of a 4-1BB receptor crosslinker, such as an Fc crosslinker, but do not activate human 4-1BB in the absence of a crosslinker. An anti-4-1BB antibody that activates only in the presence of an additional crosslinker may be advantageous to activate the immune system under certain in vivo conditions, e.g., in the tumor microenvironment, rather than generally activating the immune system. Such activity can be assessed, for example, in a CD8+ T-cell costimulation assay, such as that described in Example 1 herein, with an endpoint determined by proliferation (e.g., as measured by $^3$H thymidine incorporation) or by cytokine release (e.g., as measured by interferon-gamma (IFN-γ)). In an assay, a 4-1BB receptor crosslinker can be provided by addition of an external agent, such as an anti-human IgG antibody. Crosslinking may also be effected via cellular FcγR-mediated crosslinking, e.g., the presence of FcγR1, FcγRIIA, FcγRIIB, FcγRIIIA and/or FcγRIIIB receptors in the local cellular environment in vitro or in vivo. In some embodiments, the activity of human 4-1BB is at least about 1.3-fold higher, such as about 1.4, 1.5, 1.6, 1.8, 2, 2.5, 3, 4, 5, 6, 8, 10, 20, 30, 40, 50, 60, 70, 80, 90, 100, 200, 300, 400, 500, 600, 700, 800, 900, 1000, 1500, 2000-fold or greater, with treatment of the anti-4-1BB antibody in the presence of a receptor crosslinker as compared to treatment with the same dose of control antibody in the assay of Section 8.1.5.

While not wishing to be bound by theory, the ability of the anti-4-1BB antibody of the disclosure to activate, e.g., agonize, human 4-1BB only in the presence of a 4-1BB receptor crosslinker is believed to effect activation of human 4-1BB under certain in vivo conditions where it may be advantageous to activate the immune system, e.g., in the tumor microenvironment. Such conditional activation may afford a greater therapeutic window for treatment by an anti-4-1BB antibody, for example, through lower toxicity, e.g., lower liver toxicity, associated with treatment of the anti-4-1BB antibody of the present disclosure as compared with the same dose of an anti-4-1BB antibody that activates human 4-1BB in the absence of a 4-1BB receptor crosslinker. Liver toxicity may be assessed by the measurement of serum enzyme levels, such as alanine aminotransferase (also known as ALT), and measured after treatment of an anti-4-1BB antibody or an equivalent dose of an isotype control. For example, elevated ALT levels after treatment of the anti-4-1BB antibody but not the isotype control may indicate liver toxicity. In some embodiments, treatment of an anti-4-1BB antibody of the disclosure effects lower liver toxicity, e.g., smaller increase in ALT levels compared with isotype, as compared with the same dose of an anti-4-1BB antibody that activates human 4-1BB in the absence of a 4-1BB receptor crosslinker. In some embodiments, treatment of an anti-4-1BB antibody of the disclosure effects no change in liver toxicity, e.g., no significant change in ALT levels compared with isotype, when administered at doses ranging from about 0.01 mg/kg to about 10 mg/kg, e.g., from about 0.1 mg/kg to about 10 mg/kg or from about 1 mg/kg to about 10 mg/kg, e.g., at about 0.01, 0.05, 0.1, 0.5, 1, 2, 5, or about 10 mg/kg.

7.4. Polynucleotides Encoding the Anti-4-1BB Antibodies, Expression Systems and Methods of Making the Antibodies The present disclosure encompasses nucleic acid molecules encoding immunoglobulin light and heavy chain genes for anti-4-1BB antibodies, vectors comprising such nucleic acids, and host cells capable of producing the anti-4-1BB antibodies of the disclosure.

An anti-4-1BB antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N. Y., 1989), Current Protocols in Molecular Biology (Ausubel, F. M. et al., eds., Greene Publishing Associates, 1989) and in U.S. Pat. No. 4,816,397.

To generate nucleic acids encoding such anti-4-1BB antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR). Germline DNA sequences for human heavy and light chain variable region genes are known in the art (See, e.g., the "VBASE" human germline sequence database; see also Kabat, E. A. et al., 1991, Sequences of Proteins of Immunological Interest, Fifth Edition, U.S. Department of Health and Human Services, NIH Publication No. 91-3242; Tomlinson et al., 1992, J. Mol. Biol. 22T:116-198; and Cox et al., 1994, Eur. J. Immunol. 24:827-836; the contents of each of which are incorporated herein by reference).

Once DNA fragments encoding anti-4-1BB antibody-related $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CHL CH2, CH3 and, optionally, CH4). The sequences of human heavy chain constant region genes are known in the art (See, e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ or $IgG_4$. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (See, e.g., Kabat, et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but in certain embodiments is a kappa constant region. To create a scFv gene, the $V_H$- and $V_L$-encoding DNA fragments are operatively linked to another fragment encoding a flexible linker, e.g., encoding the amino acid sequence (Gly4-Ser)3 (SEQ ID NO:90), such that the $V_H$ and $V_L$ sequences can be expressed as a contiguous single-chain protein, with the $V_L$ and $V_H$ regions joined by the flexible linker (See, e.g., Bird et al., 1988, Science 242:423-426; Huston et al., 1988, Proc. Natl. Acad. Sci. USA 85:5879-5883; McCafferty et al., 1990, Nature 348:552-554).

To express the anti-4-1BB antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-4-1BB antibody-related light or heavy chain sequences, the expression vector can already carry antibody constant region sequences. For example, one approach to converting the anti-4-1BB monoclonal antibody-related $V_H$ and $V_L$ sequences to full-length antibody genes is to insert them into expression vectors already encoding heavy chain constant and light chain constant regions, respectively, such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185, Academic Press, San Diego, Calif., 1990. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (See, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the antibodies of the disclosure in either prokaryotic or eukaryotic host cells. In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-4-1BB antibody of this disclosure.

Recombinant DNA technology can also be used to remove some or all of the DNA encoding either or both of the light and heavy chains that is not necessary for binding to human 4-1BB. The molecules expressed from such truncated DNA molecules are also encompassed by the antibodies of the disclosure.

For recombinant expression of an anti-4-1BB antibody of the disclosure, the host cell can be co-transfected with two expression vectors of the disclosure, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

Once a nucleic acid encoding one or more portions of an anti-4-1BB antibody, further alterations or mutations can be introduced into the coding sequence, for example to generate nucleic acids encoding antibodies with different CDR sequences, antibodies with reduced affinity to the Fc receptor, or antibodies of different subclasses.

The anti-4-1BB antibodies of the disclosure can also be produced by chemical synthesis (e.g., by the methods described in Solid Phase Peptide Synthesis, 2nd ed., 1984, The Pierce Chemical Co., Rockford, Ill.). Variant antibodies can also be generated using a cell-free platform (See, e.g., Chu et al., Biochemia No. 2, 2001 (Roche Molecular Biologicals) and Murray et al., 2013, Current Opinion in Chemical Biology, 17:420-426).

Once an anti-4-1BB antibody of the disclosure has been produced by recombinant expression, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the anti-4-1BB antibodies of the present disclosure can be fused to heterologous polypeptide sequences described herein or otherwise known in the art to facilitate purification.

Once isolated, the anti-4-1BB antibody can, if desired, be further purified, e.g., by high performance liquid chromatography (see, e.g., Fisher, Laboratory Techniques In Biochemistry And Molecular Biology, Work and Burdon, eds., Elsevier, 1980), or by gel filtration chromatography on a Superdex™ 75 column (Pharmacia Biotech AB, Uppsala, Sweden).

7.5. Pharmaceutical Compositions

The anti-4-1BB antibodies described herein may be in the form of compositions comprising the antibody and one or more carriers, excipients and/or diluents. The compositions may be formulated for specific uses, such as for veterinary uses or pharmaceutical uses in humans. The form of the composition (e.g., dry powder, liquid formulation, etc.) and the excipients, diluents and/or carriers used will depend upon the intended uses of the antibody and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a subject, e.g., a human subject, i.e., patient). The pharmaceutical composition can be administered to a subject by a variety of routes such as orally, transdermally, subcutaneously, intranasally, intravenously, intramuscularly, intratumorally, intrathecally, topically or locally. The most suitable route for administration in any given case will depend on the particular antibody, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of an anti-4-1BB antibody described herein per dose. The quantity of anti-4-1BB antibody included in a unit dose will depend on the disease being treated, as well as other factors as are well known in the art. Such unit dosages may be in the form of a lyophilized dry powder containing an amount of antibody suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of the anti-4-1BB antibody suitable for a single administration.

The pharmaceutical compositions may also be supplied in bulk form containing quantities of anti-4-1BB antibody suitable for multiple administrations.

Pharmaceutical compositions may be prepared for storage as lyophilized formulations or aqueous solutions by mixing an antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives should be nontoxic to the recipients at the dosages and concentrations employed.

Buffering agents help to maintain the pH in the range which approximates physiological conditions. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), phosphate buffers (e.g., phosphoric acid-monosodium phosphate mixture, phosphoric acid-disodium phosphate mixture, monosodium phosphate-disodium phosphate mixture, etc.), gluconate buffers (e.g., gluconic acid-sodium gluconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, fumarate buffers, histidine buffers and trimethylamine salts such as 2-amino-2-hydroxymethyl-propane-1,3-diol (i.e., Tris, THAM, or tris(hydroxymethyl)aminomethane) can be used.

Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, leucine, 2-phenylalanine, glutamic acid, threonine, etc., organic sugars or sugar alcohols, such as lactose, trehalose, stachyose, mannitol, sorbitol, xylitol, ribitol, myoinositol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thiosulfate; low molecular weight polypeptides (e.g., peptides of 10 residues or fewer); hydrophilic polymers, such as polyvinylpyrrolidone monosaccharides, such as xylose, mannose, fructose, glucose; disaccharides such as lactose, maltose, sucrose and trehalose; and trisaccacharides such as raffinose; and polysaccharides such as dextran. Stabilizers may be present in amounts ranging from 0.5 to 10 weight % per weight of antibody.

Non-ionic surfactants or detergents (also known as "wetting agents") may be added to help solubilize the glycoprotein as well as to protect the glycoprotein against agitation-induced aggregation, which also permits the formulation to be exposed to shear surface stressed without causing denaturation of the protein. Suitable non-ionic surfactants include polysorbates (20, 80, etc.), poloxamers (184, 188 etc.), and pluronic polyols. Non-ionic surfactants may be present in a range of about 0.05 mg/mL to about 1.0 mg/mL.

7.6. Methods of Use 7.6.1. Therapeutic Benefit

Data provided herein demonstrate that anti-4-1BB antibodies described herein that agonize 4-1BB in the presence of tumor cells exert potent anti-tumor activity against these solid tumors in vivo. Accordingly, the anti-4-1BB antibodies and/or pharmaceutical compositions comprising the anti-4-1BB antibodies may be used therapeutically to treat solid tumors.

Generally, the methods involve administering to a human patient having a solid tumor an amount of an anti-4-1BB antibody that agonizes 4-1BB, and kills tumor cells at a rate effective to provide therapeutic benefit. Solid tumors that may be treated with the anti-4-1BB antibody include, but are not limited to, adrenal cancers, bone cancers, brain cancers, breast cancers, colorectal cancers, esophageal cancers, eye cancers, gastric cancers, head and neck cancers, kidney cancers, liver cancers, lung cancers (for example, non-small cell lung cancer, mesothelioma), lymphomas (e.g., B cell lymphomas), melanomas (e.g., advanced malignant melanoma), oral cancers, ovarian cancers, penile cancers, prostate cancers, pancreatic cancers, skin cancers, testicular cancers, thyroid cancers, uterine cancers, and vaginal cancers. The cancer may be newly diagnosed and naïve to treatment, or may be relapsed, refractory, or relapsed and refractory, or a metastatic form of a solid tumor.

Without wishing to be limited by theory, it is believed that an anti-4-1BB antibody activates the immune system by agonizing 4-1BB. The subsequent immune response then exerts an antitumor effect on adjacent tumor cells, without regard to 4-1BB expression levels. Accordingly, an anti-4-1BB antibody of the disclosure is expected to be effective against 4-1BB-positive or 4-1BB-negative solid tumors. See, Yonezawa, A. et al. Clinical Cancer Research, 21 (14); 3113-3120 (2015).

An anti-4-1BB antibody of the disclosure may be administered alone (monotherapy) or adjunctive to, or with, other anti-cancer therapies and/or targeted or non-targeted anti-cancer agents. When administered as an anti-4-1BB monotherapy, one or more antibodies may be used. Whether administered as monotherapy or adjunctive to, or with, other therapies or agents, an amount of anti-4-1BB antibody is administered such that the overall treatment regimen provides therapeutic benefit.

By therapeutic benefit is meant that the use of anti-4-1BB antibodies to treat cancer in a patient results in any demonstrated clinical benefit compared with no therapy (when appropriate) or to a known standard of care. Clinical benefit can be assessed by any method known to one of ordinary skill in the art. In one embodiment, clinical benefit is assessed based on objective response rate (ORR) (determined using RECIST version 1.1), duration of response (DOR), progression-free survival (PFS), and/or overall survival (OS). In some embodiments, a complete response indicates therapeutic benefit. In some embodiments, a partial response indicates therapeutic benefit. In some embodiments, stable disease indicates therapeutic benefit. In some embodiments, an increase in overall survival indicates therapeutic benefit. In some embodiments, therapeutic benefit may constitute an improvement in time to disease progression and/or an improvement in symptoms or quality of life. In other embodiments, therapeutic benefit may not translate to an increased period of disease control, but rather a markedly reduced symptom burden resulting in improved quality of life. As will be apparent to those of skill in the art, a therapeutic benefit may be observed using the anti-4-1BB antibodies alone (monotherapy) or adjunctive to, or with, other anti-cancer therapies and/or targeted or non-targeted anti-cancer agents.

Typically, therapeutic benefit is assessed using standard clinical tests designed to measure the response to a new treatment for cancer. To assess the therapeutic benefits of the anti-4-1BB antibodies described herein one or a combination of the following tests can be used: (1) the Response Evaluation Criteria In Solid Tumors (RECIST) version 1.1, (2) the Eastern Cooperative Oncology Group (ECOG) Performance Status, (3) immune-related response criteria (irRC), (4) disease evaluable by assessment of tumor antigens, (5) validated patient reported outcome scales, and/or (6) Kaplan-Meier estimates for overall survival and progression free survival.

Assessment of the change in tumor burden is an important feature of the clinical evaluation of cancer therapeutics. Both tumor shrinkage (objective response) and time to the development of disease progression are important endpoints in cancer clinical trials. Standardized response criteria, known as RECIST (Response Evaluation Criteria in Solid Tumors), were published in 2000. An update (RECIST 1.1) was released in 2009. RECIST criteria are typically used in clinical trials where objective response is the primary study endpoint, as well as in trials where assessment of stable disease, tumor progression or time to progression analyses are undertaken because these outcome measures are based on an assessment of anatomical tumor burden and its change over the course of the trial. TABLE 4 provides the definitions of the response criteria used to determine objective tumor response to a study drug, such as the anti-4-1BB antibodies described herein.

TABLE 4

| Response | Criteria |
| --- | --- |
| Complete Response (CR) | Disappearance of all target lesions. Any pathological lymph nodes (whether target or non-target) must have reduction in short axis to <10 mm. |
| Partial Response (PR) | At least a 30% decrease in the sum of diameters of target lesions, taking as reference the baseline sum diameters. |
| Progressive Disease (PD) | At least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). |
| Stable Disease (SD) | Neither sufficient shrinkage to qualify for PR nor sufficient increase to qualify for PD, taking as reference the smallest sum diameters while on study. |

The ECOG Scale of Performance Status shown in TABLE 5 is used to describe a patient's level of functioning in terms of their ability to care for themselves, daily activity, and physical ability. The scale was developed by the Eastern Cooperative Oncology Group (ECOG), now part of the ECOG-ACRIN Cancer Research Group, and published in 1982.

TABLE 5

| Grade | ECOG Performance Status |
| --- | --- |
| 1 | Restricted in physically strenuous activity but ambulatory and able to carry out work of a light or sedentary nature, e.g., light house work, office work |
| 2 | Ambulatory and capable of all selfcare but unable to carry out any work activities; up and about more than 50% of waking hours |
| 3 | Capable of only limited selfcare; confined to bed or chair more than 50% of waking hours |
| 4 | Completely disabled; cannot carry on any selfcare; totally confined to bed or chair |
| 5 | Dead |

Tumor antigens that can be used to evaluate the therapeutic benefit of the anti-4-1BB antibodies described herein include ApoE, CD1 lc, CD40, CD45 (PTPRC), CD49D (ITGA4), CD80, CSF1R, CTSD, GZMB, Ly86, MS4A7, PIK3AP1, PIK3CD, CD74, CCL5, CCR5, CXCL10, IFNG, IL10RA1, IL-6, ACTA2, COL7A1, LOX, LRRC15, MCPT8, MMP10, NOG, SERPINE1, STAT1, TGFBR1, CTSS, PGF, VEGFA, C1QA, C1QB, ANGPTL4, EGLN, ANGPTL4, EGLN3, BNIP3, AIF1, CCL5, CXCL10, CXCL11, IFI6, PLOD2, KISS1R, STC2, DDIT4, PFKFB3, PGK1, PDK1, AKR1C1, AKR1C2, CADM1, CDH11, COL6A3, CTGF, HMOX1, KRT33A, LUM, WNT5A, IGFBP3, MMP14, CDCP1, PDGFRA, TCF4, TGF, TGFB1, TGFB2, CD11b, ADGRE1 (EMR1, F4/80), CD86, CD68, MHC-Class II, CD3, HLA-DR, CD4, CD3, CD5, CD19, CD7, CD8, CD16, TCRαβ, TCRγδ, PD-1, PDL-1, CTLA-4, acid phosphatase, ACTH, alkaline phosphatase, alpha-fetoprotein, CA-125, CA15-3, CA19-9, CA-195, C-212, CA-549, calcitonin, catecholamines, cathepsin-D, CEA, ERBB2 (HER2/neu), chromagranin-A, c-Myc, EGFR, ERA (estrogen receptor assay), ferritin, gastrin, 5-HIAA, hCG, alpha-HCG, beta-HCG, HVA, LDH1-5, mesothelin, NSE (neuron specific enolase), pancreatic polypeptide, PLAP, PLP, PRA (progesterone receptor A), proinsulin C-peptide, PSA, SMA, SCC, thyroglobulin, TDT, TPA, and alpha-TSH. These antigens can be assessed at the DNA, RNA or protein level using DNA sequencing techniques, RNA sequencing techniques, gene chip microarray, PCR based methods, flow cytometry or immunohistochemistry methods as known to experts in the art.

Secondary outcome measures that can be used to determine the therapeutic benefit of the anti-4-1BB antibodies described herein include, Objective Response Rate (ORR), Progression Free Survival (PFS), Overall Survival (OS), Duration of Overall Response (DOR), and Depth of Response (DpR). ORR is defined as the proportion of the participants who achieve a complete response (CR) or partial response (PR). PFS is defined as the time from the first dose date of an anti-4-1BB antibody to either disease progression or death, whichever occurs first. OS is defined as the length of time from either the date of diagnosis or the start of treatment for a disease, that patients diagnosed with the disease are still alive. DOR is defined as the time from the participant's initial CR or PR to the time of disease progression. DpR is defined as the percentage of tumor shrinkage observed at the maximal response point compared to baseline tumor load. Clinical endpoints for both ORR and PFS can be determined based on RECIST 1.1 criteria described above.

Another set of criteria that can be used to characterize fully and to determine response to immunotherapeutic agents, such as antibody-based cancer therapies, is the immune-related response criteria (irRC), which was developed for measurement of solid tumors in 2009, and updated in 2013 (Wolchok, et al. Clin. Cancer Res. 2009; 15(23): 7412-7420 and Nishino, et al. Clin. Cancer Res. 2013;

19(14): 3936-3943). The updated irRC criteria are typically used to assess the effect of an immunotherapeutic agent, such as an anti-4-1BB antibody described herein, on tumor burden, and defines response according to TABLE 6.

TABLE 6

| Response | Criteria |
| --- | --- |
| Complete Response (CR) | Disappearance of all target lesions in two consecutive observations not less than 4 weeks apart |
| Partial Response (PR) | At least a 30% decrease in the sum of the longest diameters of target lesions, taking as reference the baseline sum diameters. |
| Progressive Disease (PD) | At least a 20% increase in the sum of diameters of target lesions, taking as reference the smallest sum on study (this includes the baseline sum if that is the smallest on study). (Note: the appearance of one or more new lesions is not considered progression. The measurement of new lesions is included in the sum of the measurements). |
| Stable Disease (SD) | Neither sufficient shrinkage to qualify for PR nor sufficient increase to qualify for PD, taking as reference the smallest sum diameters while on study. |

One exemplary therapeutic benefit resulting from the use of anti-4-1BB antibodies described herein to treat solid tumors, whether administered as monotherapy or adjunctive to, or with, other therapies or agents, is a complete response. Another exemplary therapeutic benefit resulting from the use of anti-4-1BB antibodies described herein to treat solid tumors, whether administered as monotherapy or adjunctive to, or with, other therapies or agents, is a partial response.

Validated patient reported outcome scales can also be used to denote response provided by each patient through a specific reporting system. Rather than being disease focused, such outcome scales are concerned with retained function while managing a chronic condition. One non-limiting example of a validated patient reported outcome scale is PROMIS® (Patient Reported Outcomes Measurement Information System) from the United States National Institutes of Health. For example, PROMIS® Physical Function Instrument for adult cancer patients can evaluate self-reported capabilities for the functioning of upper extremities (e.g., dexterity), lower extremities (e.g., walking or mobility), and central regions (e.g., neck, back mobility), and includes routine daily activities, such as running errands.

Kaplan-Meier curves (Kaplan and Meier, J. Am. Stat. Assoc. 1958; 53(282): 457-481) can also be used to estimate overall survival and progression free survival for cancer patients undergoing anti-4-1BB antibody therapy in comparison to standard of care.

7.6.2. Adjunctive Therapies

The anti-4-1BB antibodies may be used adjunctive to, or with, other agents or treatments having anti-cancer properties. When used adjunctively, the anti-4-1BB antibody and other agent(s) may be formulated together in a single, combination pharmaceutical formulation, or may be formulated and administered separately, either on a single coordinated dosing regimen or on different dosing regimens. Agents administered adjunctively with the anti-4-1BB antibodies will typically have complementary activities to the anti-4-1BB antibodies such that the antibodies and other agents do not adversely affect each other.

Agents that may be administered adjunctive to or with an anti-4-1BB antibody include, but are not limited to, alkylating agents, angiogenesis inhibitors, antibodies, antimetabolites, antimitotics, antiproliferatives, antivirals, aurora kinase inhibitors, apoptosis promoters (for example, Bcl-2 family inhibitors), activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin (mTor) inhibitors, microRNAs, mitogen-activated extracellular signal-regulated kinase inhibitors, non-steroidal anti-inflammatory drugs (NSAIDs), poly ADP (adenosine diphosphate)-ribose polymerase (PARP) inhibitors, platinum chemotherapeutics, Bruton's tyrosine kinase (BTK) inhibitors (e.g., ibrutinib, acalabrutinib), polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, as well as combinations of one or more of these agents.

Examples of immunologicals include, but are not limited to, interferons, immune checkpoint inhibitors, and other immune-enhancing agents. Interferons include interferon alpha, interferon alpha-2a, interferon alpha-2b, interferon beta, interferon gamma-1a, ACTIMMUNE® (interferon gamma-1b) or interferon gamma-nl, combinations thereof and the like. Immune check point inhibitors include antibodies that target PD-1 (e.g., pembrolizumab and nivolumab), PD-L1 (e.g., durvalumab, atezolizumab, avelumab, MEDI4736, MSB0010718C and MPDL3280A), and CTLA4 (cytotoxic lymphocyte antigen 4; e.g., ipilimumab, tremelimumab). Immune-enhancing agents include anti-OX40 agonist antibodies that activate T cells.

An anti-4-1BB antibody may also be used to enhance the efficacy of radiation therapy. Examples of radiation therapy include external beam radiation therapy, internal radiation therapy (i.e., brachytherapy) and systemic radiation therapy.

7.7. Dosages and Administration Regimens

The amount of anti-4-1BB antibodies administered will depend upon a variety of factors, including but not limited to, the particular type of solid tumor treated, the stage of the solid tumor being treated, the mode of administration, the frequency of administration, the desired therapeutic benefit, and other parameters such as the age, weight and other characteristics of the patient, etc. Determination of dosages effective to provide therapeutic benefit for specific modes and frequency of administration is within the capabilities of those skilled in the art.

Dosages effective to provide therapeutic benefit may be estimated initially from in vivo animal models or clinical trials. Suitable animal models for various diseases are known in the art.

The anti-4-1BB antibodies disclosed herein may be administered by any route appropriate to the condition to be treated. An anti-4-1BB antibody will typically be administered parenterally, i.e., infusion, subcutaneous, intramuscular, intravenous (IV), intradermal, intrathecal, bolus, intratumor injection or epidural ((Shire et al., 2004, *J Pharm. Sciences* 93(6):1390-1402)). In one embodiment, an anti-4-1BB antibody is provided as a lyophilized powder in a vial. Prior to administration, the lyophilized powder is reconstituted with sterile water for injection (SWFI) or other suitable medium to provide a solution containing an anti-4-1BB antibody. The resulting reconstituted solution is further diluted with saline or other suitable medium and administered via an IV infusion twice every 7 days, once every 7 days, once every 14 days, once every 21 days, once every 28 days, once every 35 days, once every 42 days, once every 49 days, or once every 56 days.

When administered adjunctive to, or with, other agents, such as other chemotherapeutic agents, the anti-4-1BB antibodies may be administered on the same schedule as the other agent(s), or on a different schedule. When administered on the same schedule, the anti-4-1BB antibody may be administered before, after, or concurrently with the other agent. In some embodiments where an anti-4-1BB antibody is administered adjunctive to, or with, standards of care, the anti-4-1BB antibody may be initiated prior to commencement of the standard therapy, for example a day, several days, a week, several weeks, a month, or even several months before starting standard of care therapy.

As will be appreciated by those of skill in the art, the recommended dosages for the various agents described above may need to be adjusted to optimize patient response and maximize therapeutic benefit.

8. EXAMPLES

The following Examples, which highlight certain features and properties of the exemplary embodiments of the anti-4-1BB antibodies described herein are provided for purposes of illustration, and not limitation.

Example 1: In Vitro Assays 8.1.1. 4-1BB NF-κB Reporter Assay

HEK293 cells previously transduced with the pLenti-NFκB-Luciferase vector was transfected with a plasmid expressing the human, cynomolgus, or mouse 4-1BB proteins using Lipofectamine 2000 (Invitrogen, Grand Island, N.Y., USA). Activation of 4-1BB on the surface of reporter cells triggers a signaling cascade leading to the activation of NF-κB and the subsequent expression of luciferase. Cells were thawed, resuspended at $5 \times 10^5$ cells/mL, and directly plated into 96-well format white/clear bottom plates (Thermo Fisher) at 50 μL/well (25,000 cells per well). A dose titration of purified antibody preparations were added in duplicate at 30, 10, 3.33, 1.11, 0.37, or 0.12 μg/mL at 50 μL/well. Crosslinkers were added in duplicate at 120, 40, 13.33, 4.44, 1.48, or 0.49 μg/mL or media at 50 μL/well. The following reagents were used as crosslinkers: Goat anti-mouse IgG Fc (Jackson Immunochemicals), Goat anti-human IgG Fc (Jackson Immunochemicals), or Goat anti-rat IgG Fc (Jackson Immunochemicals). Recombinant human (Abbvie, 6 μg/mL) or mouse 4-1BB Ligand (R&D, 6 μg/mL), TNFα (R&D, 60 ng/mL) or growth media were add to control wells for maximum and minimum luciferase activities for each of the cell lines. Assay plates were incubated overnight at 37° C. and luciferase activity was measured by relative luminescence (RLU) of the BriteLite Substrate (Perkin Elmer) at 75 μL/well. Data was plotted as percent ligand activity as follows:

% Relative activity=((RLU of sample−RLU of media)/(RLU of Ligand−RLU of media))×100.

8.1.2. 4-1BB FACS Binding

To determine species specificity and relative binding affinities of the test antibodies, cell lines were generated to exogenously express 4-1BB on the membrane. HEK293 cells were transfected with a plasmid expressing the human, cynomolgus, or mouse 4-1BB proteins. Stable, high expressing populations were sorted on the MoFlo sorter (Beckman) and maintained in DMEM, 10% fetal bovine serum, containing 500 μg/mL G418. For the assay, cells were dissociated with trypsin, resuspended at $5 \times 10^6$ cells/mL and transferred to the 500 μL polypropylene plate (Nunc) at 50 μL/well (250,000 cells/well). Test antibodies were added to appropriate wells of the assay plate at 20, 10, 5, 2.5, 1.25, 0.625, 0.312, 0.156, 0.078, 0.039, 0.0195, 0.00976 μg/mL (50 μL/well, singlets) and incubated at room temperature for 20 minutes. Cells were washed twice with 250 μL/PBS (Hyclone) per well. PE-labelled detection antibodies were added at 1:250 dilution of stock, 50 μL/well, and incubated for 20 minutes at room temperature. The following detection antibodies were used: Goat anti-Rat IgG-PE (Southern Biotech), Goat anti-Mouse IgG-PE (Southern Biotech) or Goat anti-Human IgG-PE (Southern Biotech). Cells were washed once and fixed with PBS containing 1% Formaldehyde. Plate was analyzed for fluorescence on the FACSCalibur (Becton Dickinson).

8.1.3. Surface Plasmon Resonance

The binding kinetics of the 4-1BB antibodies for target proteins were determined by using a Biacore T200 surface plasmon resonance system (BIAcore, GE Healthcare, Piscataway, N.J.). Polyclonal goat anti-human Fc antibody (Pierce 31125) was first immobilized to the biosensor surface using standard amine coupling reagents (N-ethyl-N'-dimethylamino-propylcarbodiimide, EDC; N-hydroxysuccinimide, NHS; and ethanolamine HCl, pH 8.5), followed by the capture of antibodies on parallel surfaces at a low flow rate of 10 μL/min. No capture of the antibody was made on the reference surface to serve as a negative control. Antigen (His-tagged ECD of 4-1BB derived from human, cynomolgus monkey, or mouse) was injected to all flow cells at a flow rate of 80 μL/min for three minutes to monitor association followed by a 10-20-minute flow of HBS-EP+running buffer (10 mM HEPES, 150 mM sodium chloride, 3 mM EDTA, 0.05% Tween-20, pH 7.5) to monitor the dissociation phase. At each cycle, four different concentrations of antigens ranging between 100 nM and 3.7 nM and at three-fold increments, were injected over the surface. The surface was regenerated by two consecutive injections of 10 mM glycine (pH 1.5) at a flow rate of 60 μL/min at the end of each cycle. Binding data were fit to the 1:1 Langmuir model to extract binding constants from the BIAevaluate software. Double referencing was applied in each analysis to eliminate background responses from the reference surface and buffer only control.

In addition to binding kinetics of two proteins, surface plasmon resonance can be used to determine binding competition as follows. The epitope grouping of test anti-4-1BB antibodies for recombinant soluble 4-1BB ECD (extracellular domain) was determined by competition assays using surface plasmon resonance-based measurements made on Biacore T200 instrument (GE Healthcare) using an anti-Fc capture assay approach. Chip preparation and competition measurements were made in the assay buffer HBS-EP+(10 mM Hepes, pH 7.4, 150 mM NaCl, 3 mM EDTA, 0.05% Tween 20). For anti-Fc capture chip preparation, approximately 2000 RU of goat anti-human IgG Fc polyclonal antibody (Thermo Fisher Scientific Inc., cat. No. 31125), diluted to 25 µg/mL in 10 mM sodium acetate (pH 4.5), was directly immobilized across a CMS biosensor chip using a standard amine coupling kit according to manufacturer's instructions and procedures. Unreacted moieties on the biosensor surface were blocked with ethanolamine. Binding competition measurements were made at 12° C. to slow the off-rates of antibody:antigen interactions. Each assay cycle consisted of the following steps: 1) capture of first test antibody at 10 µg/mL on test surface only; 2) blocking injection of isotype control cocktail at 100 µg/mL over both reference and test surface; 3) analyte injection (4-1BB ECD at 500 nM or buffer only) over both reference and test surface; 4) second test antibody injection at 10 µg/mL over both reference and test surface; 5) regeneration of capture surface by 10 mM Glycine-HCl, pH 1.5 injections over both reference and test surface. During the assay, all measurements were referenced against the capture surface alone (i.e. with no captured test antibody) and buffer-only injections were used for double referencing for each antibody pair individually. Binding of second test antibody was used as a reporter of simultaneous binding.

In a similar manner, the above protocol can be adapted to determine competition of a test anti-4-1BB antibody with 4-1BBL in solution.

8.1.4. 4-1BB Ligand Competition ELISA Assay

To evaluate the ability of the anti-4-1BB antibodies to compete with the 4-1BB ligand (4-1BBL) for binding, an ELISA assay was developed. Immunlon 4 plates (Dynatec) were coated with Goat anti-human IgG Fc specific at 0.5 µg/mL (Jackson Immunochemicals) in Carbonate-Bicarbonate buffer (Pierce), overnight at room temperature. Plates were washed and either mouse (R&D Systems) or human 4-1BB-Fc (R&D Systems) proteins were added at 0.2 µg/mL and incubated for 1 hour at room temperature. Plates were washed and the test antibodies were added as follows: 10, 5, 2.5, 1.25, 0.625, 0.3125, 0.156, 0.078, 0.039, 0.0195, 0.00976, or 0 µg/mL in duplicate and incubated for 1 hour at room temperature. Solution was then removed from the wells. Either human 4-1BBL (SEQ ID NO:2) (R&D Systems, at 0.02 µg/mL) or mouse 4-1BBL (R&D Systems, at 0.04 µg/mL) was added to respective wells and incubated for 1 hour at room temperature. Plates were washed and either biotinylated anti-human 4-1BBL (R&D Systems) or biotinylated anti-mouse 4-1BBL (R&D Systems) reagents were added at 0.05 µg/mL to detect the presence of 4-1BBL in the assay plates. Plates were washed and the complex was detected with Avidin-HRP (Jackson Immunochemicals) at 1:5000 dilution, incubated for 30 minutes at room temperature. Plates were washed and TMB Substrate (BioFx) was added to each well 100 µL/well. After 5 minutes of incubation, TMB Stop buffer (BioFx) was added at 50 µL/well. Plates were read at 650 nM on the Spectramax (Molecular Devices). Data was plotted as Percent Maximum (4-1BBL) binding as follows:

% Max Binding=$(OD_{650}$ of sample$)/(OD_{650}$ at 0 µg/mL antibody$)\times 100$.

8.1.5. CD8+ T cell Costimulation Assay

Human PBMC were purified from buffy coat by Ficoll-paque centrifugation and the CD8+ T cells were then purified from the PBMC using CD8+ T cells negative selection kit (StemCell Technologies). CD8+ T cells were resuspended in AIM-V medium. Antibodies were also prepared in this medium. A 96-well flat bottom plate was coated with 100 µL of 0.5 µg/mL OKT3 in PBS for 2 hr in the incubator, and the plate was washed twice with AIM-V. To the plate was added 50 µL CD8+ T cells ($2\times10^5$) per well, with 50 µL anti-4-1BB antibody (30 µg/mL or desired concentration gradient), and 50 µL goat anti-human IgG crosslinker (120 µg/mL or 4 times the amount of anti-4-1BB antibody used). The plates were incubated for 72 hr, after which 50 µL supernatant was taken for cytokine analysis by Luminex, including determination of interferon-gamma (IFN-γ) levels. To the plate was added 50 µL AIM-V/0.5 µCi $^3$H per well and the mixtures incubated for 6 hr to measure $^3$H-thymidine incorporation (proliferation). Costimulation can be measured as a function of proliferation (i.e., change in thymidine incorporation) or modulation of downstream cytokine levels (e.g., increase in IFN-γ).

Alternatively, with CHOK1-FcγR transfectants or PC3-MSLN as crosslinker, irradiated cells ($2\times10^4$/well) were placed in a 96-well plate in complete medium the day before experiment. CD8+ T cells and antibody gradient were prepared in AIM-V medium. The medium in the wells was replaced with 100 µL CD8+ T cells ($2\times10^5$/well) and 100 µL anti-4-1BB antibody containing 1 µg/mL OKT3. The plates were incubated, and analysis for cytokine release and proliferation was performed as above.

Example 2: Generation and Characterization of Exemplary Anti-4-1BB Antibodies 8.2.1. Anti-4-1BB Antibodies via Rat and Mouse Hybridoma Technology Rats and mice were immunized according to the methods known in the art (E. Harlow, D. Lane. Antibody: A Laboratory Manual, (Cold Spring Harbor Laboratory Press, Cold Spring Harbor, N.Y., 1998)). Recombinant mouse 4-1BB-ECD-human Fc fusion or mouse 4-1BB-ECD-his proteins were used as immunogens. Human cell lines expressing human and mouse 4-1BB were used for determining anti-sera titer and for screening antigen-specific antibodies. Sprague-Dawley rats were immunized in the hock with dosages containing 10 µg protein per animal per injection in the presence of Gerbu MM adjuvant (Cooper-Casey Corporation) for both primary and boost immunizations. To increase immune response to the counter species 4-1BB, the animals were further boosted with a mixture of human and mouse 4-1BB-ECD-his proteins for the final boosts.

8.2.2. Hybridoma Fusion and Screening

Cells of murine myeloma cell line NSO were cultured to reach the log phase stage right before fusion. Popliteal and inguinal lymph nodes were removed from each mouse and single cell suspensions were prepared sterilely. Lymphocytes were fused with myeloma cells according the methods known in the art (E. Harlow, D. Lane. Antibody: A Laboratory Manual, (Cold Spring Harbor Laboratory Press, Cold Spring Harbor, N.Y., 1998); Kohler G. and Milstein C., Nature, 256:495-497 (1975); BTX Harvard Apparatus (Holliston, Mass., US) ECM 2001 technical manual). Fused hybrid cells were dispensed into 96-well plates in DMEM/10% FBS/HAT media. Supernatants from surviving hybridoma colonies were subjected to cell-based screening using human cell lines expressing the recombinant human 4-1BB or mouse 4-1BB.

Hits were expanded and binding specificity was confirmed by FACS using a human cell line expressing the human 4-1BB, cynomolgus 4-1BB, and mouse 4-1BB and Goat anti-rat IgG-PE (Jackson Immunochemicals) or Goat anti-mouse IgG-PE (Jackson Immunochemicals) for detection. A selection of hits were subcloned using the MoFlo (Beckman) by depositing a single cell per well into 96-well cell culture plates to ensure clonality of the cell line. Resulting colonies were screened for specificity by FACS using human cell lines expressing the human 4-1BB protein, cynomolgus 4-1BB or mouse 4-1BB. Isotype of each monoclonal antibody was determined using the Rat Monoclonal Isotyping kit (Serotec) or the Mouse Isotyping kit (Roche). Hybridoma clones producing antibodies of interest were purified and further characterized for affinity by surface plasmon resonance, potency (NFκB reporter assay), and ligand competition (ELISA).

Exemplary antibodies to murine 4-1BB were generated, and the amino acid sequences for the corresponding $V_H$ and $V_L$ sequences are shown in FIGS. 2A-2C. Binding of exemplary antibodies to endogenous human 4-1BB, as well as their respective $EC_{50}$s, was determined by surface plasmon resonance as described in Section 8.1.3.

The rat antibodies TABBY101 through TABBY108, displaying either a rat IgG1 or rat $IgG_{2a}$ constant region, all exhibited binding to murine 4-1BB (mu4-1BB) as demonstrated by the surface plasmon resonance (Biacore) described in Section 8.1.3 with the results as shown in Table 2-1 below.

TABLE 2-1

Binding of rat antibodies to murine 4-1BB by Biacore

| Antibody | Light chain | mu4-1BB $K_D$ (nM) |
|---|---|---|
| TABBY101-$rIgG_1$ | kappa | 0.82 |
| TABBY102-$rIgG_1$ | kappa | 0.84 |

TABLE 2-1

Binding of rat antibodies to murine 4-1BB by Biacore

| Antibody | Light chain | mu4-1BB $K_D$ (nM) |
|---|---|---|
| TABBY103-$rIgG_1$ | kappa | 0.17 |
| TABBY104-$rIgG_1$ | kappa | 0.14 |
| TABBY105-$rIgG_{2a}$ | kappa | 15 |
| TABBY106-$rIgG_1$ | lambda | 1.6 |
| TABBY107-$rIgG_1$ | kappa | 6.7 |
| TABBY108-$rIgG_1$ | kappa | 0.36 |

Additionally, the murine antibodies TABBY1.1 through TABBY10, displaying either a mouse $IgG_1$ or $IgG_{2b}$ constant region, exhibited binding to human 4-1BB (hu4-1BB) by Biacore as shown in Table 2-2.

TABLE 2-2

Binding of murine antibodies to human 4-1BB by Biacore

| Antibody | hu4-1BB $K_D$ (nM) |
|---|---|
| TABBY1.1-$mIgG_1$ | 2.0 |
| TABBY3-$mIgG_{2b}$ | 6.6 |
| TABBY5-$mIgG_{2b}$ | 0.3 |
| TABBY6-$mIgG_1$ | 1.9 |
| TABBY10-$mIgG_1$ | 3.1 |

Table 2-3 shows that the rat anti-4-1BB antibodies TABBY106 and TABBY107 exhibit a different binding profile than literature anti-4-1BB antibodies 3H3 and 1D8. In contrast to 3H3 and 1D8, the presently disclosed antibodies show binding to human 4-1BB. The anti-4-1BB antibodies TABBY106 and TABBY107 also bind to murine 4-1BB.

TABLE 2-3

Binding kinetics of exemplary antibodies to human and mouse 4-1BB*

| | Human 4-1BB | | | Mouse 4-1BB | | |
|---|---|---|---|---|---|---|
| Antibody | $k_a$ (1/M-s) | $k_d$ (1/s) | $K_D$ (M) | $k_a$ (1/M-s) | $k_d$ (1/s) | $K_D$ (M) |
| 3H3 | Not detected | | | 5.8E+06 | 5.7E−03 | 9.8E−10 |
| 1D8 | Not detected | | | 2.1E+06 | 8.0E−03 | 3.9E−09 |
| TABBY106-$rIgG_1$ | 2.2E+06 | 2.6E−02 | 1.2E−08 | 8.1E+06 | 1.3E−02 | 1.6E−09 |
| TABBY107-$rIgG_1$ | 4.5E+05 | 1.4E−04 | 3.2E−10 | 2.4E+05 | 1.6E−03 | 6.7E−09 |

*Values refer to exponential notation, e.g., 3.0E−09 = 3.0 × $10^{-9}$.

Additionally, the exemplary anti-4-1BB antibodies TABBY106 and TABBY107 also bind to cynomolgus 4-1BB in contrast to the literature anti-4-1BB antibodies 3H3 and 1D8 that do not exhibit significant binding. The results are summarized in Table 2-4.

TABLE 2-4

Binding kinetics of exemplary antibodies to cynomolgus 4-1BB*

| | Cynomolgus 4-1BB | | |
|---|---|---|---|
| Antibody | $k_a$ (1/M-s) | $k_d$ (1/s) | $K_D$ (M) |
| 3H3 | Not detected | | |
| 1D8 | Not detected | | |
| TABBY106-$rIgG_1$ | 1.2E+06 | 2.2E−02 | 1.8E−08 |
| TABBY107-$rIgG_1$ | 3.5E+05 | 1.3E−04 | 3.6E−10 |

*Values refer to exponential notation, e.g., 3.0E−09 = 3.0 × $10^{-9}$.

The rat antibodies TABBY101 through TABBY108 were tested for competitive binding with human 4-1BB ligand against human 4-1BB according to the ELISA competition assay described in Section 8.1.4. None of the antibodies competed with human 4-1BB ligand for binding to human 4-1BB.

Anti-4-1BB rat antibodies TABBY106 and TABBY107 were humanized according to methods known in the art to provide humanized antibodies having variable heavy and light chains shown in FIG. 2D. Antibody variable regions were humanized using a structure-guided method as described by Queen et al. (Proc. Natl. Acad. Sci. USA, 1989; 86:10029-10033). Human V region frameworks to be used as acceptors for rodent CDR regions were chosen based on sequence homology, and a homology model of the variable region was constructed in silico. Amino acids in the V regions predicted to have contact with the CDR regions were substituted with the corresponding residues of the rodent antibody where different. Both hu106-1-$hIgG_1$ and hu107-1-$hIgG_1$ display $huIgG_1$ constant regions bearing L234A and L235A substitutions. Hu106-1-$hIgG_1$ has a heavy chain sequence according to SEQ ID NO:310 or 311, and a light chain sequence according to SEQ ID NO:314. Hu107-1-$hIgG_1$ has a heavy chain sequence according to SEQ ID NO:312 or 313, and a light chain sequence according to SEQ ID NO:315.

Humanized antibody hu107-1-$hIgG_1$ showed a similar binding profile by surface plasmon resonance (Tables 2-5 and 2-6) compared with that of TABBY107-$rIgG_1$.

TABLE 2-5

Humanized anti-4-1BB antibody binding kinetics*

| | Human 4-1BB | | | Mouse 4-1BB | | |
|---|---|---|---|---|---|---|
| Antibody | $k_a$ (1/M-5) | $k_d$ (1/s) | $K_D$ (M) | $k_a$ (1/M-s) | $k_d$ (1/s) | $K_D$ (M) |
| hu106-1-hIgG$_1$ | 5.7E+05 | 7.4E−02 | 1.3E−07 | 2.2E+06 | 3.6E−02 | 1.7E−08 |
| hu106-4-hIgG$_4$ | 2.1E+05 | 4.2E−02 | 2.0E−07 | 1.6E+06 | 1.5E−02 | 9.3E−09 |
| hu106-7-hIgG$_4$ | 1.1E+05 | 4.7E−02 | 4.2E−07 | 2.2E+06 | 3.7E−02 | 1.7E−08 |
| hu107-1-hIgG$_1$ | 4.1E+05 | 6.5E−05 | 1.6E−10 | 2.4E+05 | 1.3E−03 | 5.2E−09 |
| hu107-1-hIgG$_4$ | 1.4E+05 | 8.0E−05 | 5.8E−10 | 3.3E+05 | 1.3E−03 | 4.0E−09 |
| hu107-3-hIgG$_4$ | 1.3E+05 | 1.1E−04 | 8.1E−10 | 3.2E+05 | 1.6E−03 | 5.1E−09 |
| 20H4.9-hIgG$_4$ | 4.2E+05 | 2.1E−03 | 4.9E−09 | | Not detected | |
| MOR-7480.1-hIgG$_2$ | 8.4E+05 | 1.2E−02 | 1.5E−08 | | Not detected | |

*Values refer to exponential notation, e.g., 3.0E−09 = 3.0 × 10$^{-9}$;
hIgG$_1$ antibodies above displayed constant regions with L234A and L235A mutations;
hIgG$_4$ antibodies above displayed constant regions with the S228P mutation.

TABLE 2-6

Humanized anti-4-1BB antibody binding kinetics to cyno 4-1BB*

| | Cynomolgus 4-1BB | | |
|---|---|---|---|
| Antibody | $k_a$ (1/M-s) | $k_d$ (1/s) | $K_D$ (M) |
| hu106-1-hIgG$_1$ | 6.2E+05 | 1.0E−01 | 1.7E−07 |
| hu106-4-hIgG$_4$ | 2.8E+05 | 5.2E−02 | 1.8E−07 |

TABLE 2-6

Humanized anti-4-1BB antibody binding kinetics to cyno 4-1BB*

| | Cynomolgus 4-1BB | | |
|---|---|---|---|
| Antibody | $k_a$ (1/M-s) | $k_d$ (1/s) | $K_D$ (M) |
| hu106-1-hIgG$_4$ | 1.7E+05 | 5.6E−02 | 3.3E−07 |
| hu107-1-hIgG$_1$ | 3.1E+05 | 4.0E−05 | 1.3E−10 |
| hu107-1-hIgG$_4$ | 2.4E+05 | 5.2E−05 | 2.2E−10 |
| hu107-3-hIgG$_4$ | 2.4E+05 | 7.0E−05 | 2.9E−10 |
| 20H4.9-hIgG$_4$ | | Not detected | |
| MOR-7480.1-hIgG$_2$ | 8.6E+05 | 2.6E−02 | 3.0E−08 |

*Values refer to exponential notation, e.g., 3.0E−09 = 3.0 × 10$^{-9}$; hIgG$_1$ antibodies above displayed constant regions with L234A and L235A mutations; hIgG$_4$ antibodies above displayed constant regions with the S228P mutation.

Additionally, the anti-4-1BB antibodies disclosed herein showed different cross-reactivity as compared to known anti-4-1BB antibodies. In an illustrative example, reference antibodies 20H4.9-hIgG$_4$ (see, e.g., U.S. Pat. No. 8,137,660) and MOR-7480.1-hIgG$_2$ (see, e.g., US Publication No. 20140178368) did not show any cross-reactivity to mouse 4-1BB (Table 2-5). MOR-7480.1-hIgG$_2$ showed cross-reactivity to cynomolgus 4-1BB but 20H4.9-hIgG$_4$ did not exhibit binding (Table 2-6). By contrast, humanized antibodies derived from TABBY106 and 107 showed binding to both murine and cynomolgus 4-1BB, and thus retained cross-reactivity among species after humanization (Tables 2-5 and 2-6).

The ability to cross-react with different species can be useful to monitor safety for immuno-oncology drug candidates which can cause severe adverse events. It has been reported that an agonistic 4-1BB antibody can cause hepatic toxicity in humans. See, e.g., Yonezawa, A. et al. Clinical Cancer Research, 21 (14); 3113-3120 (2015). Hence, it may be necessary to monitor safety signals such as the levels of certain liver enzymes. With the anti-4-1BB antibodies described herein, potential liver toxicity can be addressed at an early stage, e.g., by monitoring ALT levels in a preclinical mouse model as described in Examples 6 and 7 below and shown in FIGS. 7 and 9.

8.2.3. Epitope Binding Studies

In a surface plasmon resonance assay as described in Section 8.1.3, chimeric antibodies TABBY106 and TABBY107, both exhibiting a human IgG$_1$ constant region, showed a lack of competitive binding with 4-1BBL to 4-1BB (Table 2-7). By contrast, MOR-7480.1-hIgG$_2$ competed with 4-1BBL for binding 4-1BB. Additionally, TABBY106 and TABBY107 did not compete with 20H4.9-hIgG4, but did compete with MOR-7480.1-hIgG$_2$, for binding to 4-1BB.

TABLE 2-7

Binding Competition of Soluble Protein with Surface
Bound Antibody-4-1BB Complex
Simultaneous binding to 4-1BB measured by Biacore*

| | In solution | | | | |
|---|---|---|---|---|---|
| On surface | MOR-7480.1-hIgG$_2$ | 20H4.9-hIgG$_4$ | TABBY106-hIgG$_1$ | TABBY107-hIgG$_1$ | 4-1BBL |
| MOR-7480.1-hIgG$_2$ | X | Y | X | X | X |
| 20H4.9-hIgG$_4$ | Y | X | Y | Y | Y |
| TABBY106-hIgG$_1$ | X | Y | X | X | Y |
| TABBY107-hIgG$_1$ | X | Y | X | X | Y |

*X = competition observed; Y = simultaneous binding (no competition) observed.

Example 3: T-cell Proliferation Effects of Anti-4-1BB Antibodies

Exemplary chimeric anti-4-1BB antibodies TABBY106 and TABBY107 generated with rat variable regions and a human IgG4 constant region (i.e., TABBY106-hIgG$_4$ and TABBY107-hIgG$_4$, respectively) showed FcγR-dependent proliferation effects.

FIG. 3 depicts the effects of TABBY106-hIgG$_4$ or TABBY107-hIgG$_4$ on T-cell co-cultures with CHOK1 cells with or without expression of an Fcγ receptor as compared with a human IgG$_4$ isotype control (AB095). Anti-CD3 antibody and the anti-4-1BB antibody were added in solution. Upper left panel depicts the effects of TABBY106-hIgG$_4$ or TABBY107-hIgG$_4$ in CHOK1 cell co-cultures without Fcγ receptor expression. The anti-4-1BB antibodies did not show significantly different proliferation effects compared with isotype control.

CHOK1 cell co-cultures expressing an Fcγ receptor exhibited significantly higher proliferation when dosed with anti-4-1BB antibodies compared with isotype control as shown in FIG. 3. CHOK1 cell co-cultures expressing CD32A (FcγRIIA) (upper right), CD32B (FcγRIIB) (lower left), or CD64 (FcγRI) (lower right) dosed with an anti-4-1BB antibody TABBY106-hIgG$_4$ or TABBY107-hIgG$_4$ demonstrated significantly higher T cell proliferation compared with the same dose of the control.

Example 4: Anti-4-1BB Antibody IgG Constant Regions Affect T-cell Stimulation Levels Additional chimeric antibodies were generated with the rat variable regions described above, and constant regions from human IgG$_1$, IgG$_2$, and IgG$_4$, as well as variant constant regions, such as IgG$_1$ with the V273E substitution. The differences in constant regions in anti-4-1BB antibodies afforded differing biological characteristics, such as altered T-cell stimulation results in a human CD8+ T-cell stimulation assay according to Section 8.1.5. Results for exemplary anti-4-1BB antibodies TABBY106 and TABBY107 are shown in FIG. 4.

Figure 4A:
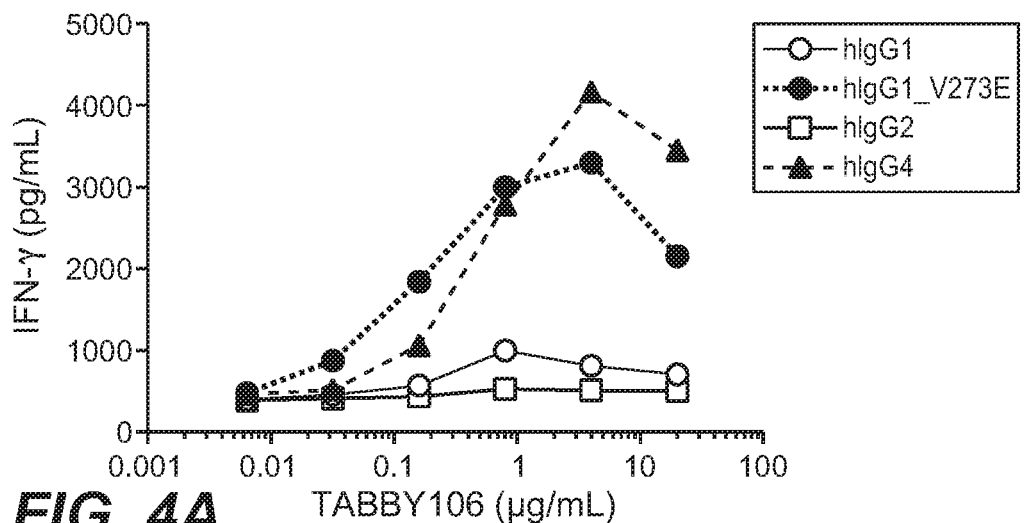
Figure 4B:
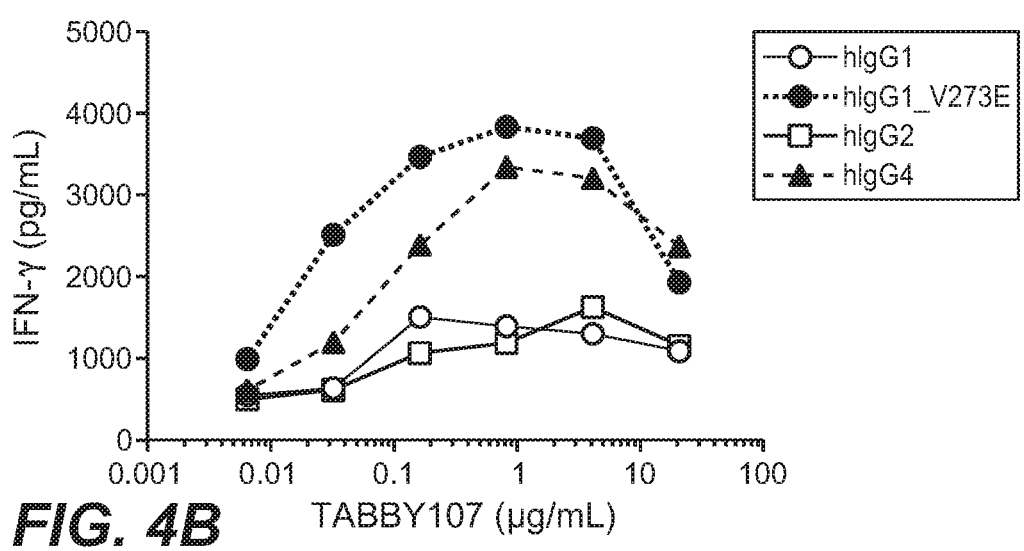

FIGS. 4A-4B show the concentration effect of chimeric antibodies TABBY106 (FIG. 4A) or TABBY107 (FIG. 4B), with rat variable domains and displaying the human constant regions as indicated in the legend (IgG$_1$, IgG$_1$ V273E, IgG$_2$, or IgG$_4$), on production of interferon-gamma (IFN-γ) in T-cells. For both TABBY106 and TABBY107, the human IgG$_4$ and human IgG$_1$ V273E constant regions afforded the highest T-cell stimulation as measured by IFN-γ production. By contrast, TABBY106 or TABBY107 with either human IgG$_1$ or human IgG$_2$ showed a lower level of T cell costimulation activity.

The exemplary anti-4-1BB antibodies TABBY106 and TABBY107 described herein exhibited a unique binding profile that provided the observed biochemical activities. For instance, neither antibody significantly competed with natural ligand 4-1BBL (SEQ ID NO:2).

As shown above, TABBY106 and TABBY107 demonstrated T-cell stimulation effects in the presence of a second antibody crosslinker under standard T-cell stimulation assay conditions. However, the two anti-4-1BB antibodies did not exhibit significant T-cell stimulation in the absence of a crosslinker. Further, in addition to the T-cell proliferation effects shown in Example 3, TABBY106 and TABBY107 also exhibited human CD8+ T-cell stimulation effects in CHO cells expressing FcγRIIB.

Chimeric antibodies having V$_H$ and V$_L$ chains of TABBY106 and TABBY107 were also compared with known anti-4-1BB antibodies 20H4.9-hIgG$_4$ (see, e.g., U.S. Pat. No. 8,137,667) and MOR-7480.1-hIgG2 (see, e.g., PCT publication WO 2012/145183) produced from transient transfection of HEK293 cells. The heavy and light chain amino acid sequences, respectively, for 20H4.9-hIgG4 were:

```
                                        (SEQ ID NO: 301)
QVQLQQWGAGLLKPSETLSLTCAVYGGSFSGYYWSWIRQSPEKGLEWIG

EINHGGYVTYNPSLESRVTISVDTSKNQFSLKLSSVTAADTAVYYCARD

YGPGNYDWYFDLWGRGTLVTVSSASTKGPSVFPLAPCSRSTSESTAALG

CLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKS

LSLSLGK,
and (SEQ ID NO: 302)
EIVLTQSPATLSLSPGERATLSCRASQSVSSYLAWYQQKPGQAPRLLIY

DASNRATGIPARFSGSGSGTDFTLTISSLEPEDFAVYYCQQRSNWPPAL

TFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYAC

EVTHQGLSSPVTKSFNRGEC.
```

The heavy and light chain amino acid sequences, respectively, for MOR-7480.1-hIgG$_2$ were:

```
                                        (SEQ ID NO: 303)
EVQLVQSGAEVKKPGESLRISCKGSGYSFSTYWISWVRQMPGKGLEWMG

KIYPGDSYTNYSPSFQGQVTISADKSISTAYLQWSSLKASDTAMYYCAR

GYGIFDYWGQGTLVTVSSASTKGPSVFPLAPCSRSTSESTAALGCLVKD

YFPEPVTVSWNSGALTSGVHTFPAVLQSSGLYSLSSVVTVPSSNFGTQT

YTCNVDHKPSNTKVDKTVERKCCVECPPCPAPPVAGPSVFLFPPKPKDT

LMISRTPEVTCVVVDVSHEDPEVQFNWYVDGVEVHNAKTKPREEQFNST

FRVVSVLTVVHQDWLNGKEYKCKVSNKGLPAPIEKTISKTKGQPREPQV

YTLPPSREEMTKNQVSLTCLVKGFYPSDIAVEWESNGQPENNYKTTPPM

LDSDGSFFLYSKLTVDKSRWQQGNVFSCSVMHEALHNHYTQKSLSLSPG

K,
and (SEQ ID NO: 304)
SYELTQPPSVSVSPGQTASITCSGDNIGDQYAHWYQQKPGQSPVLVIYQ

DKNRPSGIPERFSGSNSGNTATLTISGTQAMDEADYYCATYTGFGSLAV

FGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQ

VTHEGSTVEKTVAPTECS.
```

Figure 4C:
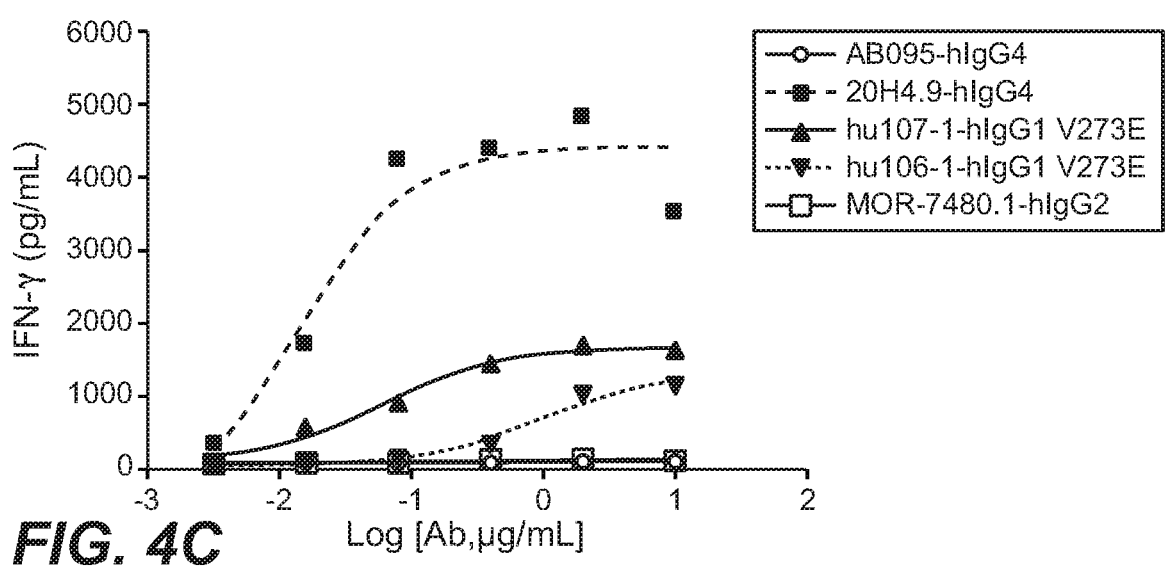

Reference antibodies 20H4.9-hIgG$_4$ and MOR-7480.1-hIgG$_2$ were compared along with TABBY106-hIgG$_1$ V273E and TABBY107-hIgG$_1$ V273E in the human CD8+ T cell costimulation assay of Section 8.1.5 in the presence of CD32B (FIG. 4C). Antibody 20H4.9-hIgG$_4$ was significantly potent on T-cell costimulation while little activity was observed with dosing of MOR-7480.1. Chimeric antibodies TABBY106-hIgG$_1$ V273E and TABBY107-hIgG$_1$ V273E were not as potent as 20H4.9-hIgG4 but showed higher activity than MOR-7480.1-hIgG$_2$.

Example 5: In Vivo Antitumor Activity of Exemplary Anti-4-1BB Antibodies

Enhanced T cell effects afforded by exemplary agonistic anti-4-1BB antibodies shown herein correlated with in vivo antitumor activity in mouse tumor models. For example, the anti-4-1BB antibodies showed an inhibition of tumor growth in Balb/c mice bearing CT26 tumors. Such cancer tumor animal models are well-known in the art. See, e.g., James, E. et al. Journal of Immunology, 185 (9), 5048-5055 (2010), for an exemplary CT26 Balb/c mouse model protocol.

Figure 5:
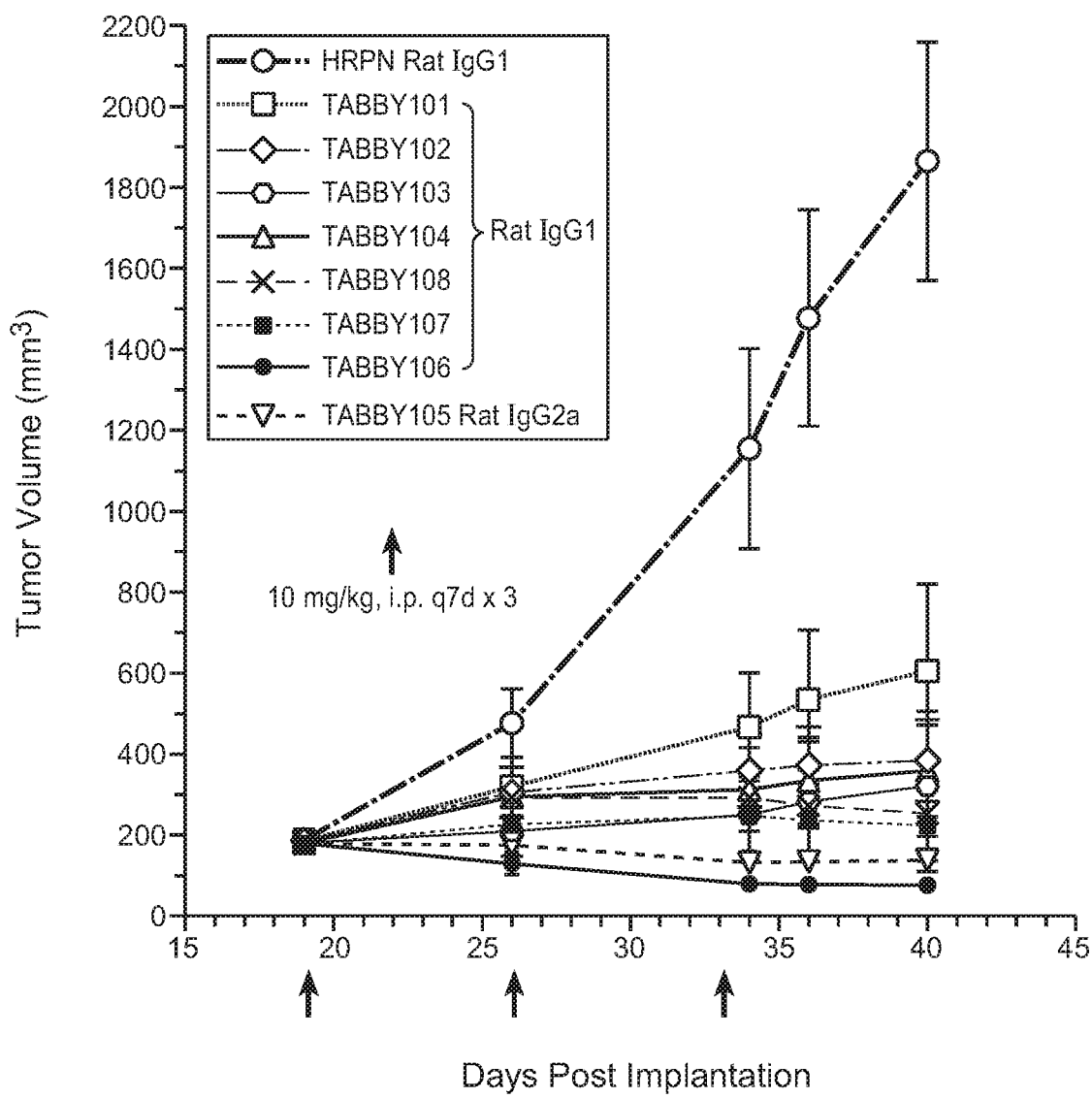
FIG. 5 shows the volume of CT26 colon carcinoma tumors in Balb/c mice after dosing at 10 mg/kg intraperitoneally once every seven days for a total of three doses with exemplary anti-4-1BB antibodies derived from rat hybridoma.

Antitumor effects of exemplary anti-4-1BB antibodies are shown in FIG. 5. As compared with isotype control rat IgG1 antibody ("HRPN rat G1"), the anti-4-1BB antibodies TABBY101-rIgG$_1$, TABBY102-rIgG$_1$, TABBY103-rIgG$_1$, TABBY104-rIgG$_1$, TABBY105-rIgG$_{2a}$, TABBY106-rIgG$_1$, TABBY107-rIgG$_1$, and TABBY108-rIgG$_1$ inhibited the growth of CT26 colorectal adenocarcinoma cells in Balb/c mice at 10 mg/kg dosed intraperitoneally (IP) q7d×3 (i.e., once every seven days for a total of three doses).

Figure 6:
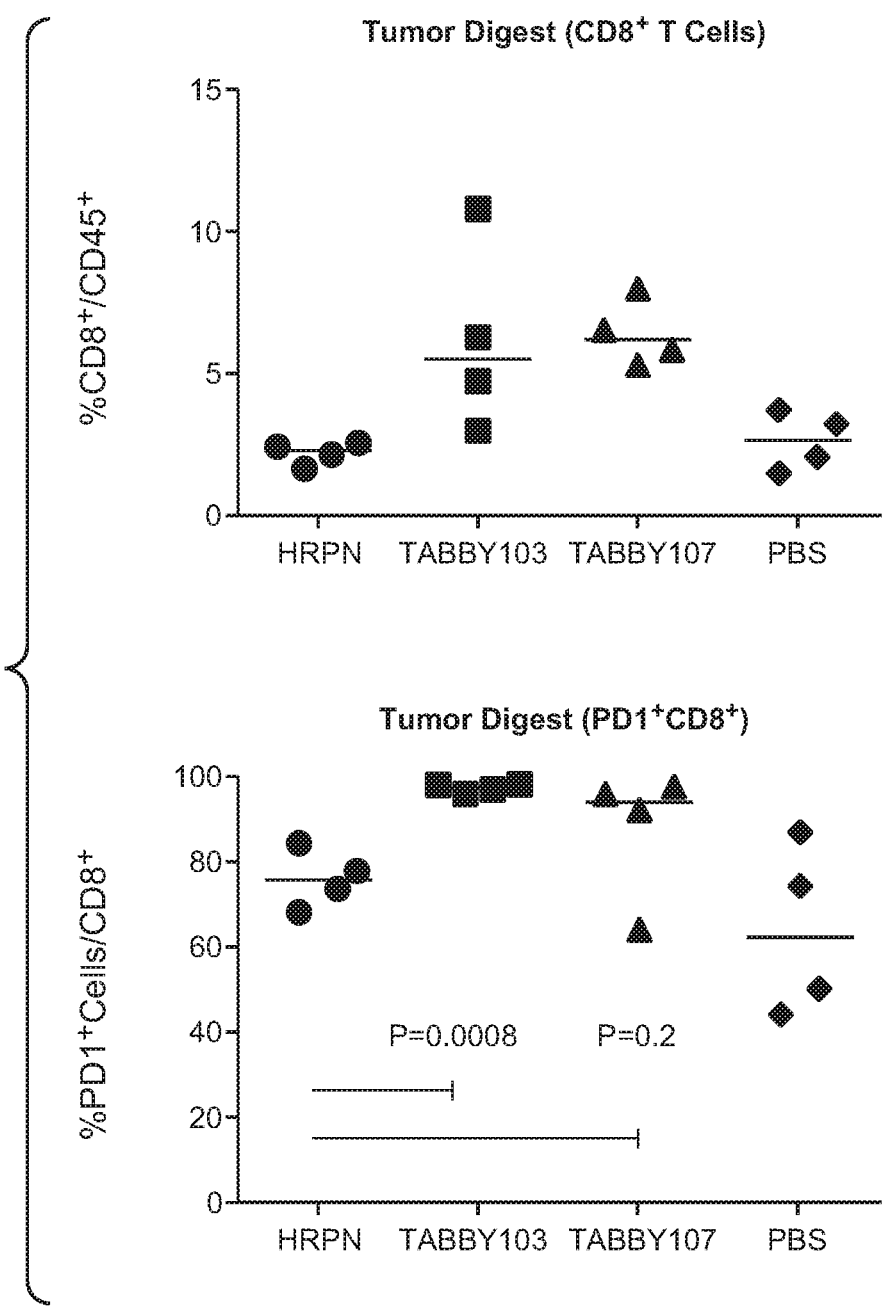
FIG. 6 shows the CD8+ T cell population after in vivo dosing of an exemplary anti-4-1BB antibody in Balb/c mice bearing CT26 tumors. Left graph shows the number of CD8+ T cells as a percentage of CD45+ cells; right graph shows the number of PD-1+ cells as a percentage of CD8+ T cells.

The antitumor efficacy correlated with an increase in the number of CD8+ T cells and a change in the type of T cells that were present in the tumors (FIG. 6). After the first two doses at Day 0 and at Day 7, a sample of tumor was extracted on Day 8 and digested to determine if the proportion and type of CD8+ T cells had changed upon dosing with an anti-4-1BB antibody. As shown in FIG. 6 (left graph), the percentage of CD8+ T cells within the tumor (measured as a percentage of all CD45+ cells) increased compared to isotype antibody or PBS controls. Additionally, a statistically significant increase in the number of PD1+ cells as a fraction of total CD8+ T cells was observed in comparison to isotype antibody or PBS dosing (right graph).

Example 6: Anti-4-1BB Antibodies Show Low Liver Toxicity Effects

Figure 7:
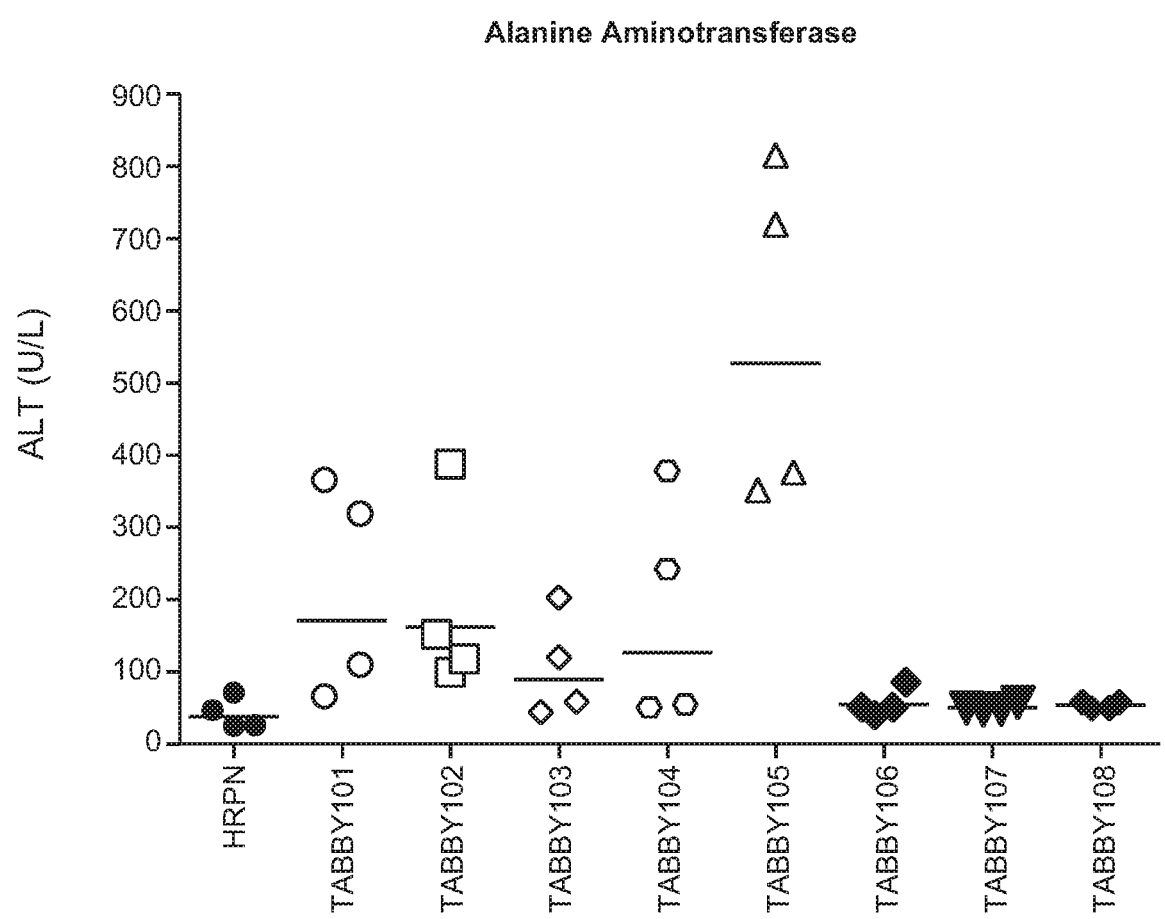
FIG. 7 shows alanine aminotransferase (ALT) levels in the serum of Balb/c mice bearing CT26 tumors after the third dose of an exemplary rat anti-4-1BB antibody or control (HRPN).

Exemplary rat anti-4-1BB antibodies did not show elevated liver enzyme alanine aminotransferase (ALT) levels after completion of the third dose in the dosing protocol that resulted in antitumor activity as described in Example 5. TABBY106-rIgG$_1$, TABBY107-rIgG$_1$, and TABBY108-rIgG$_1$ did not show significant elevation of ALT levels (FIG. 7).

Figure 8:
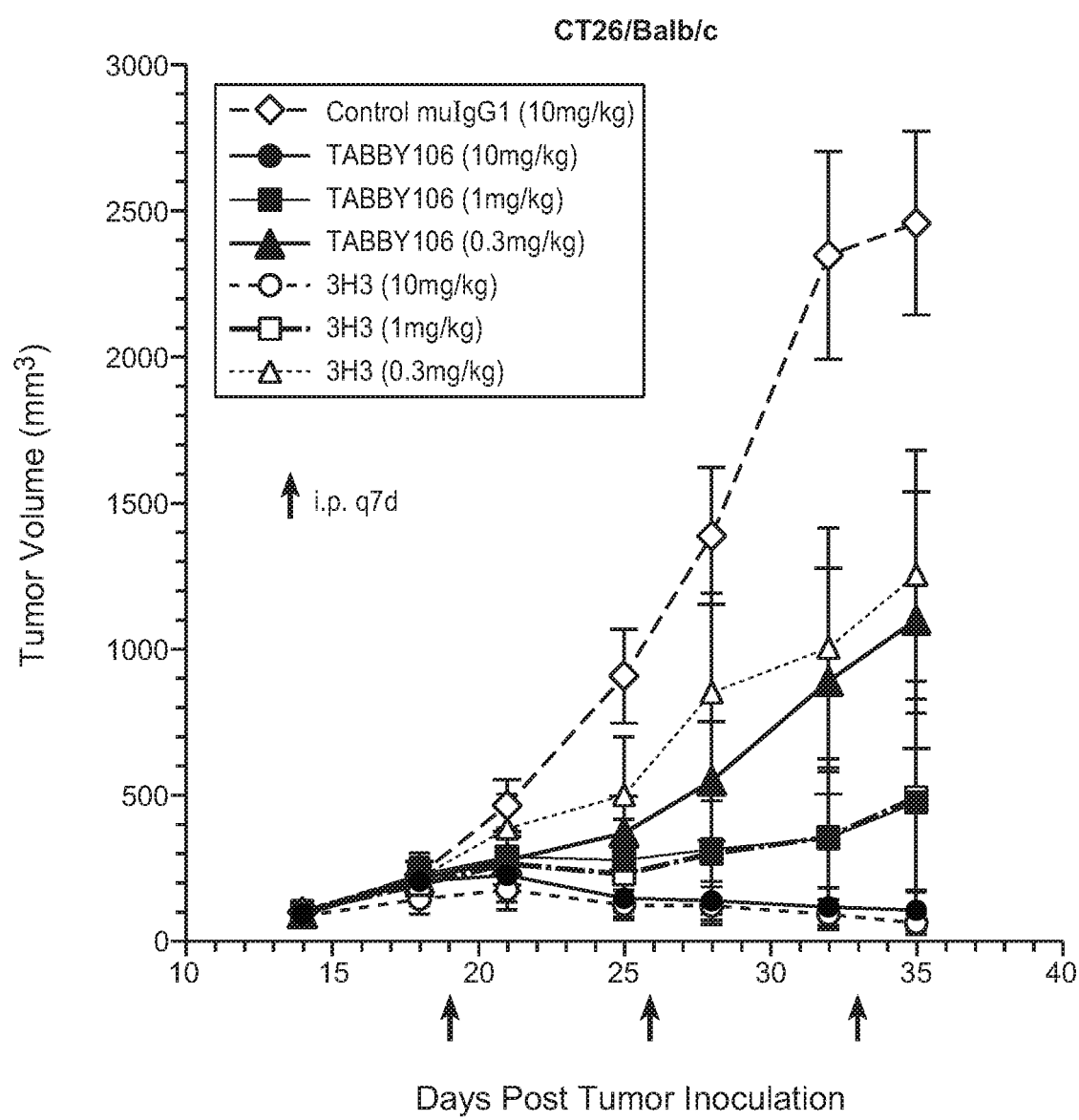
FIG. 8 shows the volume of CT26 tumors in Balb/c mice after dosing with 0.3, 1, or 10 mg/kg of anti-4-1BB antibody 3H3-ratIgG$_{2a}$ or chimeric antibody TABBY106-muIgG$_1$ intraperitoneally once every seven days for a total of three doses.

Example 7: Anti-4-1BB Antibody TABBY106 Shows Lower Liver Toxicity than Comparable Antibody In addition to the potent antitumor effects shown above, TABBY106 also demonstrated dose-dependent pharmacological effects in Balb/c mice bearing CT26 tumors. FIG. 8 depicts the results showing that TABBY106-muIgG$_1$, i.e., having the rat variable domains and murine IgG$_1$ constant region, had a dose-dependent antitumor effect comparable to literature anti-4-1BB antibody 3H3 in inhibiting growth of CT26 tumors in Balb/c mice at 0.3, 1, or 10 mg/kg dosed intraperitoneally q7d×3 (i.e., once every seven days for a total of three doses).

Figure 9:
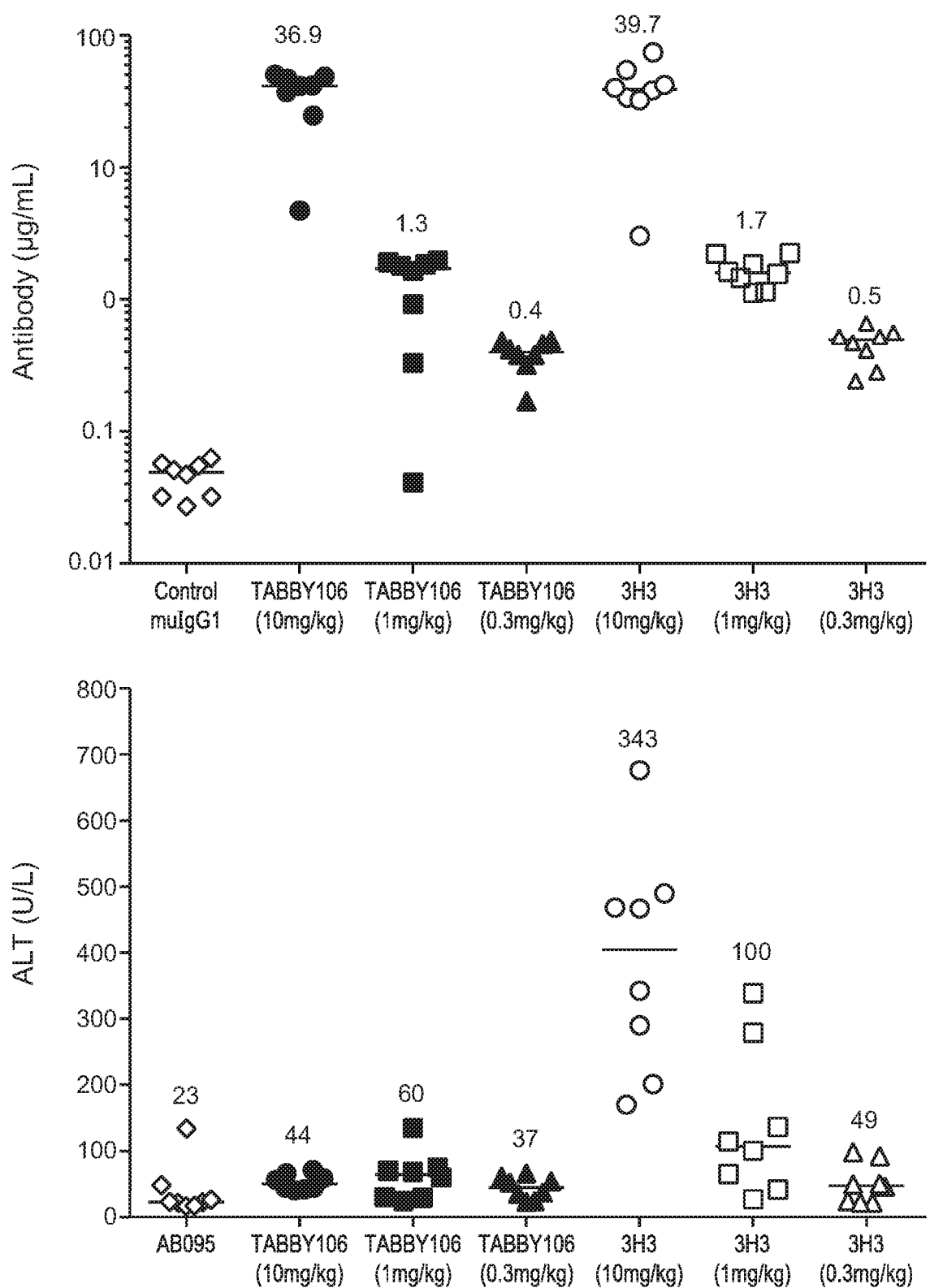
FIG. 9 shows blood antibody levels (upper graph) and alanine aminotransferase (ALT) levels (lower graph) of CT26 tumor model in Balb/c mice after dosing with anti-4-1BB antibody 3H3-ratIgG$_{2a}$ or chimeric antibody TABBY106-muIgG$_1$.

TABBY106-muIgG$_1$ demonstrated lower effects on elevating liver enzyme levels than literature anti-4-1BB antibody 3H3 (FIG. 9). Blood antibody levels (in µg/mL) for each antibody were comparable at all dose levels of 0.3, 1, or 10 mg/kg (upper graph), measured 1 hour after the third dose in the antitumor trial depicted in FIG. 8. However, in terms of liver enzyme alanine aminotransferase (ALT) levels (lower graph), 3H3 showed dose-dependent elevation at 1 and 10 mg/kg doses, while TABBY106-muIgG$_1$ did not exhibit any significant increases even at the highest 10 mg/kg dose.

Figure 10:
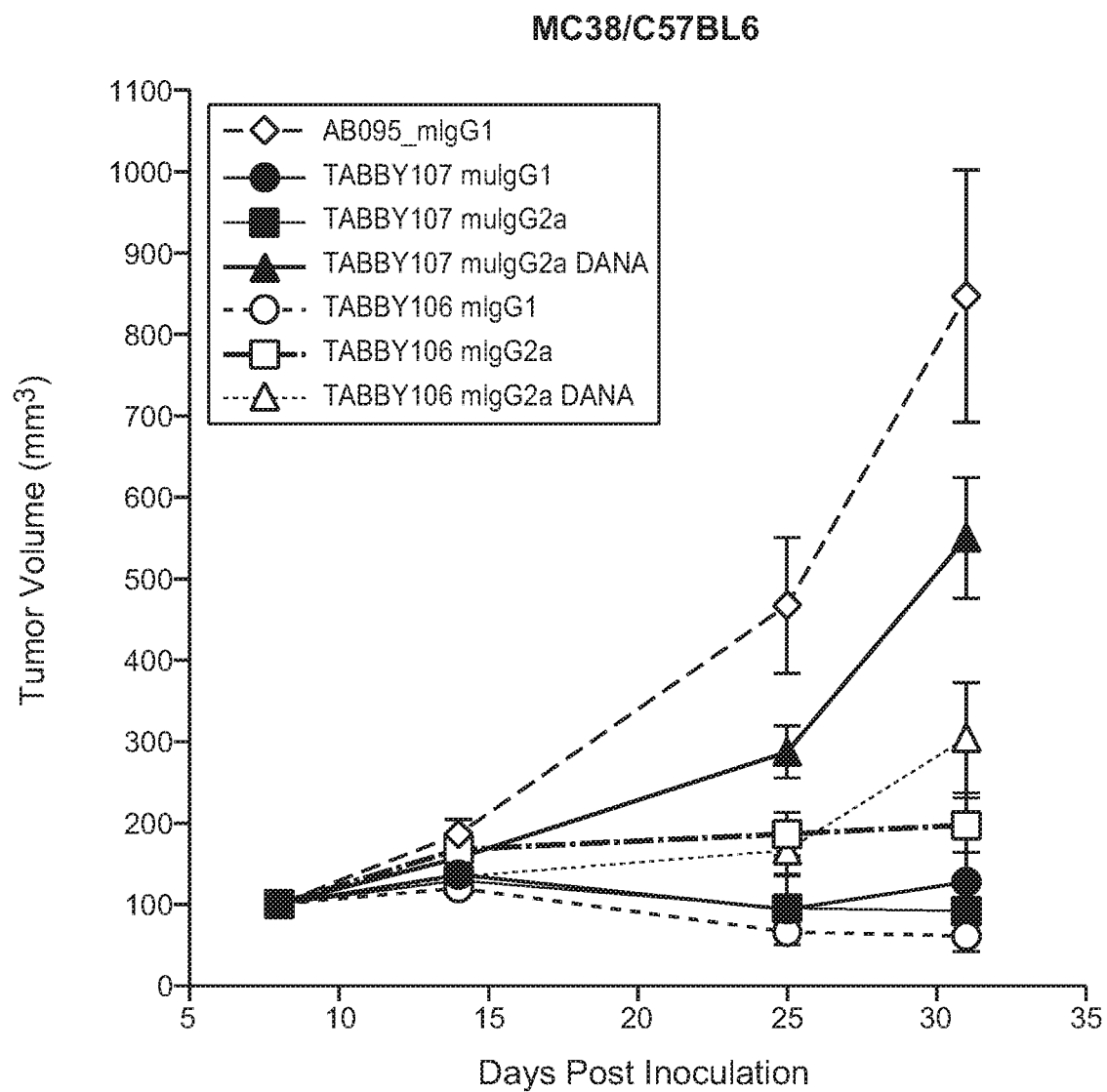
FIG. 10 shows the volume of MC-38 adenocarcinoma tumors in C57BL6 mice after dosing with an exemplary chimeric anti-4-1BB antibody or control (AB095).

Example 8: Exemplary Anti-4-1BB Antibodies Are Effective Against MC-38 Tumors in C57BL6 Mice Chimeric anti-4-1BB antibodies TABBY106 and TABBY107 bearing murine constant regions showed tumor growth inhibition on MC-38 colorectal adenocarcinoma tumors in C57BL6 mice. FIG. 10 depicts the effect on growth of MC-38 tumors after 10 mg/kg of chimeric antibody or control AB095-muIgG1 dosed intraperitoneally q7d×3 (i.e., once every seven days for a total of three doses). Different murine constant regions in the chimeric anti-4-1BB antibodies were evaluated, including muIgG$_1$, muIgG$_{2a}$, and muIgG$_{2a}$ with D265A and N297A mutations ("DANA"). The DANA mutations have been reported to afford lower FcγR binding. See, U.S. Pat. No. 7,332,581.

For both TABBY106 and TABBY107, the antibodies bearing muIgG$_1$ or muIgG$_{2a}$ constant regions exhibited significant inhibition of tumor growth. The chimeric anti-4-1BB antibodies bearing muIgG$_{2a}$ DANA constant regions exhibited a lower level of efficacy at the same dosing levels, suggesting that the effect on inhibiting growth of MC-38 tumors in C57BL6 mice by agonistic anti-4-1BB antibodies was driven at least in part by antibody FcγR binding.

Figure 11:
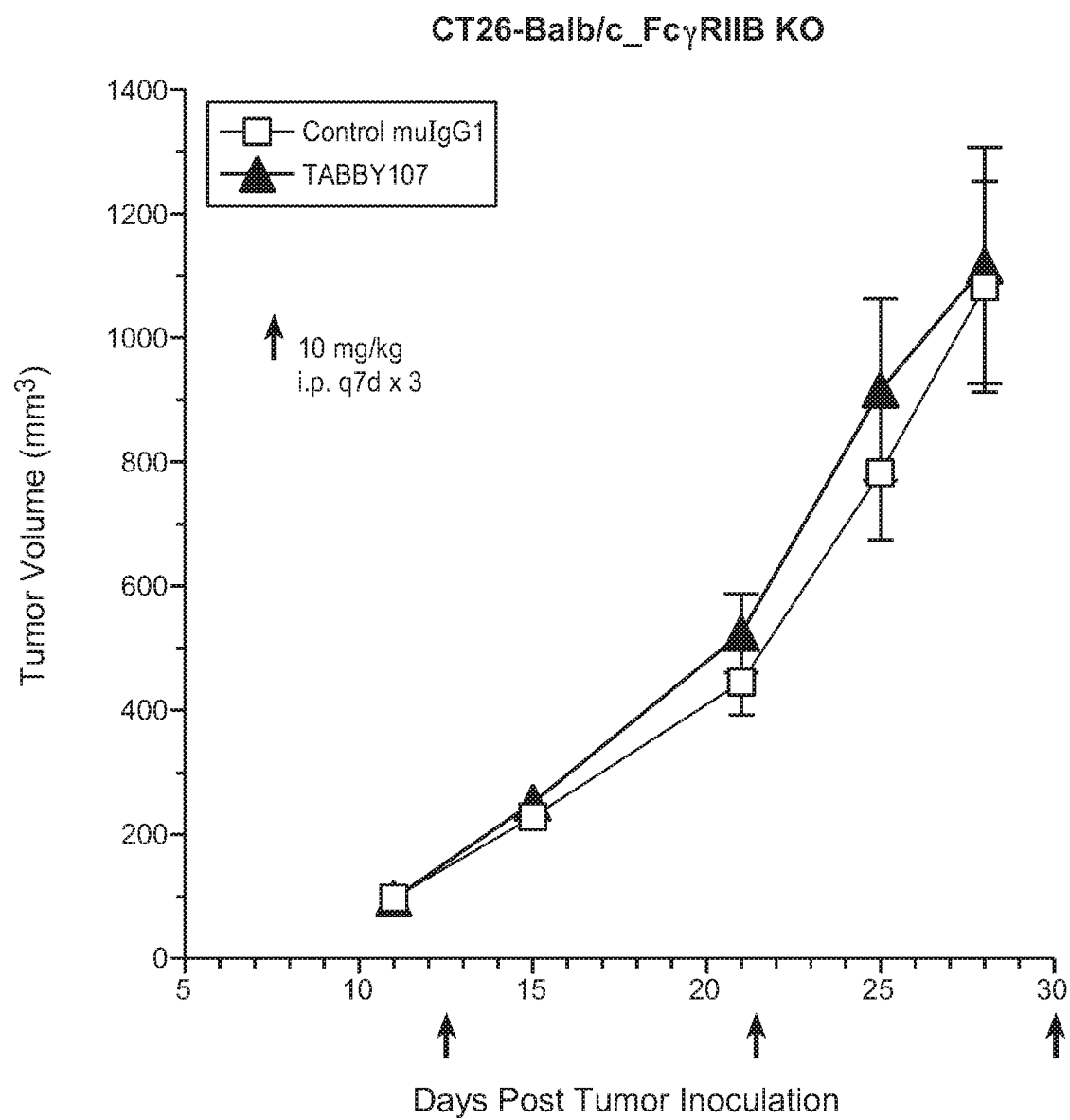
FIG. 11 shows the volume of CT26 tumors in Balb/c mice lacking FcγRIIB expression after 10 mg/kg intraperitoneal dosing once every seven days for a total of three doses of chimeric anti-4-1BB antibody TABBY107-muIgG$_1$ or control muIgG$_1$ antibody.

Example 9: Effect of an Anti-4-1BB Antibody on Tumors in Mice Lacking FcγRIIB Expression Exemplary chimeric antibody TABBY107-muIgG$_1$, i.e., with rat variable domains and murine IgG1 constant region, was evaluated for effects in Balb/c-FcγRIIB knockout mice bearing CT26 tumors. FIG. 11 depicts the effect on growth of CT26 tumors after 10 mg/kg of chimeric antibody or control dosed intraperitoneally q7d×3 (i.e., once every seven days for a total of three doses). Chimeric anti-4-1BB antibody TABBY107-muIgG$_1$ did not show any significant effect on inhibiting tumor growth as compared with the same dose of control antibody.

Example 10: Anti-4-1BB Antibody TABBY106 in Combination with Anti-PD-1 Antibody is Effective Against Melanoma Tumors The chimeric anti-4-1BB antibody TABBY106-muIgG$_1$ was effective in inhibiting B16F10 melanoma tumors in C57BL6 mice when dosed in combination with a proprietary anti-PD-1 antibody. Exemplary protocols for this tumor model may be found, for instance, in Overwijk and Restifo, Curr. Protoc. Immunol. 2001 May; CHAPTER: Unit-20.1.

Figure 12:
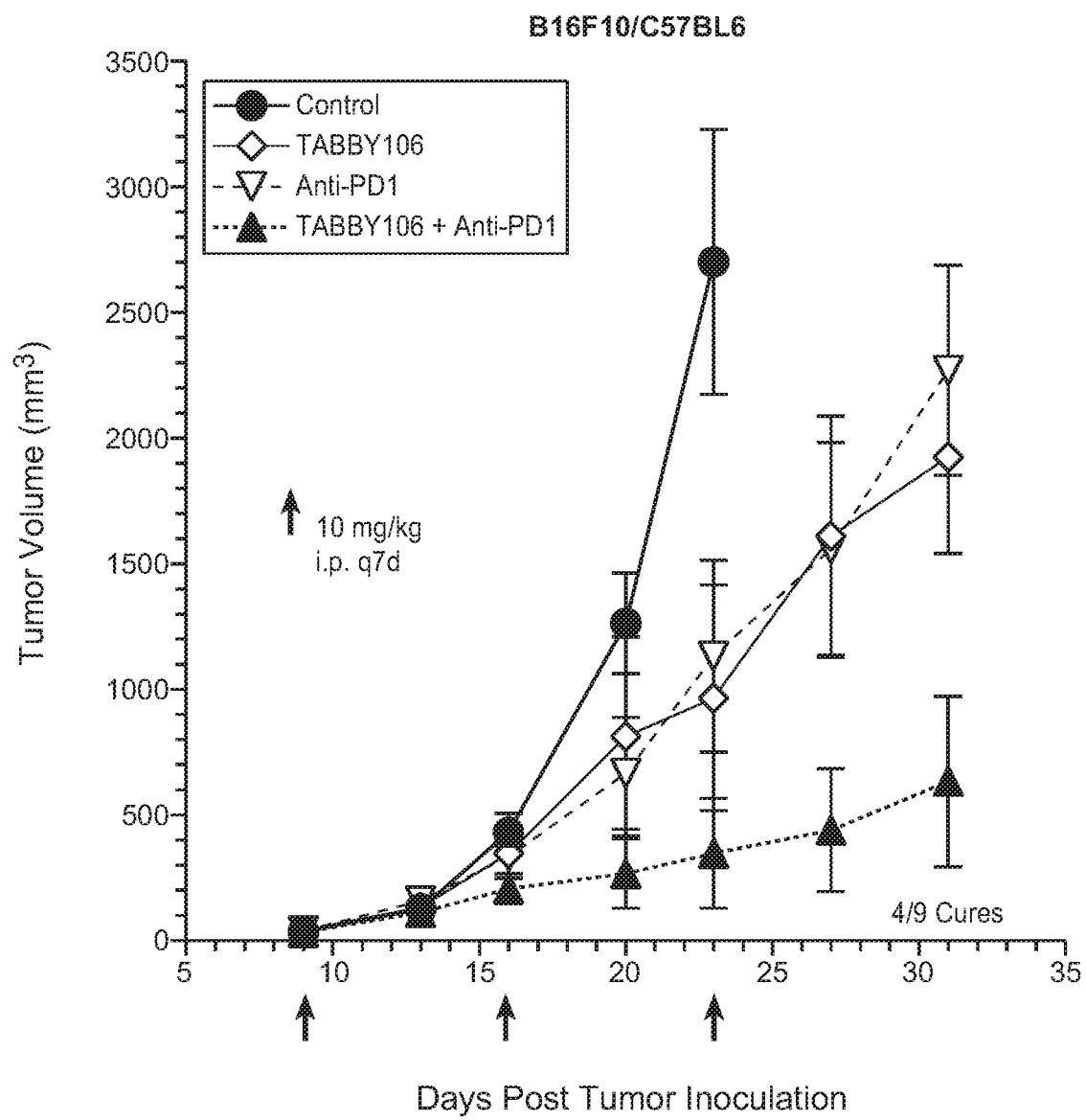
FIG. 12 depicts tumor volume after dosing with exemplary anti-4-1BB antibody TABBY106-mIgG$_1$, an anti-PD-1 antibody, or a combination of TABBY106-muIgG$_1$ and the anti-PD-1 antibody on B16F10 melanoma tumors in C57BL6 mice ("B16F10/C57BL6").

FIG. 12 shows the antitumor effects of an anti-4-1BB antibody combined with an anti-PD-1 antibody. Mice were dosed intraperitoneally with 10 mg/kg antibody q7d×3 (i.e., once every seven days for a total of three doses total), or with 10 mg/kg each of the anti-4-1-BB and the anti-PD-1 antibodies. Either the anti-4-1BB or the anti-PD-1 antibody at 10 mg/kg had no significant antitumor effects as a monotherapy in this model. But the combination of anti-4-1BB antibody TABBY106-muIgG1 with the anti-PD-1 antibody significantly reduced the growth rate of B16F10 melanoma tumors in C57BL6 mice, and led to cures in four out of nine animals. In the context of this Example, a "cure" showed an animal in which the tumor was unmeasurable after treatment, thereby indicating complete tumor regression.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An anti-4-1BB antibody or binding fragment thereof comprising (i) a $V_H$ chain comprising three CDRs; and (ii) a $V_L$ chain comprising three CDRs, wherein:
$V_H$ CDR #1 is GYTFTSYYIY (SEQ ID NO:16);
$V_H$ CDR #2 is NIWPGNGGTFYGEKFMG (SEQ ID NO:26);
$V_H$ CDR #3 is RPDYSGDDYFDY (SEQ ID NO:36);
$V_L$ CDR #1 is KLNSGNIGSYYVH (SEQ ID NO:56);
$V_L$ CDR #2 is RDDKRPD (SEQ ID NO:66); and
$V_L$ CDR #3 is HSYDSTITPV (SEQ ID NO:76),
or
$V_H$ CDR #1 is DYTFNDYWVS (SEQ ID NO:17);
$V_H$ CDR #2 is EIYPNSGATNFNGKFRG (SEQ ID NO:27);
$V_H$ CDR #3 is EYTRDWFAY (SEQ ID NO:37);
$V_L$ CDR #1 is RSSQSLLDSDGNTYLY (SEQ ID NO:57);
$V_L$ CDR #2 is LVSNLGS (SEQ ID NO:67); and
$V_L$ CDR #3 is MQPTHAPYT (SEQ ID NO:77).

2. The anti-4-1BB antibody or binding fragment of claim 1 which is human or humanized.

3. The anti-4-1BB antibody or binding fragment of claim 2, which comprises a $V_H$ chain corresponding in sequence to SEQ ID NO:109 and a $V_L$ chain corresponding in sequence to SEQ ID NO:161.

4. The anti-4-1BB antibody or binding fragment claim 2, which comprises a $V_H$ chain corresponding in sequence to SEQ ID NO:109 and a $V_L$ chain corresponding in sequence to SEQ ID NO:159.

5. The anti-4-1BB antibody or binding fragment claim 2, which comprises a $V_H$ chain corresponding in sequence to SEQ ID NO:111 and a $V_L$ chain corresponding in sequence to SEQ ID NO:165.

6. The anti-4-1BB antibody or binding fragment of claim 3, which is an IgG, optionally an $IgG_1$ or $IgG_4$.

7. The anti-4-1BB antibody of claim 6, which comprises a variant $IgG_1$ CH2 region comprising the amino acid substitution V273E or V273Y.

8. The anti-4-1BB antibody of claim 6, which comprises a variant $IgG_4$ hinge region comprising the amino acid substitution S228P.

9. A pharmaceutical composition comprising an anti-4-1BB antibody or binding fragment of claim 1, and a pharmaceutically acceptable carrier.

10. A nucleic acid comprising a nucleotide sequence encoding an anti-4-1BB antibody or binding fragment of claim 1.

11. A eukaryotic host cell transformed with a vector comprising the nucleic acid of claim 10.

12. A method of producing an anti-4-1BB antibody or binding fragment thereof, comprising: (a) culturing the host cell of claim 11 and (b) recovering the antibody or binding fragment.

13. The anti-4-1BB antibody or binding fragment of claim 4, which is an IgG, optionally an IgG1 or IgG4.

14. The anti-4-1BB antibody of claim 13, which comprises a variant IgG1 CH2 region comprising the amino acid substitution V273E or V273Y.

15. The anti-4-1BB antibody of claim 13, which comprises a variant IgG4 hinge region comprising the amino acid substitution S228P.

16. The anti-4-1BB antibody or binding fragment of claim 5, which is an IgG, optionally an IgG1 or IgG4.

17. The anti-4-1BB antibody of claim 16, which comprises a variant IgG1 CH2 region comprising the amino acid substitution V273E or V273Y.

18. The anti-4-1BB antibody of claim 16, which comprises a variant IgG4 hinge region comprising the amino acid substitution S228P.

* * * * *